United States Patent
Pint et al.

(10) Patent No.: US 11,588,418 B2
(45) Date of Patent: Feb. 21, 2023

(54) ENERGY HARVESTING DEVICES AND METHODS OF MAKING AND USE THEREOF

(71) Applicant: Vanderbilt University, Nashville, TN (US)

(72) Inventors: Cary L. Pint, Nashville, TN (US); Nitin Muralidharan, Nashville, TN (US)

(73) Assignee: Vanderbilt University, Nashville, TN (US)

(*) Notice: Subject to any disclaimer, the term of this patent is extended or adjusted under 35 U.S.C. 154(b) by 1233 days.

(21) Appl. No.: 16/058,046

(22) Filed: Aug. 8, 2018

(65) Prior Publication Data

US 2019/0052195 A1 Feb. 14, 2019

Related U.S. Application Data

(60) Provisional application No. 62/599,120, filed on Dec. 15, 2017, provisional application No. 62/542,639, filed on Aug. 8, 2017.

(51) Int. Cl.
| | |
|---|---|
| H02N 2/18 | (2006.01) |
| A61B 5/11 | (2006.01) |
| H01L 41/09 | (2006.01) |
| F03G 7/00 | (2006.01) |
| F03G 7/08 | (2006.01) |
| A61B 5/00 | (2006.01) |

(52) U.S. Cl.
CPC ............... *H02N 2/18* (2013.01); *A61B 5/11* (2013.01); *F03G 7/005* (2013.01); *F03G 7/08* (2013.01); *H01L 41/0906* (2013.01); *A61B 5/112* (2013.01); *A61B 5/4585* (2013.01)

(58) Field of Classification Search
CPC ........................................................ H02N 2/18
See application file for complete search history.

(56) References Cited

U.S. PATENT DOCUMENTS

| | | | |
|---|---|---|---|
| 2014/0099549 A1 | 4/2014 | Ceder et al. | |
| 2015/0099150 A1* | 4/2015 | Lee ................. | H01M 4/583 |
| | | | 165/104.19 |
| 2015/0330212 A1* | 11/2015 | Sassi ............... | E21B 47/07 |
| | | | 166/250.1 |
| 2018/0045184 A1* | 2/2018 | Must ............... | F03G 7/005 |
| 2018/0323359 A1* | 11/2018 | Li .................. | H01L 35/34 |

OTHER PUBLICATIONS

Anton, "A Review of Power Harvesting Using Piezoelectric Materials", (2003-2006). Smart Mater. Struct. 2007, 16, R1-R21.
Balakrishnan, et al., "Safety Mechanisms in Lithium-Ion Batteries", J. Power Sources 2006, 155, 401-414.
Çakir, et al., "Tuning of the Electronic and Optical Properties of Single-Layer Black Phosphorus by Strain", Phys. Rev. B: Condens. Matter Mater. Phys. 2014, 90, 205421.

(Continued)

*Primary Examiner* — J. San Martin
(74) *Attorney, Agent, or Firm* — Meunier Carlin & Curfman LLC

(57) ABSTRACT

Disclosed herein are energy harvesting devices and methods of making and use thereof. The energy harvesting devices can efficiently harvest energy for motions at a frequency of 5 Hz or less.

18 Claims, 44 Drawing Sheets

(56) References Cited

OTHER PUBLICATIONS

Cannarella, et al., "Toward Low-Frequency Mechanical Energy Harvesting Using Energy-Dense Piezoelectrochemical Materials", Adv. Mater. 2015, 27, 7440-7444.
Castellanos-Gomez, et al., "Local Strain Engineering in Atomically Thin MoS2", Nano Lett. 2013, 13, 5361-5366.
Chen, et al., "Two-Fold Anisotropy Governs Morphological Evolution and Stress Generation in Sodiated Black Phosphorus for Sodium Ion Batteries", Nano Lett. 2017, 17, 2299-2306.
Cohn, et al., "Ultrafast Solvent-Assisted Sodium Ion Intercalation into Highly Crystalline Few-Layered Graphene", Nano Lett. 2015, 16, 543-548.
Dahbi, "Black Phosphorus as a High-Capacity, High-Capability Negative Electrode for Sodium-Ion Batteries: Investigation of the Electrode/Electrolyte Interface", Chem. Mater. 2016, 28, 1625-1635.
Danion, et al., "Stride Variability in Human Gait: The Effect of Stride Frequency and Stride Length", Gait Posture 2003, 18, 69-77.
Fei, et al., "Strain-Engineering the Anisotropic Electrical Conductance of Few-Layer Black Phosphorus", Nano Lett. 2014, 14, 2884-2889.
Hou, et al., "Flexible Ionic Diodes for Low-Frequency Mechanical Energy Harvesting", Adv. Energy Mater. 2016, 7, 1601983.
Jiang, et al., "Negative Poisson's Ratio in Single-Layer Black Phosphorus", Nat. Commun. 2014, 5, 4727.
Kim, et al., "Electrochemically driven Mechanical Energy Harvesting", Doctoral Thesis, Massachusetts Institute of Technology, 2016.
Kim, et al., "Electrochemically Driven Mechanical Energy Harvesting", Nat. Commun. 2016, 7, 10146.
Koka, et al., "Vertically Aligned BaTiO3 Nanowire Arrays for Energy Harvesting", Energy Environ. Sci. 2014, 7, 288-296.
Li, et al., "Energy Harvesting from Low Frequency Applications Using Piezoelectric Materials", Appl. Phys. Rev. 2014, 1, 041301.
Liu, et al., "Design and Fabrication of Multifunctional Structural Batteries", J. Power Sources 2009, 189, 646-650.
Liu, et al., "Effects of Cycling Ranges on Stress and Capacity Fade in Lithium-Ion Pouch Cells", J. Electrochem. Soc. 2016, 163, A2501-A2507.
Mummolo, et al., "Quantifying Dynamic Characteristics of Human Walking for Comprehensive Gait Cycle", J. Biomech. Eng. 2013, 135, 091006.
Muralidharan, et al., "Strain Engineering to Modify the Electrochemistry of Energy Storage Electrodes", Sci. Rep. 2016, 6, 27542.
Muralidharan, et al., "Tunable Mechanochemistry of Lithium Battery Electrodes", ACS Nano 2017, 11, 6243-6251.
Muralidharan, "Ultralow Frequency Electrochemical-Mechanical Strain Energy Harvester Using 2D Black Phosphorous Nanosheets", ACS Energy Letters, 2017, 2, 1797-1803.
Oakes, et al., "Interface Strain in Vertically Stacked Two-Dimensional Heterostructured Carbon-MoS2 Nanosheets Controls Electrochemical Reactivity", Nat. Commun. 2016, 7, 11796.
Oakes, et al., "One Batch Exfoliation and Assembly of Two-Dimensional Transition Metal Dichalcogenide Nanosheets Using Electrophoretic Deposition", J. Electrochem. Soc. 2015, 162, D3063-D3070.
Oakes, et al., "Roll-to-Roll Nanomanufacturing of Hybrid Nanostructures for Energy Storage Device Design", ACS Appl. Mater. Interfaces 2015, 7, 14201-14210.
Orrego, et al., "Harvesting Ambient Wind Energy with an Inverted Piezoelectric Flag", Appl. Energ. 2017, 194, 212-222.
Qi, et al., "Nanotechnology-Enabled Flexible and Biocompatible Energy Harvesting", Energy Environ. Sci. 2010, 3, 1275-1285.
Qin, et al., "Microfibre-Nanowire Hybrid Structure for Energy Scavenging", Nature 2008, 451, 809-813.
Quartarone, et al., "Electrolytes for Solid-State Lithium Rechargeable Batteries: Recent Advances and Perspectives", Chem. Soc. Rev. 2011, 40, 2525-2540.
Salisbury, "Ultrathin device harvests electricity from human motion", Published online Jul. 21, 2017. Accessed Aug. 3, 2017 at https://news.vanderbilt.edu/2017/07/21/device-harvests-electricity-human-motion/.
Schiffer, et al., "Characterization and Model of Piezoelectrochemical Energy Harvesting Using Lithium ion Batteries", Exp. Mech. 2017, DOI: 10.1007/s 11340-017-0291-1.
Schiffer, et al., "Strain Derivatives for Practical Charge Rate Characterization of Lithium Ion Electrodes", J. Electrochem. Soc. 2016, 163, A427-A433.
Sun, et al., "Phosphorene-Graphene Hybrid Material as a High-Capacity Anode for Sodium-Ion Batteries", Nat. Nanotechnol. 2015, 10, 980-985.
Tavassol, et al., "Electrochemical Stiffness in Lithium-Ion Batteries", Nat. Mater. 2016, 15, 1182-1187.
Wang, et al., "Thermal Runaway Caused Fire and Explosion of Lithium Ion Battery", J. Power Sources 2012, 208, 210-224.
Wu, et al., "Energy Harvesters for Wearable and Stretchable Electronics: From Flexibility to Stretchability", Adv. Mater. 2016, 28, 9881-9919.
Xu, et al., "Self-Powered Nanowire Devices", Nat. Nanotechnol. 2010, 5, 366-373.
Zhang, "Chemomechanical Modeling of Lithiation-Induced Failure in High-Volume-Change Electrode Materials for Lithium Ion Batteries", NPJ Comput. Mater. 2017, 3, 1-11.
Zi, et al., "Harvesting Low-Frequency (<5 Hz) Irregular Mechanical Energy: A Possible Killer Application of Triboelectric Nanogenerator", ACS Nano 2016, 10, 4797-805.

* cited by examiner

Energy Harvester Configuration

ENERGY HARVESTING DEVICES AND METHODS OF MAKING AND USE THEREOF

CROSS-REFERENCE TO RELATED APPLICATIONS

This application claims the benefit of priority to U.S. Provisional Application No. 62/542,639 filed Aug. 8, 2017, and U.S. Provisional Application No. 62/599,120 filed Dec. 15, 2017, which are both hereby incorporated herein by reference in their entireties.

STATEMENT OF GOVERNMENT SUPPORT

This invention was made with Government support under Grant No. CMMI 1400424 awarded by the National Science Foundation. The Government has certain rights in the invention.

BACKGROUND

Advances in piezoelectric or triboelectric materials have enabled high-frequency platforms for mechanical energy harvesting (>10 Hz); however, virtually all human motions occur below 5 Hz and therefore limits application of these harvesting platforms to human motions. To overcome this, new device platforms need to be developed with the capability to operate at high mechanical conversion efficiencies and harvest energy simultaneously through full duration of low-frequency human motions. The devices and methods described herein address these and other needs.

SUMMARY

In accordance with the purposes of the disclosed devices and methods, as embodied and broadly described herein, the disclosed subject matter relates to energy harvesting devices and methods of making and use thereof.

Additional advantages of the disclosed devices and methods will be set forth in part in the description which follows, and in part will be obvious from the description. The advantages of the disclosed devices will be realized and attained by means of the elements and combinations particularly pointed out in the appended claims. It is to be understood that both the foregoing general description and the following detailed description are exemplary and explanatory only and are not restrictive of the disclosed devices and methods, as claimed.

The details of one or more embodiments of the invention are set forth in the accompanying drawings and the description below. Other features, objects, and advantages of the invention will be apparent from the description and drawings, and from the claims.

DESCRIPTION OF FIGURES

The accompanying figures, which are incorporated in and constitute a part of this specification, illustrate several aspects of the disclosure, and together with the description, serve to explain the principles of the disclosure.

DETAILED DESCRIPTION

Figure 1:
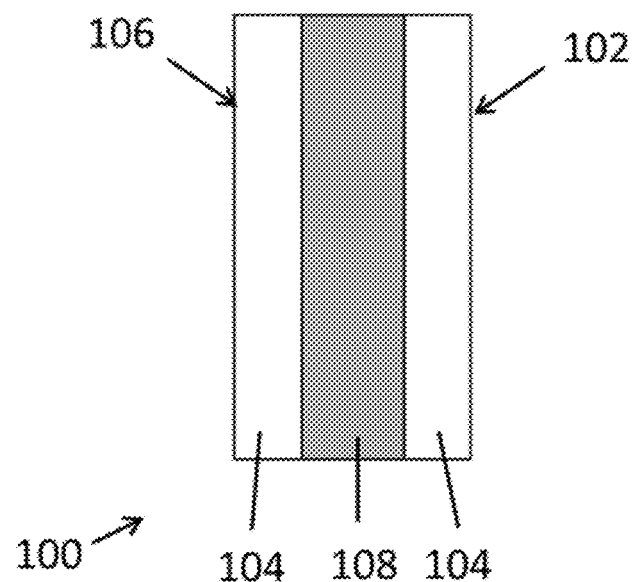
FIG. 1 is a schematic diagram of an exemplary energy harvesting device.

The devices and methods described herein may be understood more readily by reference to the following detailed description of specific aspects of the disclosed subject matter and the Examples included therein.

Before the present devices and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

It is understood that throughout this specification the identifiers "first" and "second" are used solely to aid the reader in distinguishing the various components, features, or steps of the disclosed subject matter. The identifiers "first" and "second" are not intended to imply any particular order, amount, preference, or importance to the components or steps modified by these terms.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

Energy Harvesting Devices Disclosed herein are energy harvesting devices. More specifically, according to the aspects illustrated herein, there are provided electrochemical-mechanical energy harvesters that can generate current through migration of ions.

Referring now to FIG. 1, in some examples, the energy harvesting devices 100 comprise: a first electrode 102 comprising a first material 104; a second electrode 106 comprising the first material 104; and a porous separator 108 disposed between the first electrode 102 and the second electrode 106 such that the porous separator 108 is in contact with the first electrode 102 and the second electrode 106; wherein the energy harvesting device 100 is configured to convert a mechanical strain to an electrical current, thereby harvesting energy.

Figure 2:
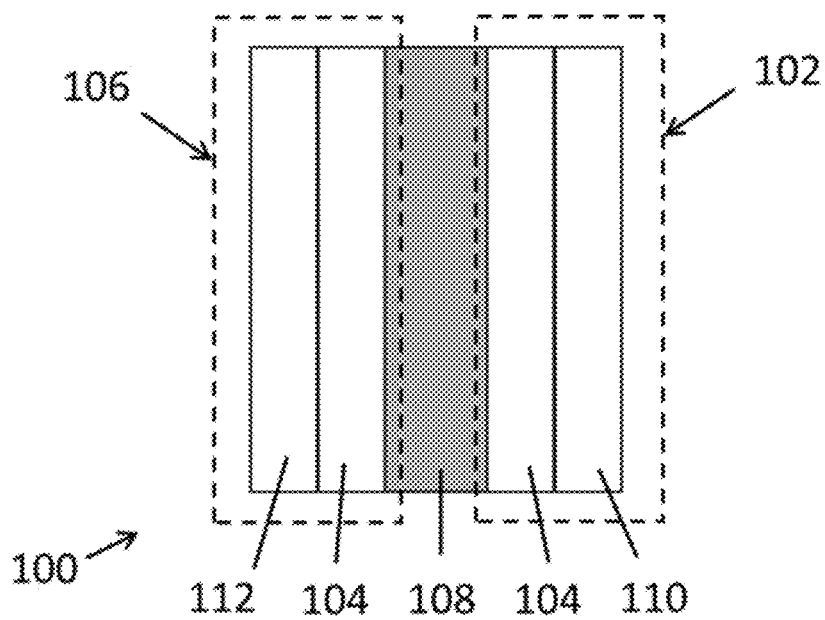
FIG. 2 is a schematic diagram of an exemplary energy harvesting device.

Referring now to FIG. 2, in some examples, the first electrode 102 further comprises a first conducting layer 110 and wherein the first material 104 is disposed on the first conducting layer 110 and in electrical contact with the first conducting layer 110. In some examples, the second electrode 106 further comprises a second conducting layer 112 and wherein the first material 104 is disposed on the second conducting layer 112 and in electrical contact with the second conducting layer 112. The first conducting layer and/or the second conducting layer can, for example, comprise(s) a transparent conducting oxide, a metal oxide, a conducting polymer, a carbon material, a metal, or a combination thereof. The metal can comprise, for example, a metal selected from the group consisting of Be, Mg, Al, Ca, Sc, Ti, V, Cr, Mn, Fe, Co, Ni, Cu, Zn, Ga, Sr, Y, Zr, Nb, Mo, Tc, Ru, Rh, Pd, Ag, Cd, In, Sn, Ba, Hf, Ta, W, Re, Os, Ir, Pt, Au, Hg, Tl, Pb, Bi, La, Ce, Pr, Nd, Pm, Sm, Eu, Gd, Tb, Dy, Ho, Er, Tm, Yb, and combinations thereof. In some examples, the metal can comprise an alloy. Examples of conducting polymers include, but are not limited to, polyacetylene, polyalanine, poly(3,4-ethylenedioxythiophene) polystyrene sulfonate ("PEDOT-PSS"), and combinations thereof.

Examples of carbon materials include, but are not limited to, graphitic carbon and graphites, including pyrolytic graphite (e.g., highly ordered pyrolytic graphite (HOPG)) and isotropic graphite, amorphous carbon activated carbon, hard carbon, carbon black, carbon fiber, single- or multi-walled carbon nanotubes, graphene, glassy carbon, diamond-like carbon (DLC) or doped DLC, such as boron-doped diamond, pyrolyzed photoresist films, and others known in the art. In some examples, the first conducting layer and/or the second conducting layer comprise(s) graphene, copper, or a combination thereof.

In some examples, the first conducting layer and/or the second conducting layer can comprise a transparent conducting oxide. In some examples, the first conducting layer and/or the second conducting layer can comprise a transparent conducting oxide selected from indium doped tin oxide, tin doped indium oxide, fluorine doped tin oxide, and combinations thereof.

In some examples, the first conducting layer and/or the second conducting layer can comprise a metal oxide. Examples of metal oxides include simple metal oxides (e.g., with a single metal element) and mixed metal oxides (e.g., with different metal elements). The metal oxide can, for example, comprise a metal selected from the group consisting of Cd, Cr, Cu, Ga, In, Ni, Sn, Ti, W, Zn, and combinations thereof. In some examples, the conducting layer can comprise CdO, $CdIn_2O_4$, $Cd_2SnO_4$, $Cr_2O_3$, $CuCrO_2$, $CuO_2$, $Ga_2O_3$, $In_2O_3$, NiO, $SnO_2$, $TiO_2$, $ZnGa_2O_4$, ZnO, InZnO, InGaZnO, InGaO, ZnSnO, $Zn_2SnO_4$, CdSnO, $WO_3$, or combinations thereof.

The loading of the first material on the first electrode and/or the second electrode can, for example, be 0.1 $mg/cm^2$ or more (e.g., 0.2 $mg/cm^2$ or more, 0.3 $mg/cm^2$ or more, 0.4 $mg/cm^2$ or more, 0.5 $mg/cm^2$ or more, 0.6 $mg/cm^2$ or more, 0.7 $mg/cm^2$ or more, 0.8 $mg/cm^2$ or more, 0.9 $mg/cm^2$ or more, 1 $mg/cm^2$ or more, 1.5 $mg/cm^2$ or more, 2 $mg/cm^2$ or more, 2.5 $mg/cm^2$ or more, 3 $mg/cm^2$ or more, 3.5 $mg/cm^2$ or more, 4 $mg/cm^2$ or more, 4.5 $mg/cm^2$ or more, 5 $mg/cm^2$ or more, 5.5 $mg/cm^2$ or more, 6 $mg/cm^2$ or more, 6.5 $mg/cm^2$ or more, 7 $mg/cm^2$ or more, 7.5 $mg/cm^2$ or more, 8 $mg/cm^2$ or more, 8.5 $mg/cm^2$ or more, or 9 $mg/cm^2$ or more). In some examples, the loading of the first material on the first electrode and/or the second electrode can be 10 $mg/cm^2$ or less (e.g., 9.5 $mg/cm^2$ or less, 9 $mg/cm^2$ or less, 8.5 $mg/cm^2$ or less, 8 $mg/cm^2$ or less, 7.5 $mg/cm^2$ or less, 7 $mg/cm^2$ or less, 6.5 $mg/cm^2$ or less, 6 $mg/cm^2$ or less, 5.5 $mg/cm^2$ or less, 5 $mg/cm^2$ or less, 4.5 $mg/cm^2$ or less, 4 $mg/cm^2$ or less, 3.5 $mg/cm^2$ or less, 3 $mg/cm^2$ or less, 2.5 $mg/cm^2$ or less, 2 $mg/cm^2$ or less, 1.5 $mg/cm^2$ or less, 1 $mg/cm^2$ or less, 0.9 $mg/cm^2$ or less, 0.8 $mg/cm^2$ or less, 0.7 $mg/cm^2$ or less, 0.6 $mg/cm^2$ or less, 0.5 $mg/cm^2$ or less, 0.4 $mg/cm^2$ or less, or 0.3 $mg/cm^2$ or less). The loading of the first material on the first electrode and/or the second electrode can range from any of the minimum values described above to any of the maximum values describes above. For example, the loading of the first material on the first electrode and/or the second electrode can be from 0.1 $mg/cm^2$ to 10 $mg/cm^2$ (e.g., from 0.1 $mg/cm^2$ to 9 $mg/cm^2$, from 0.1 $mg/cm^2$ to 8 $mg/cm^2$, from 0.1 $mg/cm^2$ to 7 $mg/cm^2$ from 0.1 $mg/cm^2$ to 6 $mg/cm^2$, from 0.5 $mg/cm^2$ to 5 $mg/cm^2$, from 0.5 $mg/cm^2$ to 4 $mg/cm^2$, 0.5 $mg/cm^2$ to 3 $mg/cm^2$, 0.6 $mg/cm^2$ to 2.5 $mg/cm^2$, 0.7 $mg/cm^2$ to 2 $mg/cm^2$, 0.8 $mg/cm^2$ to 1.5 $mg/cm^2$, or from 0.9 $mg/cm^2$ to 1 $mg/cm^2$).

The first material 104 comprises a plurality of particles and a plurality of ions. In some examples, the plurality of ions are intercalated within the plurality of particles. As used herein, "intercalate" refers to the incorporation of the plurality of ions within the structure of the plurality of particles. In some examples, the plurality of ions are alloyed with the plurality of particles.

The plurality of particles can have an average lateral dimension. "Average lateral dimension" and "mean lateral dimension" are used interchangeably herein, and generally refer to the statistical mean particle size of the particles in a population of particles. For example, the average lateral dimension for a plurality of particles can refer, for example, to the hydrodynamic size of the particle. As used herein, the hydrodynamic size of a particle can refer to the largest linear distance between two points on the surface of the particle. The average lateral dimension can be measured using methods known in the art, such as evaluation by scanning electron microscopy, transmission electron microscopy, and/or dynamic light scattering.

In some examples, the plurality of particles can have an average lateral dimension of 10 nanometers (nm) or more (e.g., 20 nm or more, 30 nm or more, 40 nm or more, 50 nm or more, 60 nm or more, 70 nm or more, 80 nm or more, 90 nm or more, 100 nm or more, 110 nm or more, 120 nm or more, 130 nm or more, 140 nm or more, 150 nm or more, 200 nm or more, 250 nm or more, 300 nm or more, 350 nm or more, 400 nm or more, 450 nm or more, 500 nm or more, 600 nm or more, 700 nm or more, 800 nm or more, 900 nm or more, 1 micrometer (micron, μm) or more, 2 μm or more, 3 μm or more, 4 μm or more, or 5 μm or more). In some examples, the plurality of particles can have an average lateral dimension of 10 micrometers (microns, μm) or less (e.g., 9 μm or less, 8 μm or less, 7 μm or less, 6 μm or less, 5 μm or less, 4 μm or less, 3 μm or less, 2 μm or less, 1 μm or less, 900 nm or less, 800 nm or less, 700 nm or less, 600 nm or less, 500 nm or less, 450 nm or less, 400 nm or less, 350 nm or less, 300 nm or less, 250 nm or less, 200 nm or less, 150 nm or less, 140 nm or less, 130 nm or less, 120 nm or less, 110 nm or less, 100 nm or less, 90 nm or less, 80 nm or less, 70 nm or less, 60 nm or less, or 50 nm or less). The average lateral dimension of the plurality of particles can range from any of the minimum values described above to any of the maximum values described above. For example, the plurality of particles can have an average lateral dimension of from 10 nm to 10 μm (e.g., from 10 nm to 5 μm, from 20 nm to 4 μm, from 30 nm to 3 μm, from 40 nm to 2 μm, from 50 nm to 1 μm, from 50 nm to 500 nm, from 50 nm to 200 nm, or from 70 nm to 110 nm).

The plurality of particles can have an average thickness. "Average thickness" and "mean thickness" are used interchangeably herein, and generally refer to the statistical mean thickness of the particles in a population of particles. The average thickness can be measured using methods known in the art, such as evaluation by scanning electron microscopy and/or transmission electron microscopy. In some examples, the plurality of particles can have an average thickness of 10 nanometers (nm) or more (e.g., 20 nm or more, 30 nm or more, 40 nm or more, 50 nm or more, 60 nm or more, 70 nm or more, 80 nm or more, 90 nm or more, 100 nm or more, 110 nm or more, 120 nm or more, 130 nm or more, 140 nm or more, 150 nm or more, 200 nm or more, 250 nm or more, 300 nm or more, 350 nm or more, 400 nm or more, 450 nm or more, 500 nm or more, 600 nm or more, 700 nm or more, 800 nm or more, 900 nm or more, 1 micrometer (micron, μm) or more, 2 μm or more, 3 μm or more, 4 μm or more, or 5 μm or more). In some examples, the plurality of particles can have an average thickness of 10 micrometers (microns, μm) or less (e.g., 9 μm or less, 8 μm or less, 7 μm or less, 6 μm or less, 5 μm or less, 4 μm or less, 3 μm or less, 2 μm or less, 1 μm or less, 900 nm or less, 800 nm or less, 700 nm or less, 600 nm or less, 500 nm or less, 450 nm or less, 400 nm or less, 350 nm or less, 300 nm or less, 250 nm or less, 200 nm or less, 150 nm or less, 140 nm or less, 130 nm or less, 120 nm or less, 110 nm or less, 100 nm or less, 90 nm or less, 80 nm or less, 70 nm or less, 60 nm or less, or 50 nm or less). The average thickness of the plurality of particles can range from any of the minimum values described above to any of the maximum values described above. For example, the plurality of particles can have an average thickness of from 10 nm to 10 μm (e.g., from 10 nm to 5 µm, from 10 nm to 4 µm, from 10 nm to 3 µm, from 10 nm to 2 µm, from 10 nm to 1 µm, from 10 nm to 500 nm, or from 10 nm to 300 nm).

For example, the plurality of particles can have an average thickness of from 1 atomic layer to 50 atomic layers, or from 3 atomic layers to 20 atomic layers.

The plurality of particles can, for example, comprise an allotrope of phosphorous, graphite, graphene, aluminum, a metal dichalcogenide, a metal oxide, or a combination thereof. In some examples, the plurality of particles can comprise an allotrope of phosphorous, graphene, or a combination thereof.

Examples of metal oxides include simple metal oxides (e.g., with a single metal element) and mixed metal oxides (e.g., with different metal elements). The metal oxide can, for example, comprise a metal selected from the group consisting of Be, Mg, Al, Ca, Sc, Ti, V, Cr, Mn, Fe, Co, Ni, Cu, Zn, Ga, Sr, Y, Zr, Nb, Mo, Tc, Ru, Rh, Pd, Ag, Cd, In, Sn, Ba, Hf, Ta, W, Re, Os, Ir, Pt, Au, Hg, Tl, Pb, Bi, La, Ce, Pr, Nd, Pm, Sm, Eu, Gd, Tb, Dy, Ho, Er, Tm, Yb, and combinations thereof.

In some examples, the metal dichalcogenide can comprise a metal disulfide. The metal disulfide can, for example, comprise a metal selected from the group consisting of Ti, Mo, Ta, W, and combinations thereof.

The plurality of ions can, for example, comprise any suitable cation or anion that can carry charge. In some examples, the plurality of ions can comprise a metal ion. In some examples, the plurality of ions can comprise a plurality of alkali metal ions. The plurality of alkali metal ions can, for example, comprise $Na^+$, $Li^+$, $K^+$, $Rb^+$, $Cs^+$, or a combination thereof. In some examples, the plurality of alkali metal ions can comprise $Na^+$ In some examples, the first material comprises a sodiated allotrope of phosphorous, such as sodiated black phosphorous.

The porous separator can, in some examples, comprise a polymer, such as an electrically insulating polymer. Examples of suitable polymers are known in the art, and include, but are not limited to, polypropylene, poly(methyl methacrylate), polyvinyl alcohol, polyamide, polycarbonate, polyester, polytetrafluoroethylene, and combinations thereof.

The porous separator further comprises an electrolyte. The electrolyte can comprise an ion source. For example, the electrolyte can comprise an ionic liquid. In some examples, the electrolyte can comprise monoglyme, diglyme, tetraglyme, a carbonate solvent, an ionic liquid, or a combination thereof with a dissolved ion source, such as a dissolved alkali metal salt. In some examples, the electrolyte can comprise a solid electrolyte. In some examples, the porous separator comprises a porous solid electrolyte.

The porous separator can, for example, comprise a plurality of pores having an average pore diameter of 500 nm or more (e.g., 600 nm or more, 700 nm or more, 800 nm or more, 900 nm or more, 1 µm or more, 2 µm or more, 3 µm or more, 4 µm or more, 5 µm or more, 10 µm or more, 15 µm or more, 20 µm or more, 30 µm or more, 40 µm or more, 50 µm or more, 100 µm or more, 150 µm or more, 200 µm or more, 250 µm or more, 300 µm or more, 400 µm or more, 500 µm or more, 600 µm or more, or 700 µm or more). In some examples, the porous separator can comprise a plurality of pores having an average pore diameter of 1 millimeter (mm) or less (e.g., 900 µm or less, 800 µm or less, 700 µm or less, 600 µm or less, 500 µm or less, 400 µm or less, 300 µm or less, 250 µm or less, 200 µm or less, 150 µm or less, 100 µm or less, 50 µm or less, 40 µm or less, 30 µm or less, 20 µm or less, 15 µm or less, 10 µm or less, 5 µm or less, 4 µm or less, 3 µm or less, 2 µm or less, 1 µm or less, 900 nm or less, or 800 nm or less). The average pore diameter of the plurality of pores of the porous separator can range from any of the minimum values described above to any of the maximum values described above. For example, the porous separator can comprise a plurality of pores having an average pore diameter of from 500 nm to 1 mm (e.g., from 500 nm to 1 µm, from 1 µm to 10 µm, from 10 µm to 100 µm, from 100 µm to 1 mm, or from 1 µm to 500 µm).

The mechanical strain can, for example, comprise pressing and/or bending the energy harvesting device. The mechanical strain can cause an ion located in the first electrode to intercalate, with or without a solvent shell, into the second electrode.

In some examples, the mechanical strain is generated at a frequency of 1 microHertz (µHz) or more (e.g., 2 µHz or more, 3 µHz or more, 4 µHz or more, 5 µHz or more, 10 µHz or more, 15 µHz or more, 20 µHz or more, 25 µHz or more, 30 µHz or more, 40 µHz or more, 50 µHz or more, 60 µHz or more, 70 µHz or more, 80 µHz or more, 90 µHz or more, 100 µHz or more, 150 µHz or more, 200 µHz or more, 250 µHz or more, 300 µHz or more, 350 µHz or more, 400 µHz or more, 450 µHz or more, 500 µHz or more, 600 µHz or more, 700 µHz or more, 800 µHz or more, 900 µHz or more, 1 milliHertz (mHz) or more, 2 mHz or more, 3 mHz or more, 4 mHz or more, 5 mHz or more, 10 mHz or more, 15 mHz or more, 20 mHz or more, 25 mHz or more, 30 mHz or more, 40 mHz or more, 50 mHz or more, 60 mHz or more, 70 mHz or more, 80 mHz or more, 90 mHz or more, 100 mHz or more, 150 mHz or more, 200 mHz or more, 250 mHz or more, 300 mHz or more, 350 mHz or more, 400 mHz or more, 450 mHz or more, 500 mHz or more, 600 mHz or more, 700 mHz or more, 800 mHz or more, 900 mHz or more, or 1 Hertz or more).

In some examples, the mechanical strain is generated at a frequency of 5 Hertz (Hz) or less (e.g., 4 Hz or less, 3 Hz or less, 2 Hz or less, 1 Hz or less, 900 mHz or less, 800 mHz or less, 700 mHz or less, 600 mHz or less, 500 mHz or less, 450 mHz or less, 400 mHz or less, 350 mHz or less, 300 mHz or less, 250 mHz or less, 200 mHz or less, 150 mHz or less, 100 mHz or less, 90 mHz or less, 80 mHz or less, 70 mHz or less, 60 mHz or less, 50 mHz or less, 40 mHz or less, 30 mHz or less, 25 mHz or less, 20 mHz or less, 15 mHz or less, 10 mHz or less, 5 mHz or less, 4 mHz or less, 3 mHz or less, 2 mHz or less, 1 mHz or less, 900 µHz or less, 800 µHz or less, 700 µHz or less, 600 µHz or less, 500 µHz or less, 450 µHz or less, 400 µHz or less, 350 µHz or less, 300 µHz or less, 250 µHz or less, 200 µHz or less, 150 µHz or less, 100 µHz or less, 90 µHz or less, 80 µHz or less, 70 µHz or less, 60 µHz or less, 50 µHz or less, 40 µHz or less, 30 µHz or less, 25 µHz or less, 20 µHz or less, 15 µHz or less, 10 µHz or less, or 5 µHz or less).

The frequency the mechanical strain is generated at can range from any of the minimum values described above to any of the maximum values described above. For example, the mechanical strain can be generated at a frequency of from 1 microHertz (µHz) to 5 Hz (e.g., from 1 µHz to 1 Hz, from 1 µHz to 500 mHz, from 1 µHz to 100 mHz, from 1 µHz to 10 mHz, or from 1 µHz to 1 mHz).

In some examples, the mechanical strain is generated by motion of a subject or an object. As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human In some examples, the mechanical strain is generated by the gait of a subject. In some examples, the mechanical strain can be generated by human motion. For example, the mechanical strain can be generated by human gait.

In some examples, the energy harvesting device can have a peak power of 1 nW/cm$^2$ or more (e.g., 2 nW/cm$^2$ or more, 3 nW/cm$^2$ or more, 4 nW/cm$^2$ or more, 5 nW/cm$^2$ or more, 6 nW/cm$^2$ or more, 7 nW/cm$^2$ or more, 8 nW/cm$^2$ or more, 9 nW/cm$^2$ or more, 10 nW/cm$^2$ or more, 15 nW/cm$^2$ or more, 20 nW/cm$^2$ or more, 25 nW/cm$^2$ or more, 30 nW/cm$^2$ or more, 35 nW/cm$^2$ or more, 40 nW/cm$^2$ or more, 45 nW/cm$^2$ or more, 50 nW/cm$^2$ or more, 60 nW/cm$^2$ or more, 70 nW/cm$^2$ or more, 80 nW/cm$^2$ or more, 90 nW/cm$^2$ or more, 100 nW/cm$^2$ or more, 150 nW/cm$^2$ or more, 200 nW/cm$^2$ or more, 250 nW/cm$^2$ or more, 300 nW/cm$^2$ or more, 350 nW/cm$^2$ or more, 400 nW/cm$^2$ or more, 450 nW/cm$^2$ or more, 500 nW/cm$^2$ or more, 600 nW/cm$^2$ or more, 700 nW/cm$^2$ or more, 800 nW/cm$^2$ or more, 900 nW/cm$^2$ or more, 1 μW/cm$^2$ or more, 1.5 μW/cm$^2$ or more, 2 μW/cm$^2$ or more, 2.5 μW/cm$^2$ or more, 3 μW/cm$^2$ or more, 3.5 μW/cm$^2$ or more, or 4 μW/cm$^2$ or more). In some examples, the energy harvesting device can have a peak power of 5 μW/cm$^2$ or less (e.g., 4.5 μW/cm$^2$ or less, 4 μW/cm$^2$ or less, 3.5 μW/cm$^2$ or less, 3 μW/cm$^2$ or less, 2.5 μW/cm$^2$ or less, 2 μW/cm$^2$ or less, 1.5 μW/cm$^2$ or less, 1 μW/cm$^2$ or less, 900 nW/cm$^2$ or less, 800 nW/cm$^2$ or less, 700 nW/cm$^2$ or less, 600 nW/cm$^2$ or less, 500 nW/cm$^2$ or less, 450 nW/cm$^2$ or less, 400 nW/cm$^2$ or less, 350 nW/cm$^2$ or less, 300 nW/cm$^2$ or less, 250 nW/cm$^2$ or less, 200 nW/cm$^2$ or less, 150 nW/cm$^2$ or less, 100 nW/cm$^2$ or less, 90 nW/cm$^2$ or less, 80 nW/cm$^2$ or less, 70 nW/cm$^2$ or less, 60 nW/cm$^2$ or less, 50 nW/cm$^2$ or less, 45 nW/cm$^2$ or less, 40 nW/cm$^2$ or less, 35 nW/cm$^2$ or less, 30 nW/cm$^2$ or less, 25 nW/cm$^2$ or less, 20 nW/cm$^2$ or less, 15 nW/cm$^2$ or less, 10 nW/cm$^2$ or less, 9 nW/cm$^2$ or less, 8 nW/cm$^2$ or less, 7 nW/cm$^2$ or less, 6 nW/cm$^2$ or less, or 5 nW/cm$^2$ or less). The peak power of the energy harvesting device can range from any of the minimum values described above to any of the maximum values described above. For example, the energy harvesting device can have a peak power of from 1 nW/cm$^2$ to 5 μW/cm$^2$ (e.g., from 10 nW/cm$^2$ to 5 μW/cm$^2$, from 50 nW/cm$^2$ to 5 μW/cm$^2$, from 100 nW/cm$^2$ to 5 μW/cm$^2$, from 500 nW/cm$^2$ to 5 μW/cm$^2$, or from 1 μW/cm$^2$ to 5 μW/cm$^2$).

The energy harvesting device can, for example, harvest an energy of 0.1 μJ/cm$^2$ or more (e.g., 0.2 μJ/cm$^2$ or more, 0.3 μJ/cm$^2$ or more, 0.4 μJ/cm$^2$ or more, 0.5 μJ/cm$^2$ or more, 0.6 μJ/cm$^2$ or more, 0.7 μJ/cm$^2$ or more, 0.8 μJ/cm$^2$ or more, 0.9 μJ/cm$^2$ or more, 1 μJ/cm$^2$ or more, 1.25 μJ/cm$^2$ or more, 1.5 μJ/cm$^2$ or more, 1.75 μJ/cm$^2$ or more, 2 μJ/cm$^2$ or more, 2.25 μJ/cm$^2$ or more, 2.5 μJ/cm$^2$ or more, 2.75 μJ/cm$^2$ or more, 3 μJ/cm$^2$ or more, 3.25 μJ/cm$^2$ or more, 3.5 μJ/cm$^2$ or more, 3.75 μJ/cm$^2$ or more, or 4 μJ/cm$^2$ or more). In some examples, the energy harvesting device can harvest an energy of 5 μJ/cm$^2$ or less (e.g., 4.75 μJ/cm$^2$ or less, 4.5 μJ/cm$^2$ or less, 4.25 μJ/cm$^2$ or less, 4 μJ/cm$^2$ or less, 3.75 μJ/cm$^2$ or less, 3.5 μJ/cm$^2$ or less, 3.25 μJ/cm$^2$ or less, 3 μJ/cm$^2$ or less, 2.75 μJ/cm$^2$ or less, 2.5 μJ/cm$^2$ or less, 2.25 μJ/cm$^2$ or less, 2 μJ/cm$^2$ or less, 1.75 μJ/cm$^2$ or less, 1.5 μJ/cm$^2$ or less, 1.25 μJ/cm$^2$ or less, 1 μJ/cm$^2$ or less, 0.9 μJ/cm$^2$ or less, 0.8 μJ/cm$^2$ or less, 0.7 μJ/cm$^2$ or less, 0.6 μJ/cm$^2$ or less, or 0.5 μJ/cm$^2$ or less). The energy harvested by the energy harvesting device can range from any of the minimum values described above to any of the maximum values described above. For example, the energy harvesting device can harvest an energy of from 0.1 μJ/cm$^2$ to 5 μJ/cm$^2$ (e.g., from 0.2 μJ/cm$^2$ to 5 μJ/cm$^2$, from 0.5 μJ/cm$^2$ to 5 μJ/cm$^2$, from 1 μJ/cm$^2$ to 5 μJ/cm$^2$, or from 2.5 μJ/cm$^2$ to 5 μJ/cm$^2$).

In some examples, the mechanical strain is generated by bending at a bending radius of 3 mm and with a frequency of 0.1 Hz and the energy harvesting device has a peak power of from 40 nW/cm$^2$ to 5 μW/cm$^2$. In some examples, the mechanical strain is generated by bending at a bending radius of 3 mm and with a frequency of 0.1 Hz and the energy harvesting device harvests an energy of from 0.2 μJ/cm$^2$ to 5 μJ/cm$^2$.

In some examples, the mechanical strain is generated by pressing with an applied load of 0.2 MPa and with a frequency of 0.1 Hz and the energy harvesting device has a peak power of from 9 nW/cm$^2$ to 5 μW/cm$^2$. In some examples, the mechanical strain is generated by pressing with an applied load of 0.2 MPa and with a frequency of 0.1 Hz and the energy harvesting device harvests an energy of from 0.7 μJ/cm$^2$ to 5 μJ/cm$^2$.

In some examples, the mechanical strain is generated by pressing with an applied load of 0.2 MPa and with a frequency of 0.01 Hz and the energy harvesting device has a peak power of from 9 nW/cm$^2$ to 5 μW/cm$^2$. In some examples, the mechanical strain is generated by pressing with an applied load of 0.2 MPa and with a frequency of 0.01 Hz and the energy harvesting device harvests an energy of from 0.7 μJ/cm$^2$ to 5 μJ/cm$^2$.

In some examples, the energy harvesting device harvests energy with an efficiency of 20% or more (e.g., 25% or more, 30% or more, 35% or more, 40% or more, 45% or more, or 50% or more).

The energy harvesting device can, in some examples, further comprise a packaging material substantially encapsulating the device. The packaging material can, for example, comprise an air-stable polymer. In some examples, the packaging material can comprise a dissolvable material.

In some examples, the energy harvesting device can comprise a dissolvable device, such that the energy harvesting device can be dissolved after use.

Methods of Making

Also disclosed herein are methods of making the energy harvesting devices described herein. For example, the methods of making the energy harvesting devices described herein can comprise: dispersing the first material in a solution, thereby forming a mixture; depositing the mixture on a conducting layer, thereby forming the first electrode; repeating the dispersing and depositing steps to form the second electrode or cutting the first electrode into two pieces thereby forming the first electrode and the second electrode; and sandwiching the porous separator between the first electrode and the second electrode, thereby forming the energy harvesting device.

In some examples, wherein the porous separator comprises a porous polymer, the method can further comprise forming the porous separator by soaking a porous polymer in the electrolyte.

Dispersing the first material in a solution can, for example, comprise sonication. In some examples, dispersing the first material in a solution can comprise exfoliating the first material.

Depositing the mixture on the conducting layer can, for example, comprise atomic layer deposition, chemical vapor deposition, electron beam evaporation, thermal evaporation, sputtering deposition, pulsed laser deposition, printing, lithographic deposition, spin coating, drop-casting, zone casting, dip coating, blade coating, spraying, slot die coating, curtain coating, electrophoretic deposition, or combinations thereof. In some examples, depositing the mixture on the conducting layer comprises electrophoretic deposition.

In some examples, the method can further comprise forming the conducting layer. In certain examples, wherein the conducting layer comprises graphene and copper, forming the conducting layer can comprise growing graphene on copper using chemical vapor deposition.

Methods of Use

Also disclosed herein are methods of use of the energy harvesting devices described herein, for example to harvest energy. For example, also disclosed herein are methods of harvesting energy using the energy harvesting devices described herein, the method comprising applying a mechanical strain to the energy harvesting device, thereby converting the mechanical strain to an electrical current and harvesting the energy.

The mechanical strain can, for example, comprise pressing and/or bending the energy harvesting device. The mechanical strain can cause an ion located in the first electrode to intercalate, with or without a solvent shell, into the second electrode.

In some examples, the mechanical strain is generated at a frequency of from 0.01 Hertz (Hz) to 5 Hz. For example, the mechanical strain can be generated at a frequency of 5 Hz or less, or 1 Hz or less.

In some examples, the mechanical strain is generated by motion of a subject or an object. In some examples, the mechanical strain is generated by the gait of a subject. In some examples, the mechanical strain is generated by human motion. For example, the mechanical strain can be generated by human gait.

The energy harvesting device can, in some examples, have a peak power of from 1 $nW/cm^2$ to 5 $\mu W/cm^2$. In some examples, the energy harvesting device can harvest an energy of from 0.1 $\mu J/cm^2$ to 5 $\mu J/cm^2$.

In some examples, the mechanical strain is generated by bending at a bending radius of 3 mm and with a frequency of 0.1 Hz and the energy harvesting device has a peak power of from 40 $nW/cm^2$ to 5 $\mu W/cm^2$. In some examples, the mechanical strain is generated by bending at a bending radius of 3 mm and with a frequency of 0.1 Hz and the energy harvesting device harvests an energy of from 0.2 $\mu J/cm^2$ to 5 $\mu J/cm^2$.

In some examples, the mechanical strain is generated by pressing with an applied load of 0.2 MPa and with a frequency of 0.1 Hz and the energy harvesting device has a peak power of from 9 $nW/cm^2$ to 5 $\mu W/cm^2$. In some examples, the mechanical strain is generated by pressing with an applied load of 0.2 MPa and with a frequency of 0.1 Hz and the energy harvesting device harvests an energy of from 0.7 $\mu J/cm^2$ to 5 $\mu J/cm^2$.

In some examples, the mechanical strain is generated by pressing with an applied load of 0.2 MPa and with a frequency of 0.01 Hz and the energy harvesting device has a peak power of from 9 $nW/cm^2$ to 5 $\mu W/cm^2$. In some examples, the mechanical strain is generated by pressing with an applied load of 0.2 MPa and with a frequency of 0.01 Hz and the energy harvesting device harvests an energy of from 0.7 $\mu J/cm^2$ to 5 $\mu J/cm^2$.

In some examples, the energy harvesting device harvests energy with an efficiency of 20% or more (e.g., 25% or more, 30% or more, 35% or more, 40% or more, 45% or more, or 50% or more).

The devices can be used in various articles of manufacture, such as, for example, textiles, fabrics, fibers, yarn, and the like comprising the energy harvesting devices described herein.

Examples of articles of manufacture include wearable energy harvesting devices comprising textiles, fabrics, fibers, yarn, and the like impregnated with the energy harvesting devices described herein.

The examples below are intended to further illustrate certain aspects of the systems and methods described herein, and are not intended to limit the scope of the claims.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of measurement conditions, e.g., component concentrations, temperatures, pressures and other measurement ranges and conditions that can be used to optimize the described process.

Example 1

An ambient mechanical energy harvester converts input mechanical energy into electrical energy, which can be transferred and utilized in other systems (Cannarella J and Arnold C B. *Adv. Mater.* 2015, 27, 7440-7444; Orrego S et al. *Appl. Energy* 2017, 194, 212-222). Conventional methods of ambient mechanical energy harvesting chemical-mechanical coupling commonly utilize a variety of piezoelectric and triboelectric materials (Qin Y et al. *Nature* 2008, 451, 809-813; Anton S R and Sodano H A. *Smart Mater. Struct.* 2007, 16, R1-R21; Wu H et al. *Adv. Mater.* 2016, 28, 9881-9919). Although these materials are capable of effective energy harvesting at high frequencies (>10 Hz), their performance drastically drops when these devices are operated under low frequency (<1-5 Hz) and static loading conditions corresponding to ambient human mechanical interactions (Cannarella J and Arnold C B. *Adv. Mater.* 2015, 27, 7440-7444; Wu H et al. *Adv. Mater.* 2016, 28, 9881-9919; Li H et al. *Appl. Phys. Rev.* 2014, 1, 041301).

Human gait is distributed at frequencies below 5 Hz, leaving high-frequency harvesters that operate at low conversion efficiencies to harvest energy in only a small window of a normal human motion (Mummolo C et al. *J. Biomech. Eng.* 2013, 135, 091006; Danion F et al. *Gait Posture* 2003, 18, 69-77). To overcome this, new device platforms need to be developed with the capability to operate at high mechanical conversion efficiencies and harvest energy simultaneously through full duration of low-frequency human motions. This requires the development of harvesting methodologies beyond existing materials and systems.

In this regard, researchers have recently started to investigate the mechanical-electrochemical coupling in conventional Faradaic energy storage materials and batteries. Observations by Kim et al. demonstrated a small potential difference that emerges in a silicon-lithium system that is instigated by mechanical stresses, which can be leveraged for strain energy harvesting (Kim S et al. *Nat. Commun.* 2016, 7, 10146). Similarly, other recent efforts have demonstrated stress-induced shifts to equilibrium potentials in electrochemical energy storage materials by using strain as a controlled input parameter, which reveals the origin of this electrochemical-mechanical coupling. These early studies leverage mechanical stresses, which are otherwise considered an adverse side-product of an ion-storing electrochemical system, to modulate the energetics of ion insertion that can be leveraged for strain energy harvesting (Tavassol H et al. *Nat. Mater.* 2016, 15, 1182-1187; Zhang S. *NPJ. Comput. Mater.* 2017, 3, 1-11). This allows high energy density storage through Faradaic reactions occurring in battery materials to be tapped in systems designed to use mechanical energy inputs to drive or control these reactions. Because battery materials natively undergo charge-discharge processes at low frequencies, harvesters built on the working principles of battery materials will exhibit a frequency range of operation that is better matched to low-frequency human motions (e.g., <5 Hz) (Cannarella J and Arnold C B. *Adv. Mater.* 2015, 27, 7440-7444; Schiffer Z and Arnold C. *Exp. Mech.* 2017, DOI: 10.1007/s11340-017-0291-1).

Whereas early studies discussing and leveraging the mechanochemical response of batteries have so far focused on thick bulk-like materials, two-dimensional (2D) materials present an exciting alternative for strain harvesting. Strain coupling into 2D materials can be highly efficient, unlike the case for bulk materials, and many 2D materials exhibit strain responses deviating from those of their bulk material counterparts that can be exploited in such devices (Muralidharan N et al. *Sci. Rep.* 2016, 6, 27542; Castellanos-Gomez A et al. *Nano Lett.* 2013, 13, 5361-5366). An example of this is 2D black phosphorus (BP), or phosphorene, which exhibits a negative Poisson's ratio in a single-layer configuration and exhibits an anisotropic optical/electronic response (Çakir D et al. *Phys. Rev. B: Condens. Matter Mater. Phys.* 2014, 90, 205421; Jiang J W and Park H S. *Nat. Commun.* 2014, 5, 4727; Fei R and Yang L. *Nano Lett.* 2014, 14, 2884-2889). Additionally, phosphorene has exhibited the highest known capacity for sodium ion storage (2596 mAh g$^{-1}$) and, unlike bulk silicon (Zhang S. *NPJ. Comput. Mater.* 2017, 3, 1-11), boasts a 2D material structure that enables robust stability over cycling durations at slow rates (Sun J et al. *Nat. Nanotechnol.* 2015, 10, 980-985; Dahbi M et al. *Chem. Mater.* 2016,28,1625-1635).

Herein, 2D black phosphorous nanosheets are exfoliated, assembled, and sodiated to produce a low-frequency energy harvester device. By combining equipotential Na$_x$P electrodes in a sandwich configuration, stress-induced migration of sodium ions resulting from ambient mechanical inputs, such as bending and pressing, at frequencies otherwise inaccessible by conventional piezoelectric materials (e.g., frequencies as low as 0.01 Hz) is demonstrated. The harvester is tested using both bending and pressing mechanical impulses with peak power delivery of ~42 nW/cm$^2$ and total harvested energy of 0.203 µJ/cm$^2$ in the bending mode and ~9 nW/cm$^2$ and 0.792 µJ/cm$^2$ in the pressing mode. These results demonstrate that 2D materials can be effectively leveraged as building blocks in strategies for efficient electrochemical strain energy harvesting, such as for high-performance human motion harvesters.

Figure 3:
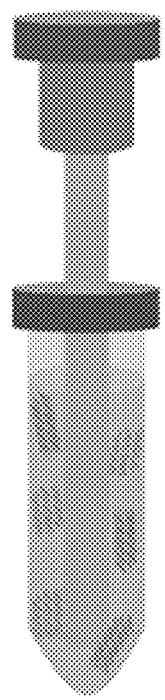
FIG. 3 is a schematic illustration of black phosphorous exfoliation in a 1-methyl-2-pyrrolidone (NMP) solution through tip sonication.
Figure 4:
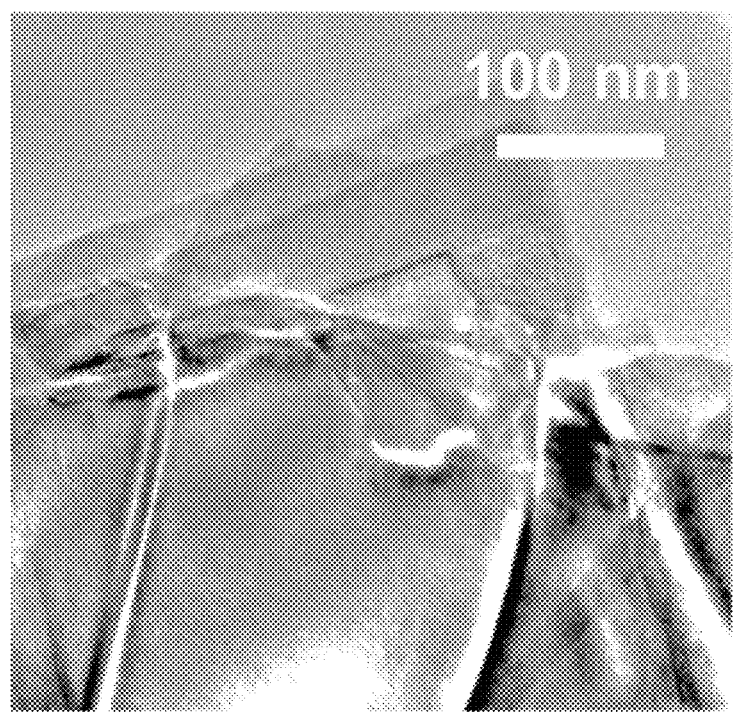
FIG. 4 is a low-magnification transmission electron microscopy (TEM) image of exfoliated black phosphorous nanosheets.
Figure 5:
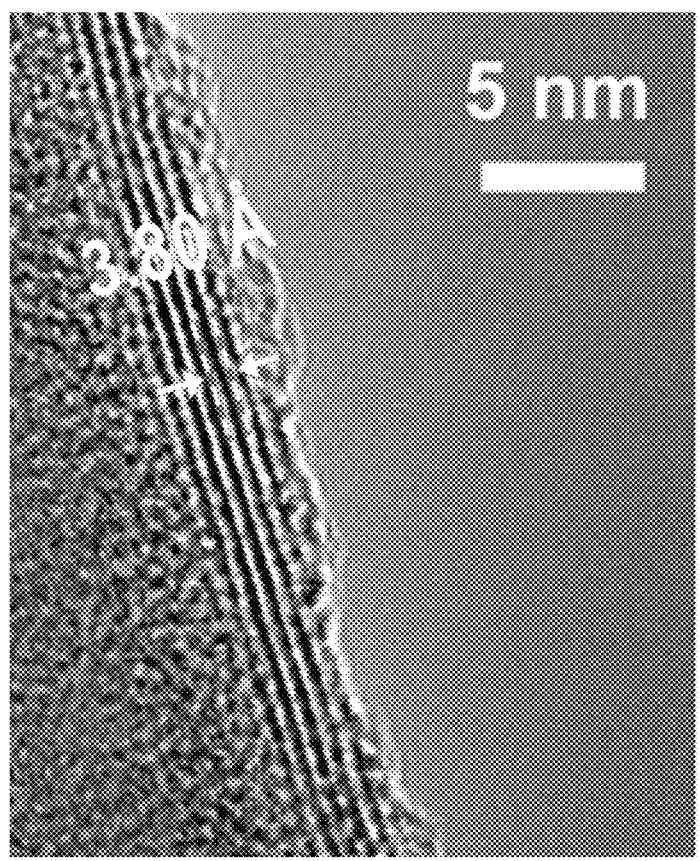
FIG. 5 is a high-magnification TEM image of exfoliated black phosphorous nanosheets.

To form electrodes to test as mechanochemical strain energy harvesters, nanosheets were exfoliated from black phosphorous in 1-methyl-2-pyrrolidone (NMP) solutions by using probe sonication (FIG. 3). Specifically, bulk black phosphorous (Smart Elements) was added to NMP (99.5%, Aldrich) solution with an initial concentration of 0.625 mg/mL. Black phosphorous exfoliation was assisted by a tapered-tip on a probe sonicator (Sonics, VCX750, 40% amplitude) with a 3 seconds on and a 3 seconds off pulse in ice bath for 5 hrs. The exfoliated solution was left overnight for further use. The morphology of exfoliated black phosphorous was characterized using a FEI Osiris TEM transmission electron microscope (TEM). Transmission electron microscope (TEM) images of the exfoliated 2D black phosphorous (FIG. 4, FIG. 5) show thin black phosphorous nanosheets generally between 3 and 20 atomic layers with a measured interlayer spacing of 3.80 Å.

Figure 6:
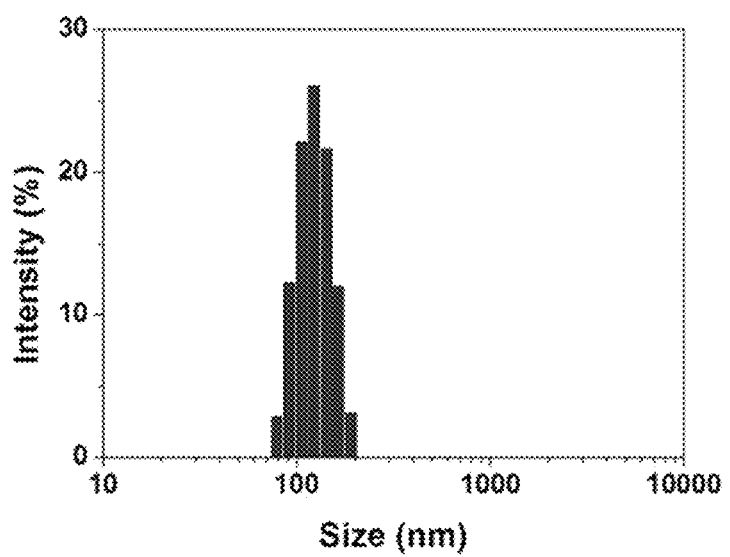
FIG. 6 is the hydrodynamic size distribution of exfoliated black phosphorous nanosheets measured by dynamic light scattering (DLS) technique on a Zetasizer.

Dynamic light scattering (DLS) was also used to characterize the exfoliated materials. Hydrodynamic size distribution data was collected using a Malvern Zetasizer using a dynamic light scattering (DLS) technique by measuring the rate of Brownian motion of the exfoliated black phosphorous suspended in NMP solution. The sub-micron size features in FIG. 6 confirmed the effective exfoliation of black phosphorous nanosheets into NMP solution. Zeta potential and particle size measurements were determined using a Malvern Zetasizer Nano ZS instrument. The zeta potential for the exfoliated black phosphorous solution was −56.7 mV, which dictates a negative surface charge of the exfoliated black phosphorous nanosheets.

To produce a bendable and electrically conducting interface for black phosphorous nanosheet coatings, few layered graphene was grown on thin copper foils (Strem Chemicals) using chemical vapor deposition (CVD) using C$_2$H$_2$ (0.3 sccm) as the precursor gas in an Ar (500 sccm) and H$_2$ (2 sccm) atmosphere at 1000° C. Copper foil with the CVD grown graphene was selected as the substrate for the deposition of black phosphorus.

Figure 7:
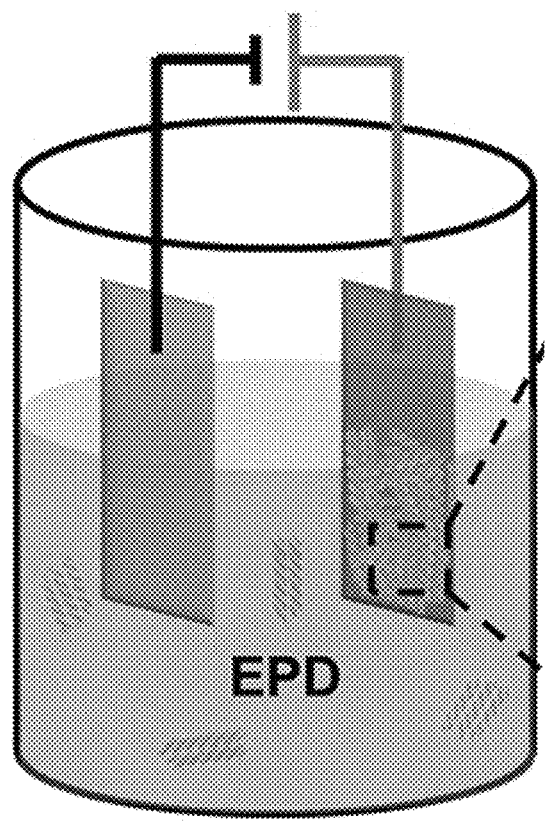
FIG. 7 is a schematic diagram of the electrophoretic deposition (EPD) setup.
Figure 8:
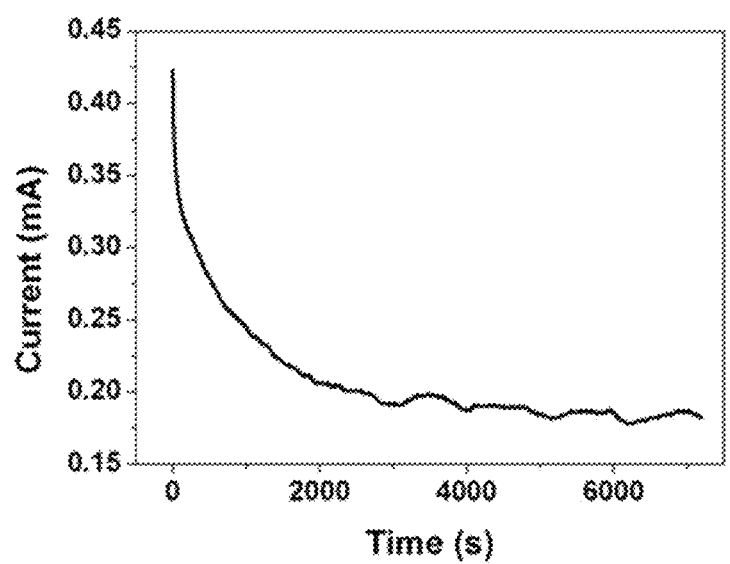
FIG. 8 is the I-t curve of electrophoretic deposition of exfoliated black phosphorous onto graphene on Cu under constant applied voltage (10 V for 2 hrs).
Figure 9:
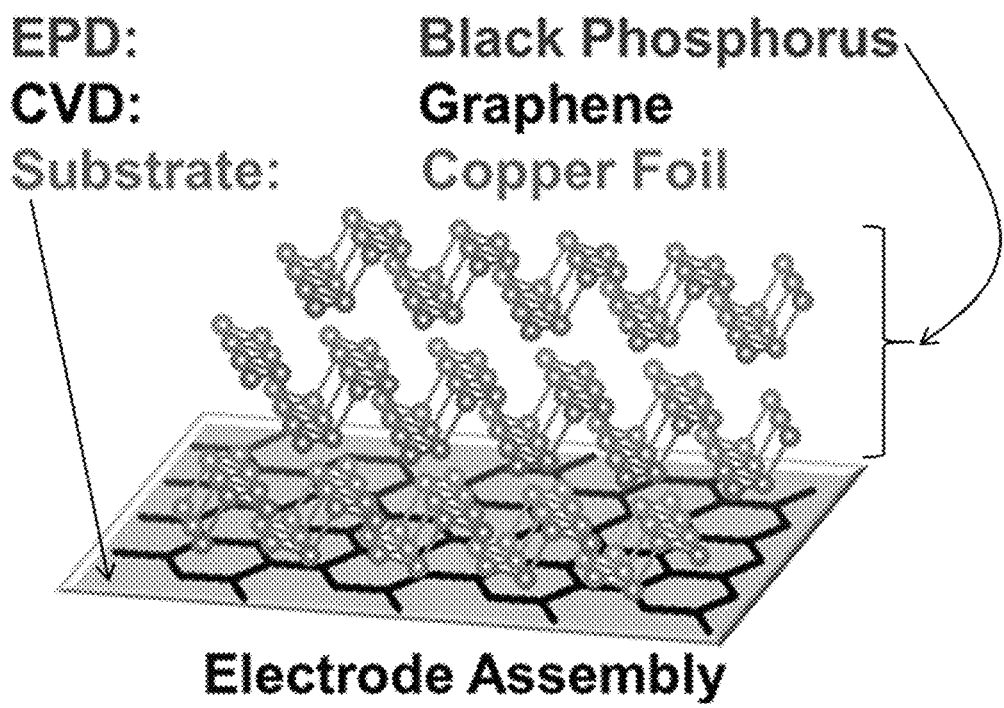
FIG. 9 is a schematic diagram of the electrode configuration.

To produce strain harvester electrodes from these 2D building blocks, electrophoretic deposition (EPD), was used (Oakes L et al. *J. Electrochem. Soc.* 2015, 162, D3063-D3070; Oakes L et al. *ACS Appl. Mater. Interfaces* 2015, 7, 14201-14210). Electrophoretic deposition (EPD) was performed using a Keithley 2400 Sourcemeter integrated with LabView data acquisition software at a constant voltage. Graphene on Cu foil with dimension of ~1.5 cm×3 cm was used as positive electrode, 316 stainless steel with same dimensions was used as counter electrode. The separation between the two electrodes was ~1 cm. Electrophoretic deposition was performed by applying a constant voltage (10 V) on the positive electrode (graphene/Cu) and counter electrode (stainless steel) that was immersed in exfoliated black phosphorous suspended in NMP (schematically represented in FIG. 7). Due to the negative surface charge of the black phosphorous nanosheets, the dispersed exfoliated black phosphorous preferably deposits onto the positive electrode (graphene/Cu) under an applied electric field. The corresponding deposition I-t curve is provided in FIG. 8. The resulting electrode was placed in a vacuum oven to dry overnight before further characterization and device assembly. FIG. 9 gives a schematic representation of the assembled black phosphorous nanosheets on the graphene/Cu substrate.

Figure 10:
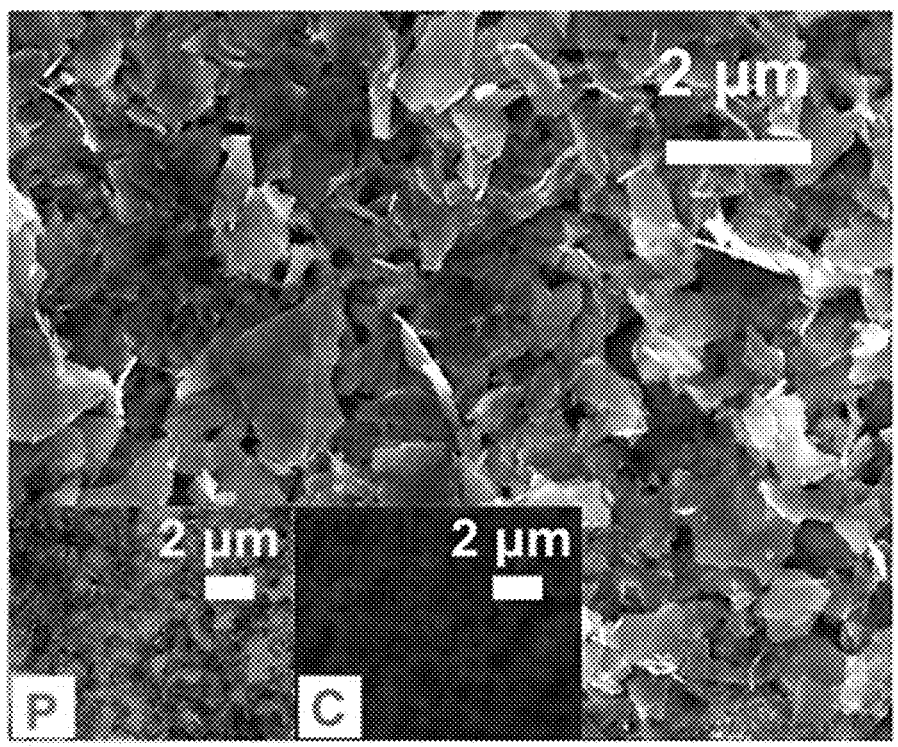
FIG. 10 is a scanning electron microscopy (SEM) image of the top-down view of deposited black phosphorous on graphene on Cu (with insets indicating SEM EDS elemental mappings of phosphorus and carbon).

The morphology of the black phosphorous deposited graphene/Cu electrodes were characterized using a Zeiss Merlin scanning electron microscope (SEM). Scanning electron microscopy (SEM) and corresponding elemental maps obtained from energy dispersive X-ray spectroscopy (FIG. 10) show effective assembly of exfoliated black phosphorous nanosheets on the graphene/Cu substrate. The mass of exfoliated black phosphorous deposited onto the positive electrode was measured as 0.95 mg/cm$^2$ for a 2 h deposition at a bias voltage of 10 V.

Figure 11:
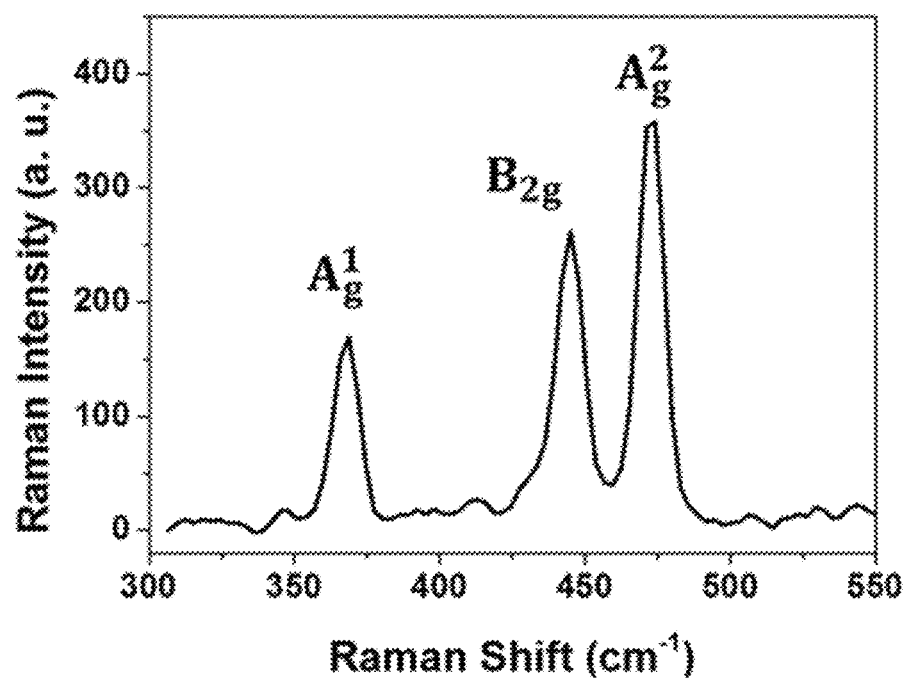
FIG. 11 is a Raman spectrum of the deposited black phosphorous.
Figure 12:
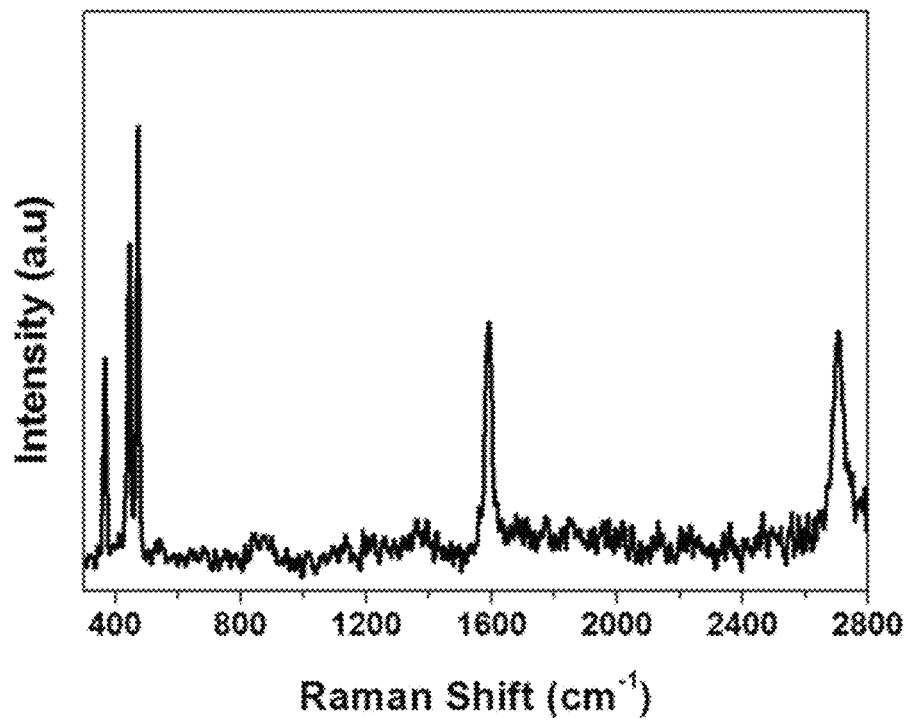
FIG. 12 is a Raman spectrum of the black phosphorous-G electrode.

Raman spectroscopy was carried out using a Renishaw in Via MicroRaman system with a 532 nm laser. Raman spectroscopy of the deposited black phosphorous on graphene/Cu (FIG. 11) shows the $A_g^1$, $B_{2g}$, and $A_g^2$ modes of black phosphorous (~367, 445, and 473 cm$^{-1}$, respectively) (Sun J et al. *Nat. Nanotechnol.* 2015, 10, 980-985). The complete Raman spectra of the black phosphorous-graphene (BP-G) electrode shows peaks corresponding to black phosphorus and graphene (FIG. 12).

For electrochemical characterization, the electrode was cut into ~0.7 cm×0.6 cm pieces, and then directly assembled into a CR2032 type coin cell inside an Argon-filled glovebox. Sodium metal (Aldrich) was used as counter electrode. 1 M NaClO$_4$ (≥98.0%, Aldrich) in ethylene carbonate (EC)/diethyl carbonate (DEC) (99%/>99%, Aldrich) with 1:1 volume ratio was used as the electrolyte with an additional 10 vol % 4-Fluoro-1,3-dioxolan-2-one (FEC, 98%, Alfa Aesar) as an additive. A Whatman grade GF/F glass fiber microfiber filter (Aldrich) was used as separator. Galvanostatic discharge was performed at a current density of 0.01 mA/cm$^2$ from open circuit voltage ($V_{OC}$) to 0.02 V.

Figure 13:
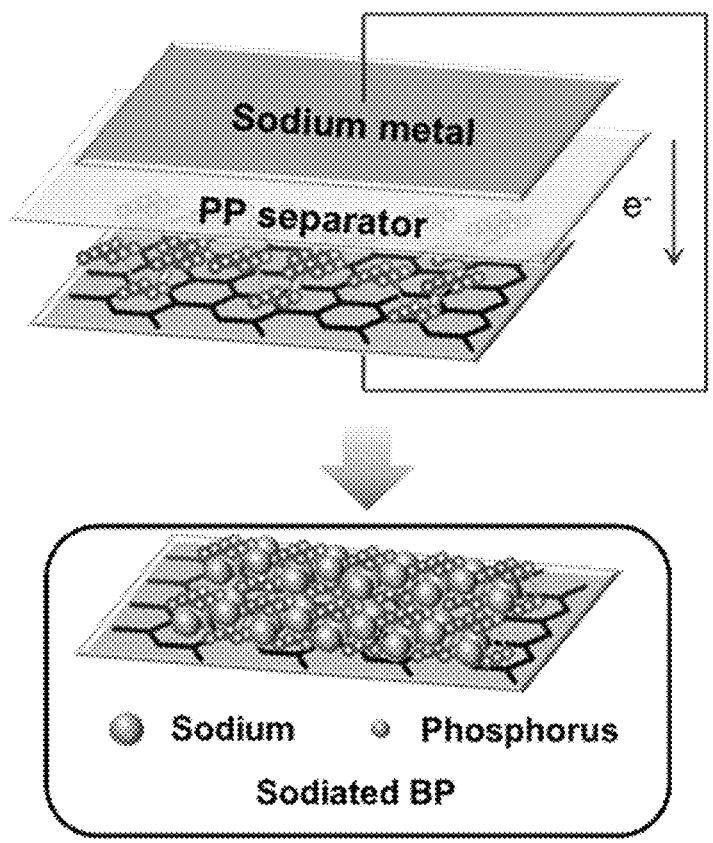
FIG. 13 is a schematic illustration of sodiation process and resulting sodiated black phosphorus electrode.
Figure 14:
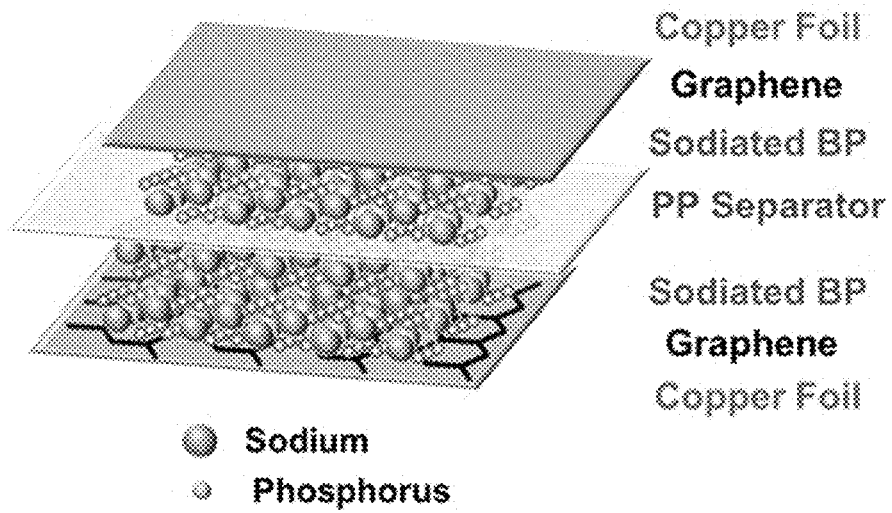
FIG. 14 is a schematic representation of the configuration of the black phosphorous mechanical energy harvester.

To produce an electrochemical-mechanical strain harvester, a black phosphorous nanosheet-coated graphene/Cu electrode was connected in short circuit mode against pure sodium metal (Aldrich) using the same electrolyte as mentioned to sodiate the black phosphorus for 4 hours (FIG. 13). The sodiated electrode was then cut into two halves which form the two electrodes of the energy harvester. The two electrodes were then assembled in a sandwich configuration with an electrolyte soaked polypropylene separator (Celgard 2500) was used as the separation between the two electrodes (FIG. 14). Kapton tape (Ted Pella) was used to encase the device thereby sealing the system from the external environment as well as creating an air tight configuration.

Figure 15:
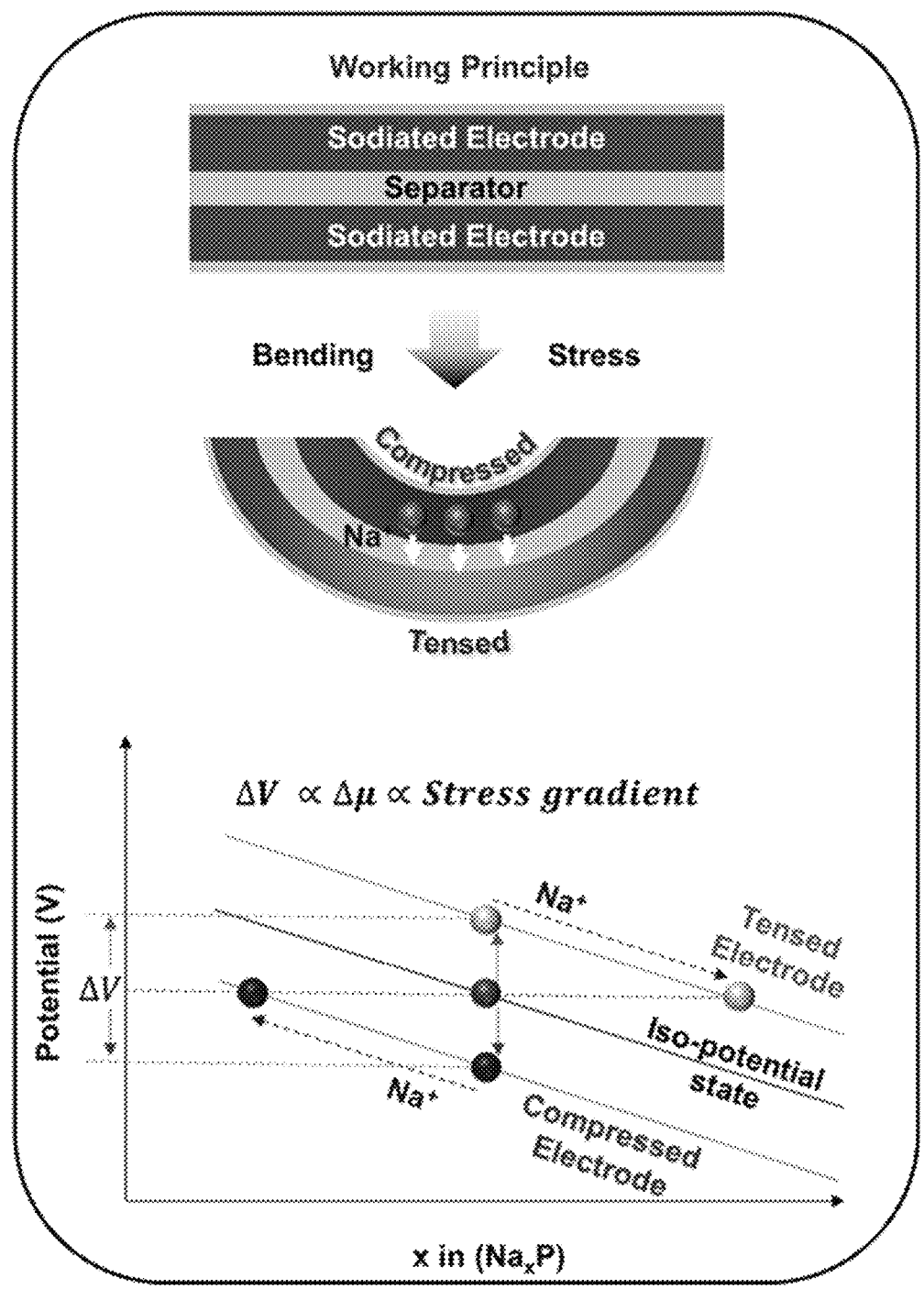
FIG. 15 is a schematic representation of the working principle of the black phosphorous energy harvester.

The device was then connected in short circuit mode using an external wire for 2 hours to homogenize the composition of both electrodes of the harvester and to reach an isopotential state between the two electrodes. As illustrated in FIG. 15, the device operates on the principle that bending or pressing induces a stress gradient between the two electrodes. Considering the scenario when the device is bent, the Na$_x$P electrode becomes compressed on one side, whereas the other electrode becomes tensed. These stresses are hence directly transmitted to the 2D building blocks making up the harvester. This generates a potential difference that originates from the different mechanochemical response of electrochemical systems under compressive or tensile stress (Muralidharan N et al. *Sci. Rep.* 2016, 6, 27542; Oakes L et al. *Nat. Commun.* 2016, 7, 11796; Muralidharan N et al. *ACS Nano* 2017, 11, 6243-6251). This mechanism generally holds true for pressing as well because the indentation in the material generated by pressing will lead to a strain gradient, albeit with smaller magnitude than bending motions. To reach an equilibrium potential on the electrodes, Na ions travel from the compressed region to the tensed region across the separator, which is accompanied by the flow of electrons in the external circuit, resulting in measured current flow. Here, the compressed electrode becomes the cathode, and the tensed electrode becomes the anode.

Figure 16:
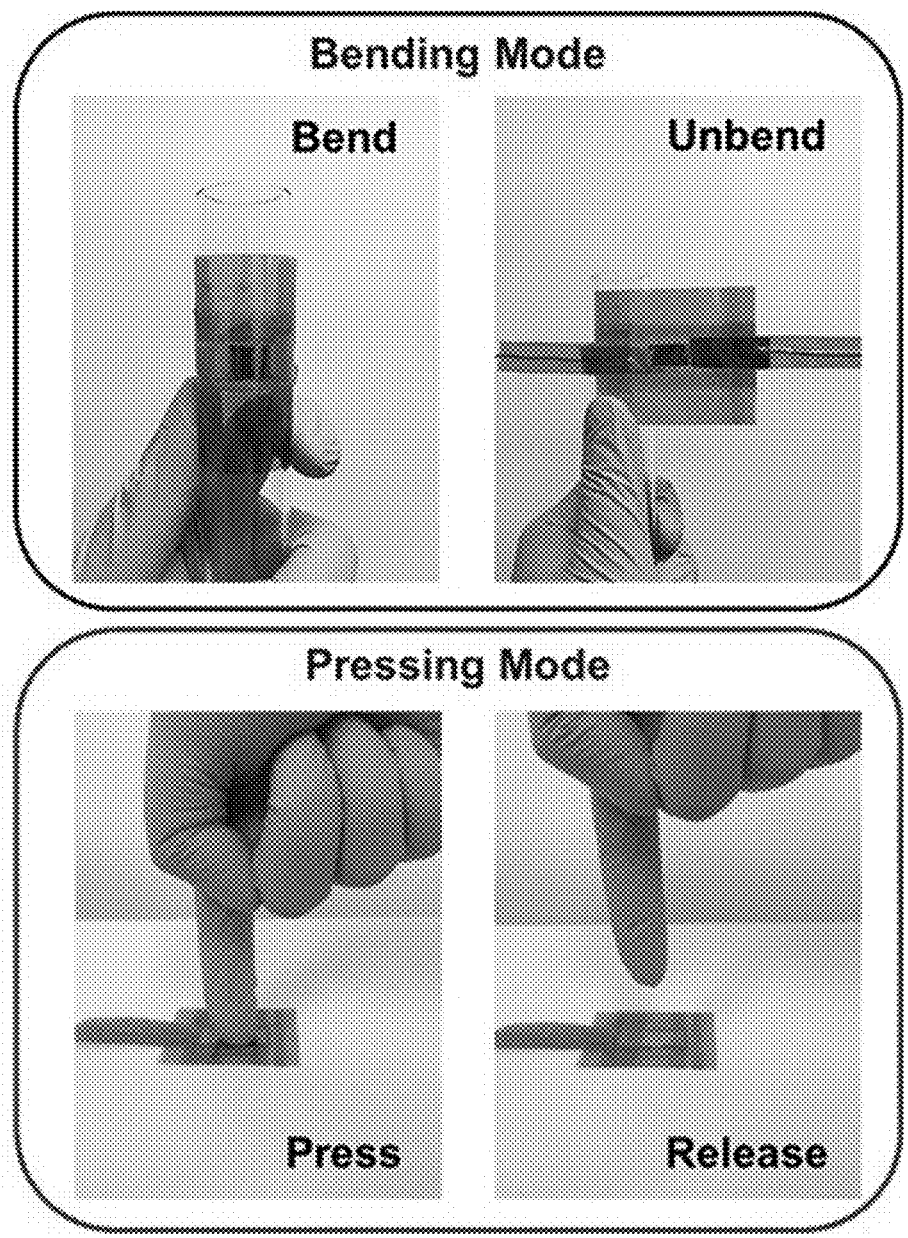
FIG. 16 shows representative images of bending and pressing tests performed on the developed energy harvester.
Figure 17:
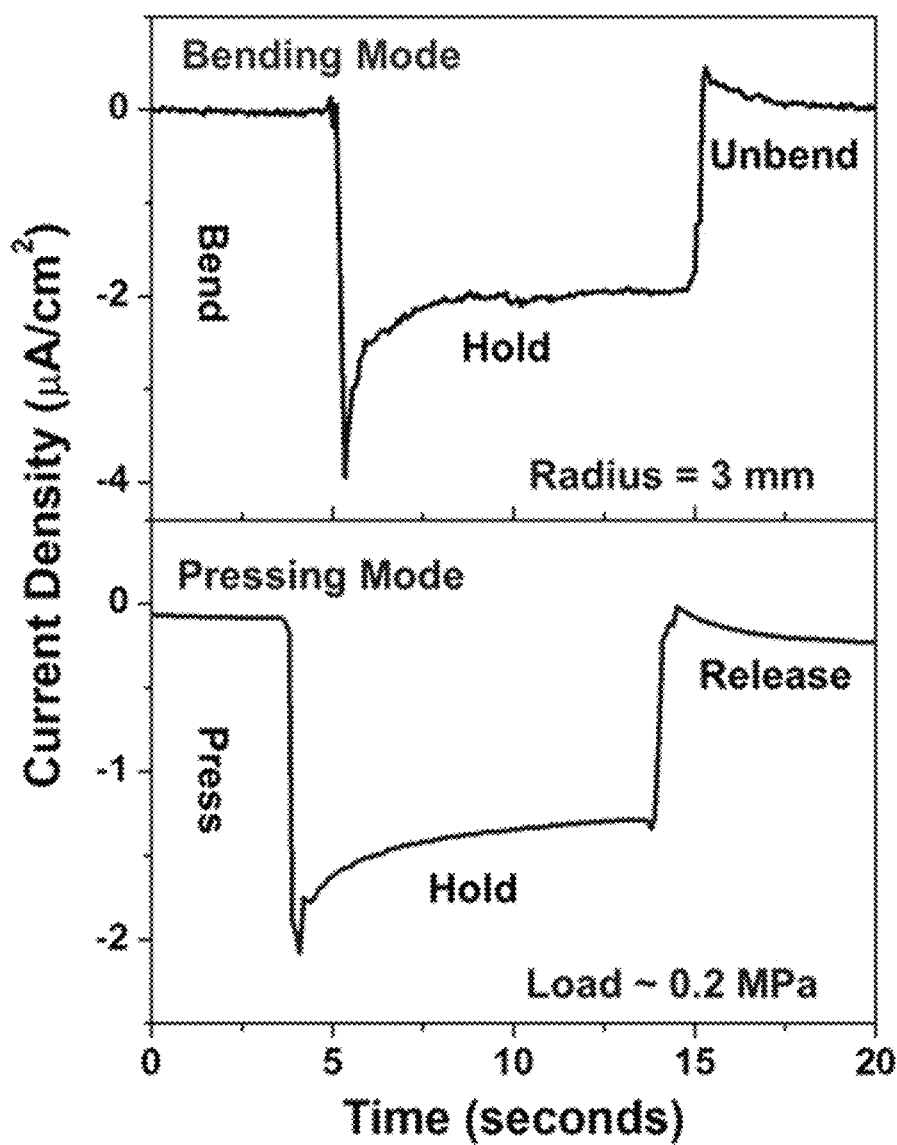
FIG. 17 shows the short-circuit current response of the energy harvester during bending (top) and pressing (bottom) modes.

Generally, unsteady background currents were observed during initial bending and unbending cycles, and this was resolved by treating the first few cycles as conditioning cycles. This could arise from effects such as small compositional inhomogeneity between the two electrodes or the formation of stable solid-electrolyte interface properties in electrodes under stress. Bending and pressing tests were conducted manually using hand bending around pipes of various diameters and pressing load determined using a weighing balance during testing. The current output of the device can be monitored using short-circuit current measurements from the device during the application of bending and pressing stresses (FIG. 16, FIG. 17). A sharp increase in current signal is observed in both cases followed by gradual decay of current. When the device is held under bending/pressing conditions (FIG. 17), the decay occurs due to relaxation of the stress gradient through alloying-induced stress of the migrating Na ion, resulting in gradual neutralization of the chemical potential gradient. The duration of ion migration matches the duration of the stress gradient imposed, and upon unbending or releasing the load on the device, the stress gradient vanishes, leading to cessation of ion flow and hence current generation. The full width at half-maximum (FWHM) value for the current response was ~10 s for both bending and pressing tests, which was considerably higher than that of traditional piezoelectric materials (~100 ms) (Kim S et al. *Nat. Commun.* 2016, 7, 10146; Qi Y and McAlpine M C. *Energy Environ. Sci.* 2010, 3, 1275-1285; Koka A et al. *Energy Environ. Sci.* 2014, 7, 288-296; Xu S et al. *Nat. Nanotechnol.* 2010, 5, 366-373; Hou Y et al. *Adv. Energy Mater.* 2017, 7, 1601983). Thus, this device can be utilized in harvesting ambient mechanical energy in the ultralow frequency regime (0.1-0.01 Hz). Notably, whereas this device exhibits performance that builds upon battery operation, the device is not inhibited by the same safety concerns as traditional battery systems. Because the harvester operates from an isopotential state, shorting the device will simply deactivate the harvesting capability of the device and not generate thermal runaway that leads to electrolyte ignition and battery fires.

Electrochemical-mechanical energy harvesters generate current through migration of charged ions. In the devices described herein, sodium ions from the compressed electrode move to the tensed electrode resulting in electric current generation. Even though the device described herein operates on the principles of battery electrochemistry, the potential safety issues which primarily affect batteries are negated in the current design framework. First, there is no free sodium metal in the energy harvester described herein as the sodium is either alloyed with the electrode material or exists in its ionic state in the electrolyte. This reduces any potential air stability issues associated with sodium metal. Second, the electrochemical-mechanical energy harvesters exhibit native strain harvesting function in an isopotential device state. Failure mechanisms in batteries can most commonly be attributed to short circuiting of the electrodes causing thermal runaway reactions that ignite the organic electrolyte and can cause explosion (Balakrishnan P G et al. *J. Power Sources* 2006, 155, 401-414; Wang Q S et al. *J. Power Sources* 2012, 208, 210-224). As the electrochemical-mechanical energy harvesters described herein have electrodes operating close to isopotential states, a short circuit event would simply deactivate the harvester from further device function without generating thermal runaway. Third, whereas the device described herein contains flammable organic solvents that can lead to safety concerns if intentionally exposed to a flame or other intense heat source above the flash point of the electrolyte, non-flammable solid-state electrolytes would render this system fully inert, and represents an area for further research efforts in electrochemical harvesters (Quartarone E and Mustarelli P. *Chem. Soc. Rev.* 2011, 40, 2525-2540). Further, better packaging can also minimize damage during mechanical deformation (Liu P et al. *J. Power Sources* 2009, 189, 646-650).

Figure 18:
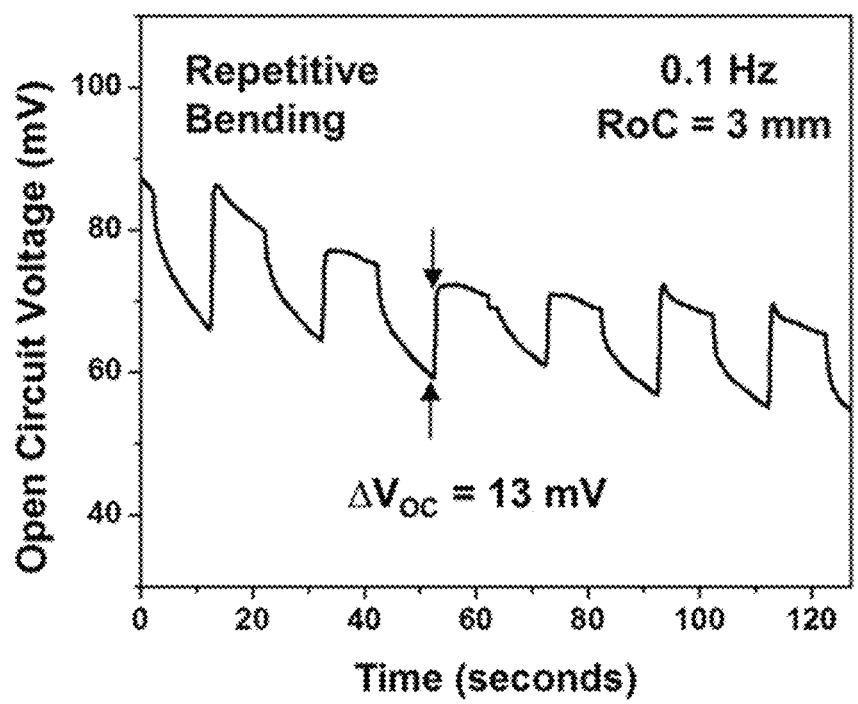
FIG. 18 is the open-circuit voltage response of the energy harvester during bending tests when bent at a radius of 3 mm at a frequency of 0.1 Hz.
Figure 19:
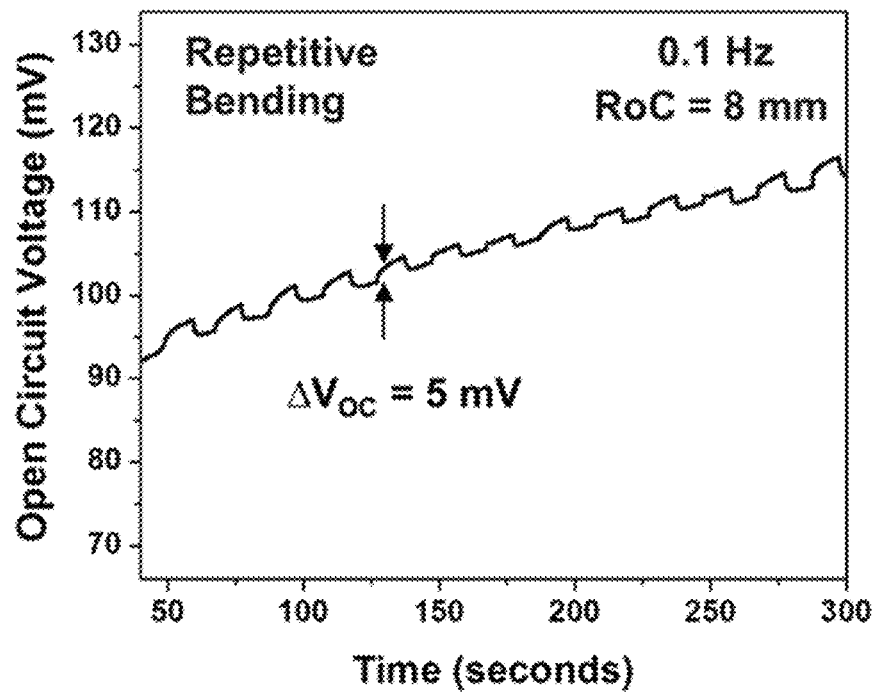
FIG. 19 is the open circuit voltage ($V_{OC}$) response of the energy harvester during repeated bending tests when bent at a radius of 8 mm at a frequency of 0.1 Hz.
Figure 20:
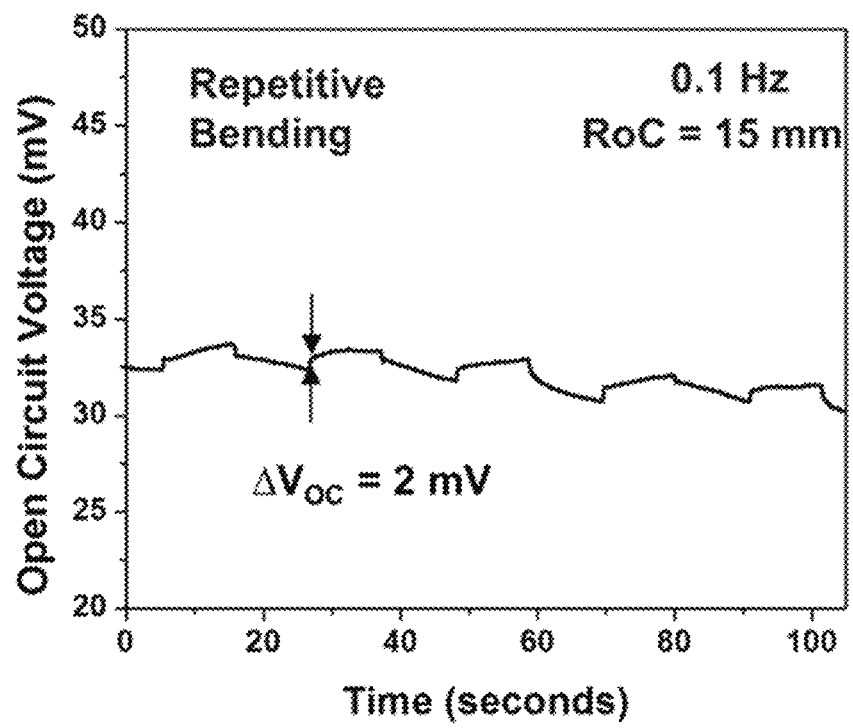
FIG. 20 is the open circuit voltage response of the energy harvester during repeated bending tests when bent at a radius of 15 mm at a frequency of 0.1 Hz.
Figure 21:
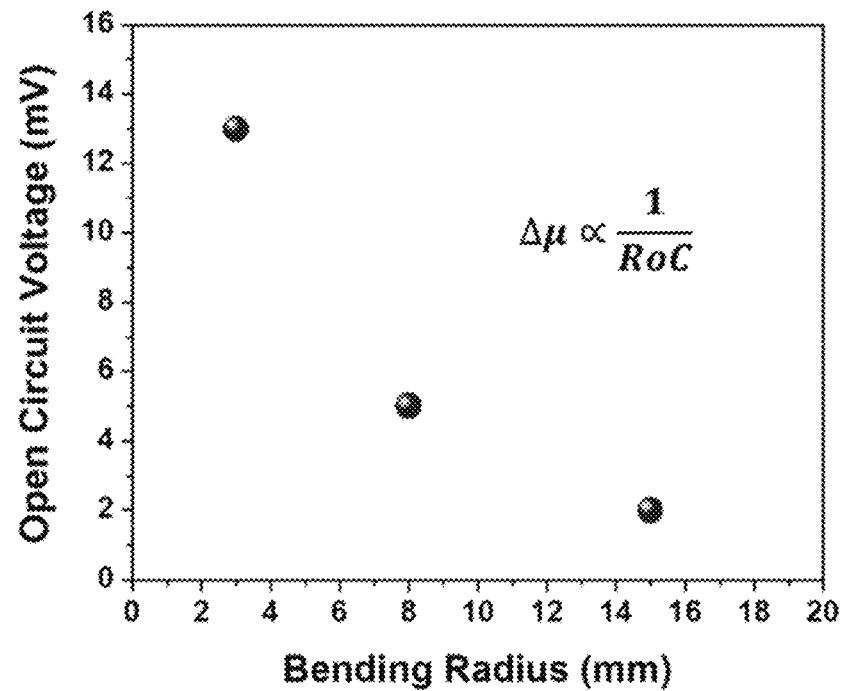
FIG. 21 shows the variation of $\Delta V_{OC}$ with bending radii for the energy harvesting device.

Repeated bending-unbending and pressing-releasing tests were performed on the device to assess repeatability of the electrical responses. Short circuit currents and open circuit voltages were determined during repeated bending and pressing tests using a portable Autolab PGSTAT 101 testing system. Open-circuit voltage measurements ($V_{OC}$) provide the maximum possible voltage outputs for a given stress condition in the absence of any current flow. FIG. 18 shows the $V_{OC}$ response of the device bent at a radius of curvature of 3 mm at a frequency of 0.1 Hz. When the bending stress is applied, the $V_{OC}$ increases to reach a maximum value that is maintained as long as the stress is applied. Upon unbending the device, the $V_{OC}$ recovers to its initial isopotential state. The nature of measuring $V_{OC}$ that does not explicitly involve Na ion migration to neutralize the mechanically induced stress gradient causes a gradual decrease of background potential as one electrode of the harvester is repeatedly placed under tension and the other is repeatedly under compression. The device was tested at different bending radii (FIG. 19 and FIG. 20), which shows an inverse dependence of the $V_{OC}$ on the bending radii (FIG. 21). The voltage (ΔV) generated is a function of the chemical potential gradient (Δμ) generated between the two electrodes. The chemical potential gradient between the two electrodes was inversely related to the radius of curvature (RoC) or the bending radius.

Figure 22:
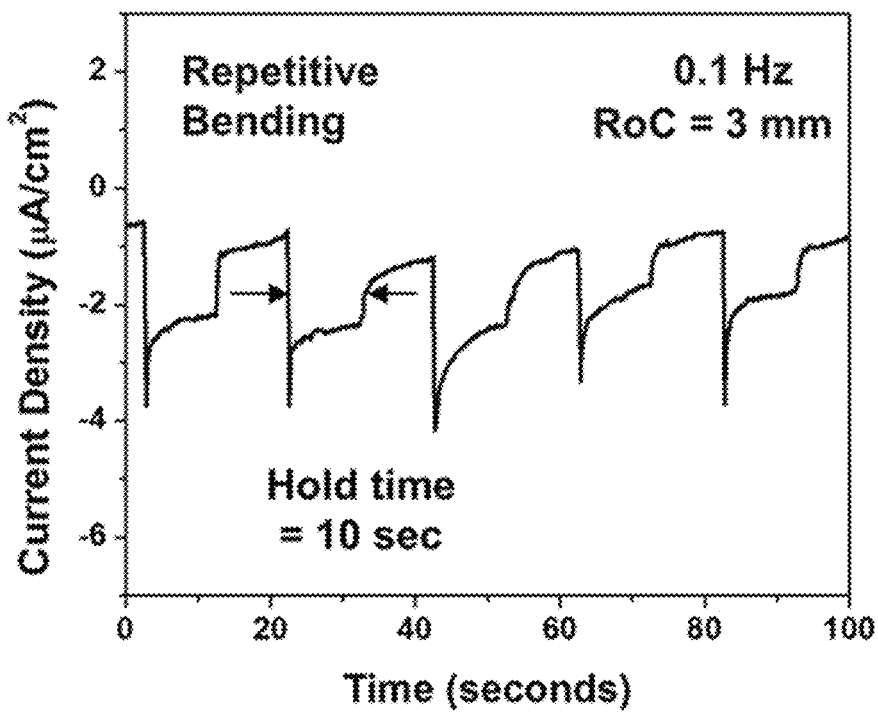
FIG. 22 is the short-circuit current response of the energy harvester during bending tests when bent at a radius of 3 mm at a frequency of 0.1 Hz.
Figure 23:
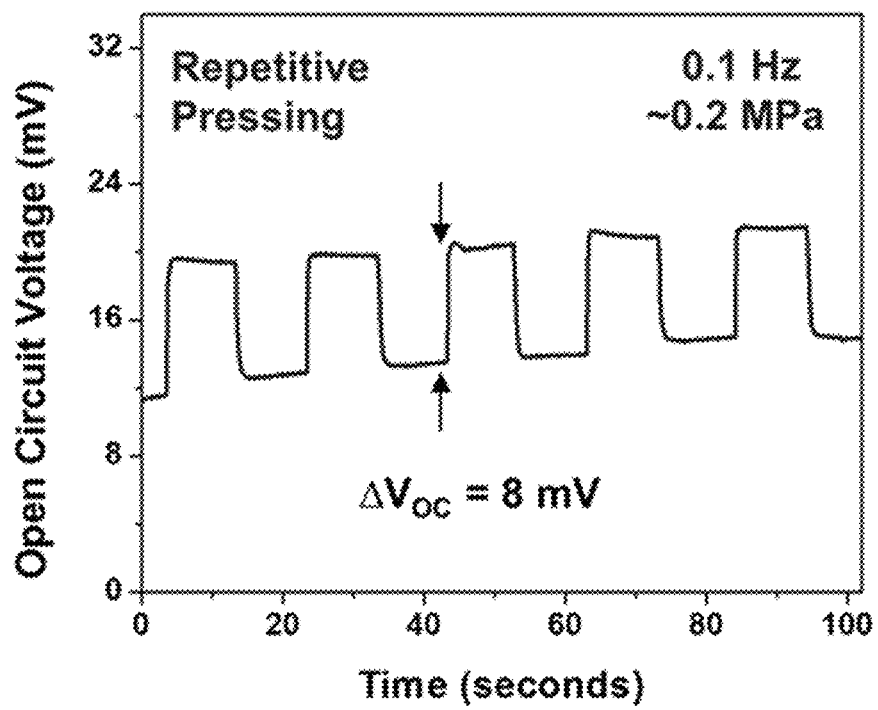
FIG. 23 is the open-circuit voltage response of the energy harvester during pressing tests with an applied load of ~0.2 MPa at a frequency of 0.1 Hz.
Figure 24:
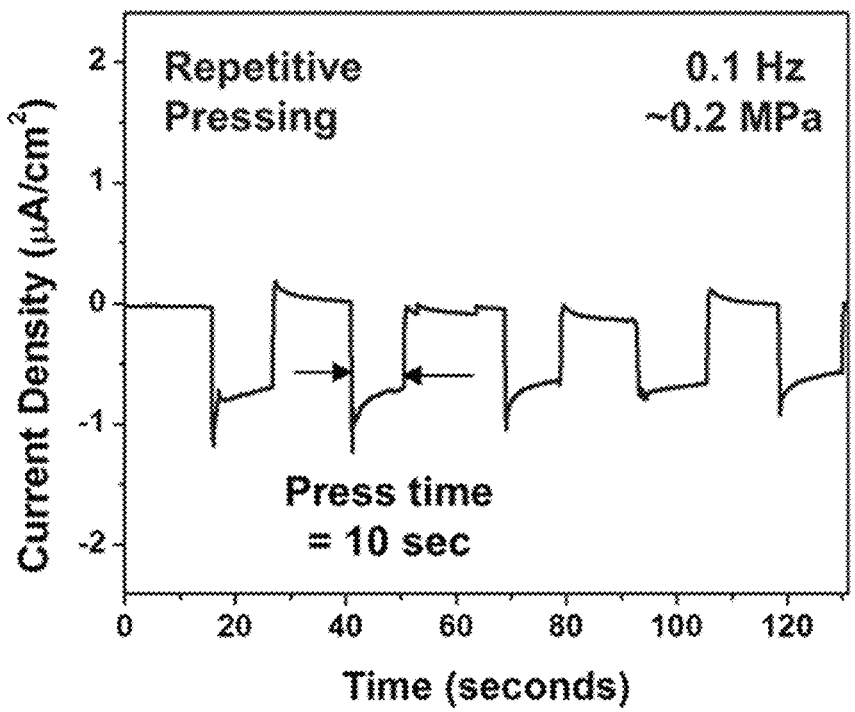
FIG. 24 is the short-circuit current response of the energy harvester during pressing tests with an applied load of ~0.2 MPa at a frequency of 0.1 Hz.
Figure 25:
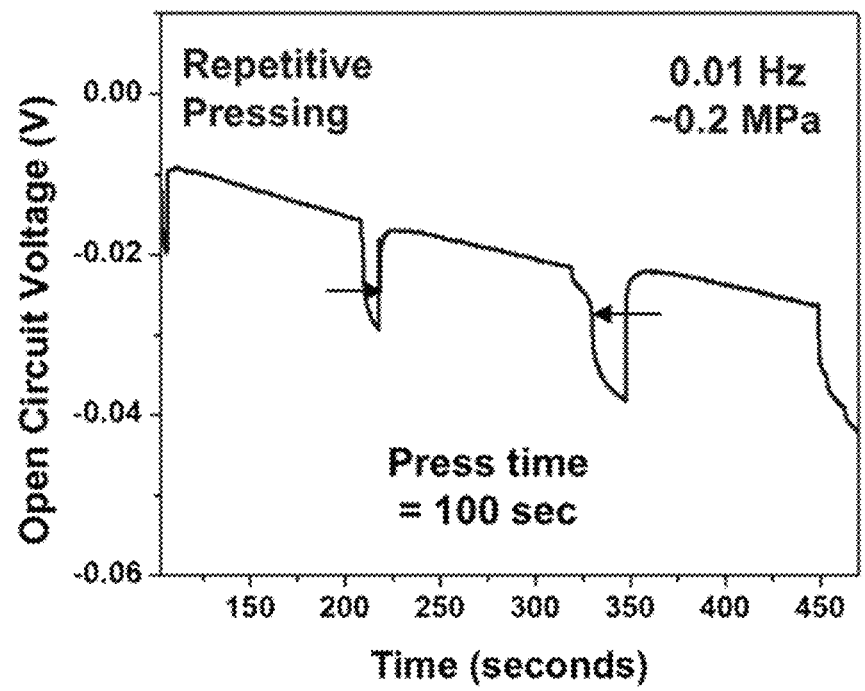
FIG. 25 is the open circuit voltage response of the energy harvester during repeated pressing tests with applied load of ~0.2 MPa at a frequency of 0.01 Hz.
Figure 26:
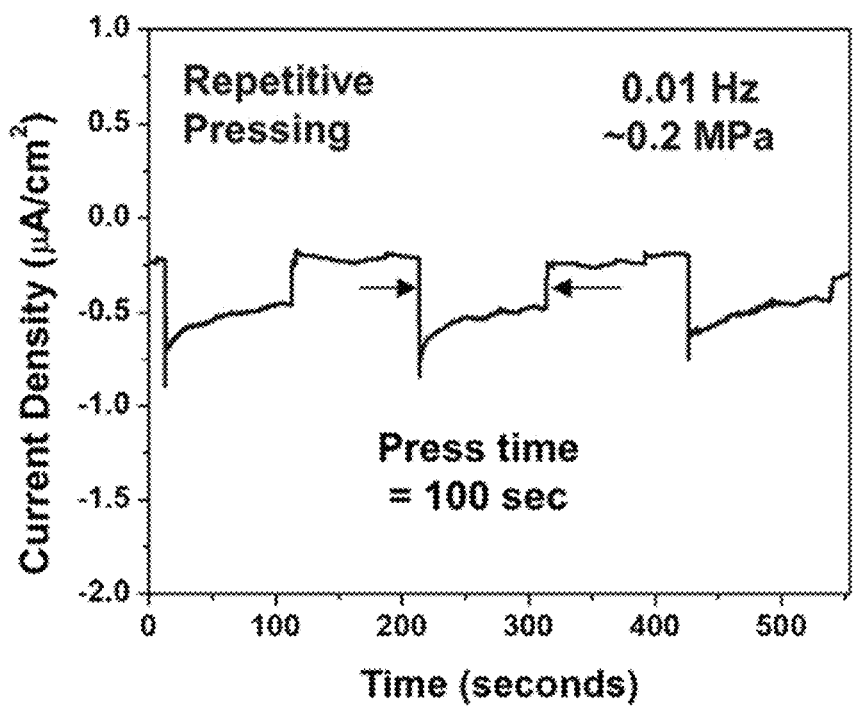
FIG. 26 is the short circuit current response of the energy harvester during repeated pressing tests with applied load of ~0.2 MPa at a frequency of 0.01 Hz.

FIG. 22 shows the short-circuit current measurements during repeated bending-unbending tests at a frequency of 0.1 Hz. Large bending radii result in lower applied stress/strain, leading to a lower chemical potential gradient and lower current flow. FIG. 23 and FIG. 24 shows the $V_{OC}$ and short-circuit current responses during repeated pressing and releasing tests at frequencies of 0.1 Hz. Similar to the bending response, pressing the electrodes sets up chemical potential gradients correlated to the open-circuit and short-circuit current response from the device. Pressing tests were performed by application of static loads (~0.2 MPa) held for various time periods (10 s and 100 s). Repeated pressing tests were performed at very low frequencies of 0.01 Hz, corresponding to a 100 s hold time (FIG. 25 and FIG. 26). At very low frequencies of 0.01 Hz corresponding to a 100 second hold time, the energy harvester generates comparable voltage and currents in the open circuit and short circuit mode respectively. The FWHM at 0.01 Hz is ~100 seconds indicating the applicability of this device in the regime of very low frequencies which are inaccessible to conventional piezoelectric materials.

Figure 27:
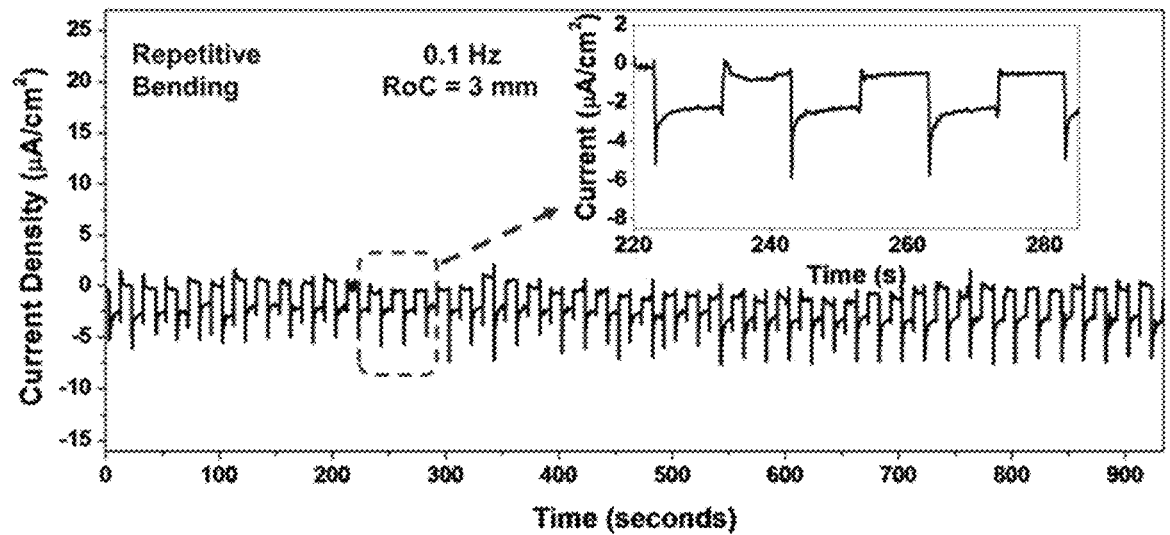
FIG. 27 shows the cycling response of the energy harvester during repeated bending tests when bent at a radius of 3 mm at a frequency of 0.1 Hz.

During pressing tests, the response time of these devices can be varied from 10 s to 100 s depending on the hold time, providing a framework for harvesting electrical energy from static load conditions. To demonstrate the stability of the device response over long cycling duration, repetitive bending experiments carried out with 50 cycles at a 0.1 Hz frequency and bending radius of 3 mm (FIG. 27). Over the course of long-term cycling experiments, no significant degradation in the mechanochemical response associated with the strain harvester operation was observed.

Unlike piezoelectric energy harvesters that generate maximum power and energy when operating at resonant frequencies of the active materials, the device described herein operates at low frequencies where the performance metrics are dictated by the diffusion characteristics of the sodium ions in the active material, electrolyte, and separator. The peak power and energy during bending tests (Table 1) at 0.1 Hz for a bending radius of 3 mm were determined to be 42 nW/cm$^2$ and 0.203 μJ/cm$^2$, respectively. For pressing tests (Table 1) at 0.01 Hz under a small loading of ~0.2 MPa, the peak power and energy were determined to be ~9 nW/cm$^2$ and 0.792 μJ/cm$^2$, respectively. The peak power and energy obtained significantly exceed the values obtained from state-of-the-art piezoelectric materials that exhibit drastically reduced harvesting performance at low operating frequencies.

TABLE 1

Performance of the phosphorene 2D energy harvester.

| Testing Method | Operational Frequency (Hz) | Bending radius (mm) | Applied Pressure (MPa) | Peak Power (nW/cm$^2$) | Energy Harvested (μJ/cm$^2$) | Response time (s) |
|---|---|---|---|---|---|---|
| Bending | 0.1 | 3 | — | 42 | 0.203 | 5 |
| Pressing | 0.1 | — | ~0.2 | 9.68 | 0.76 | 10 |
|  | 0.01 | — | ~0.2 | 9.12 | 0.792 | 100 |

Figure 28:
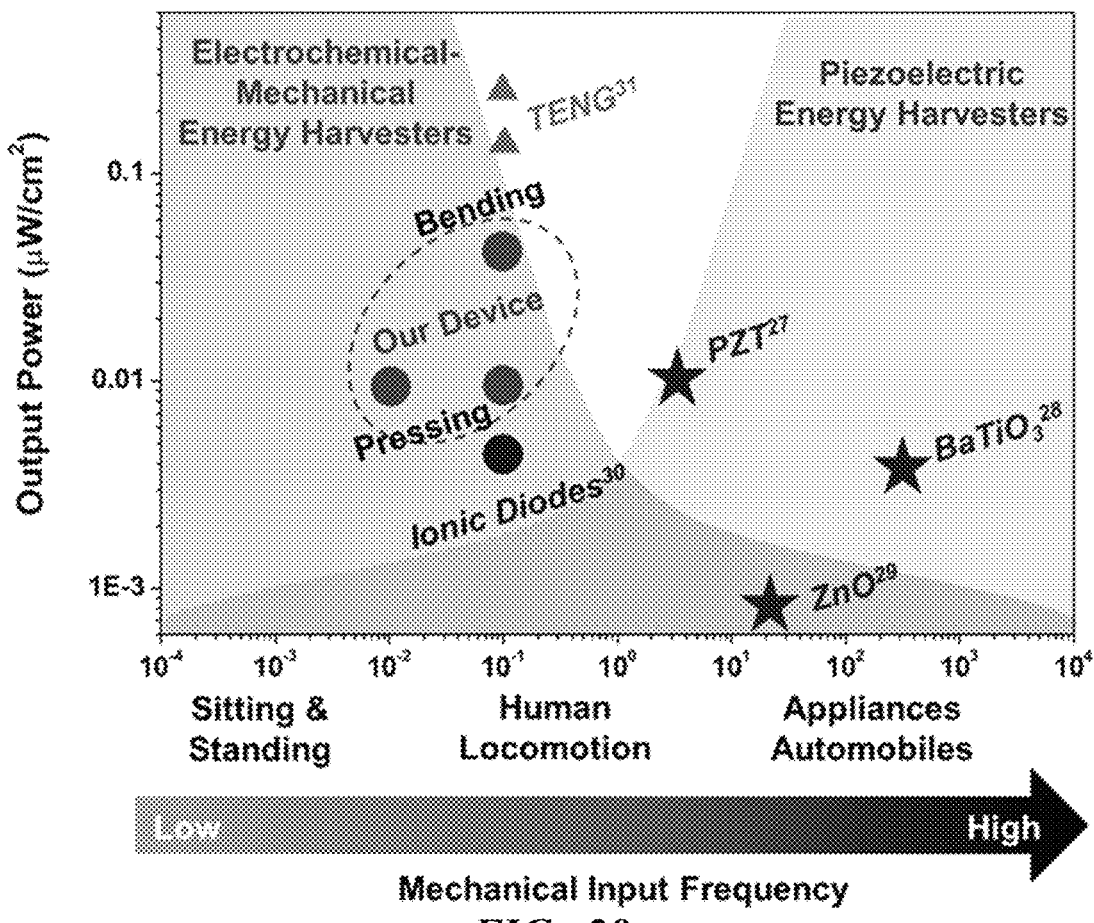
FIG. 28 is a frequency-dependent performance plot comparing the 2D black phosphorous energy harvester using nanoscale black phosphorous building blocks to other types of devices described in the literature. Shaded regions indicate the fall-off of energy harvesting capability at low frequencies outside of the range of traditional harvesting routes (left) and at high frequencies outside of the range of electrochemical harvesters (right). Human gait is described fully by motions with frequency under 5 Hz, where traditional efficiency of traditional harvesting schemes falls off, as represented by the gray shaded region.

Compared to other energy harvesting schemes (FIG. 28), the black phosphorous nanosheet energy harvester exhibits higher peak power performance than piezoelectrics with operation in frequency ranges directly overlapped with human motion (Qi Y and McAlpine M C. Energy Environ. Sci. 2010, 3, 1275-1285; Koka A et al. Energy Environ. Sci. 2014, 7, 288-296; Xu S et al. Nat. Nanotechnol. 2010, 5, 366-373; Hou Y et al. Adv. Energy Mater. 2017, 7, 1601983; Zi Y et al. ACS Nano 2016, 10, 4797-805). Whereas piezoelectrics natively exhibit low conversion efficiency in frequency ranges of optimized energy conversion, harvesting energy from human motions at <5 Hz leads to significantly lower conversion efficiency. For example, a 1% piezoelectric harvester with an operation frequency of 100 Hz can lead to as little as 0.01% efficient operation at 1 Hz. In this way, the shading of the panel in FIG. 28 indicates the drop-off of efficiency of traditional mechanical energy harvesters due to the mismatch of the operation frequency and the frequency of human motions. Similarly, the electro-chemical-mechanical harvesters exhibit a drop-off of performance at high frequencies due to the mechanical-chemical response that is correlated with ion diffusion processes in the electrodes. This implies that (1) broad-band energy harvesting can be achieved by combinations of traditional harvesters with low-frequency electrochemical harvesters and (2) electrochemical harvesters are well-suited for the conversion of energy associated with human gait into usable electric energy unlike traditional energy harvesting routes. Nonetheless, one challenge in this electrochemical-mechanical system is the low voltage distribution of harvested charge. Whereas research into this class of energy harvesters is presently at its infancy, strategies to improve voltage output could involve (i) the use of larger size ions (K+, Rb+, and Cs+) as these ions have large partial molar volume leading to greater potential differences and (ii) using ion hosts that have high yield strength because the greater the yield strength, the greater the voltage output. Other approaches could employ these electrochemical harvesters in series configurations or the use of power electronics, such as buck converters, to shape the voltage output for a desired application.

The idealized efficiency is obtained from the theoretical constructs provided by S. Kim et al. (Kim S et al. Nat. Commun. 2016, 7, 10146). Bending the device leads to one electrode being compressively strained and the other being tensile strained corresponding to the state $\varepsilon_{xx}=\pm h/RoC$, where RoC is the radius of curvature and h is one half the thickness of the whole device. The stress on one electrode can be written as, $$\sigma_{xx} = \frac{Eh}{(1-\vartheta^2)(RoC)}$$
$$\sigma_{zz} = \frac{\vartheta Eh}{(1-\vartheta^2)(RoC)}$$
$$\sigma_{yy} = 0 \quad (1)$$

$\sigma_{yy}=0$ owing to assumption of a plane stress condition in the y direction. E is the Young's modulus of the electrode and $\vartheta$ is the Poisson's ratio. For materials such as sodiated phosphorous assuming the $Na_3P$ phase, the Poisson's ratio is generally assumed to be ~0.25. The strain energy generated in the system can be coupled into hydrostatic and deviatoric components where, $$U_{Strain} = U_{Hydrostatic} + U_{Deviatoric} = \frac{E}{2(1-\vartheta^2)}\left(\frac{h}{RoC}\right)^2 \quad (2)$$

$$U_{Hydrostatic} = \frac{\sigma_{Hydrostatic}^2}{2B}, \text{ where } B = \frac{E}{3(1-2\vartheta)} \quad (3)$$

B is the Bulk modulus of the electrode. Assuming only hydrostatic components contribute to energy generation and all of the deviatoric components are wasted, the idealized efficiency is $$\eta = \frac{U_{Electrical}}{U_{Strain}} = \frac{U_{Hydrostatic}}{U_{Strain}} = \frac{(1-2\vartheta)(1+\vartheta)}{3(1-\vartheta)} \quad (4)$$

Figure 29:
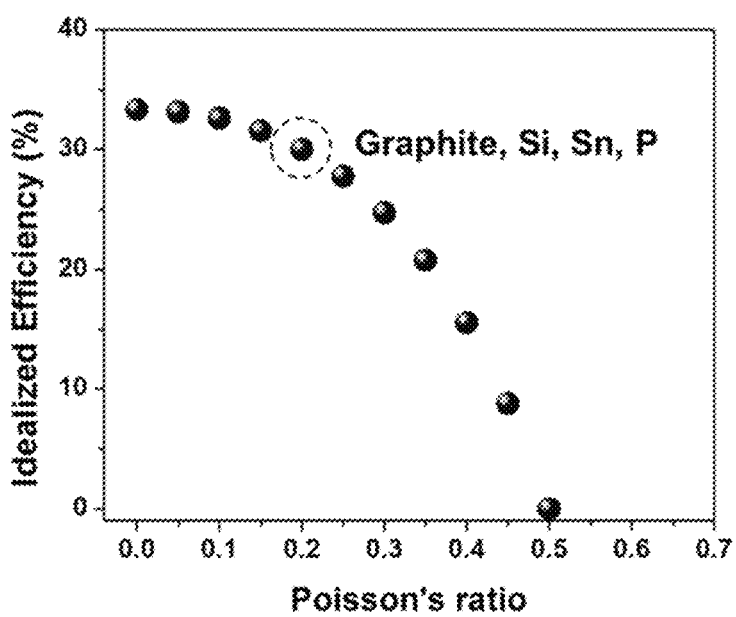
FIG. 29 shows the idealized efficiency of the electrochemically driven energy harvesters.

The above equation dictates that the efficiency of the device is a function of the Poisson's ratio. Considering a Poisson's ratio of 0.25, the idealized efficiency is about 27.8%. The efficiency maxes out at a Poisson's ratio of 0 to be 33.3%. The theoretical mechanical-to-electrical conversion efficiency in the system describes herein can be >30% (FIG. 29).

The results presented herein introduce the use of 2D nanostructures for electrochemical strain energy harvesting, which provides exciting pathways for future research directions. At the system level, control of assembly of the nanostructured building blocks can be a critical factor to enable efficient coupling of mechanical energy to electrical energy. At the nanoscale, a new class of strain harvesters that can be assembled at the single-nanosheet scale. An example is a stacked 2D material with locally intercalated ions that can function as a nanoscale strain harvesting device for low-frequency motions at the molecular scale in fabrics, liquids, or other media (Oakes L et al. *Nat. Commun.* 2016, 7, 11796; Sun J et al. *Nat. Nanotechnol.* 2015, 10, 980-985; Cohn A P et al. *Nano Lett.* 2016, 16, 543-548). This work emphasizes how 2D building blocks can be platforms for the design of future strain energy harvesting schemes tuned to harvest energy from low-frequency motions.

In summary, this work demonstrates a 2D material (phosphorene) strain energy harvester configuration relying on mechanoelectrochemical stress-voltage coupling at low frequencies relevant to human motions. The assembled harvester was tested in both bending and pressing modes, with experiments demonstrating peak power deliveries of ~42 $nW/cm^2$ (0.1 Hz, RoC=3 mm) and ~9 $nW/cm^2$ (0.1/0.1 Hz, Load 0.2 MPa), respectively. The energy outputs from these devices during bending and pressing were 0.203 $\mu J/cm^2$ (0.1 Hz, RoC=3 mm) and 0.792 $\mu J/cm^2$ (0.01 Hz, Load 0.2 MPa), respectively, with response times (fwhm of current output=10 s and 100 s) several orders of magnitude greater than those of conventional piezoelectric systems that provide highly inefficient harvesting capability at such low frequencies. This provides a framework to exploit (i) the controlled mechanical properties of 2D materials, (ii) the homogeneous strain propagation that occurs in 2D material geometries, and (iii) the capability of accessing 2D material energy harvesting tuned to frequencies relevant to human motions. These results support future work spanning from harvesting mechanical stresses at the nanometer length scales in designer 2D material stacks to designing system-level architectures, such as integrated MEMS-electrochemical harvesting units that can be functional for a broad range of low-frequency energy harvesting applications complementary to the state-of-the-art piezoelectric or triboelectric system operation.

Example 2

Described herein is a device that converts mechanical forces at frequencies associated with human motions (generally <5 Hz) into an electrical signal for energy harvesting and/or sensing purposes. The device can achieve this by using ion-intercalated electrodes comprising two dimensional materials, which can comprise a high ion species content.

The devices described herein can overcome the limitations of conventional energy harvesting systems at low frequencies associated with human motions. Piezoelectrics, which operate based on the piezo effect, are tuned for frequencies typically in the range of 100 Hz and greater. Human motions generally occur at frequencies of <5 Hz.

The devices described herein can comprise ultrathin graphite grown on Ni foils cointercalated (e.g., intercalated with Na species having glyme solvent shell intact) and combined in a similar configuration as in Example 1. Higher peak currents and voltages are observed, and devices are demonstrated to show clear current response to human motion when places on a knee during walking.

Figure 30:
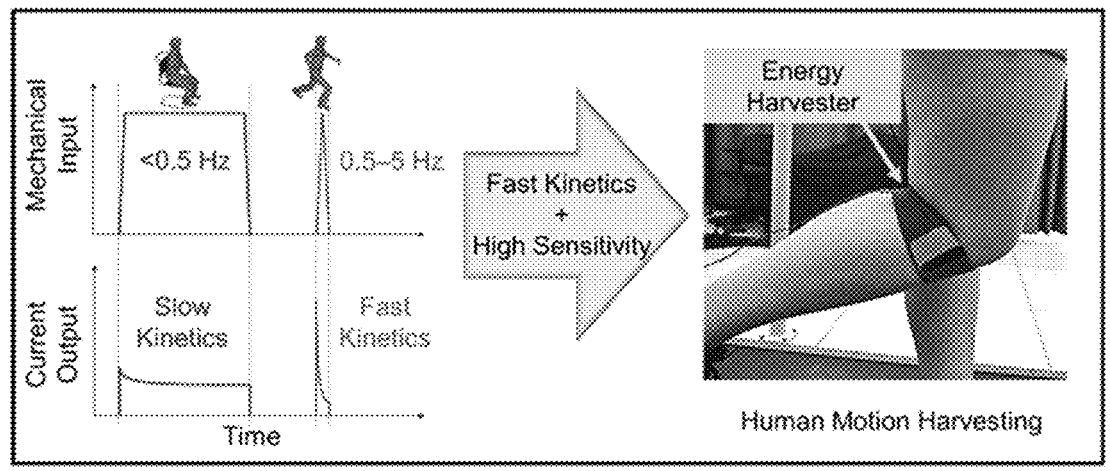
FIG. 30 shows the frequency compatibility of the mechano-electrochemical energy harvesters for human motion harvesting.

FIG. 30 shows the frequency compatibility of the mechano-electrochemical energy harvesters for human motion harvesting.

Figure 31:
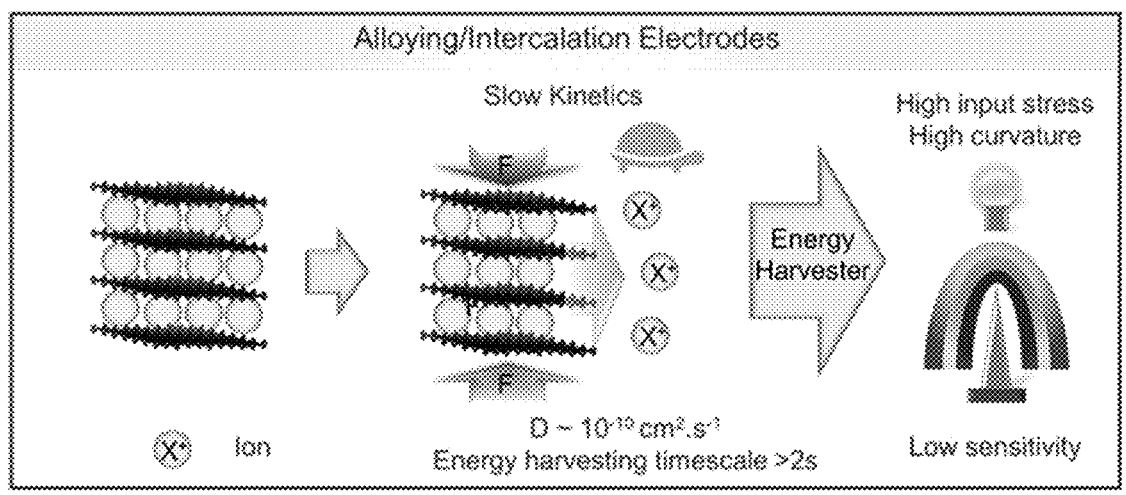
FIG. 31 shows the mechano-electrochemical characteristics of conventional alloying/intercalation electrodes.

FIG. 31 shows the mechano-electrochemical characteristics of conventional alloying/intercalation electrodes.

Figure 32:
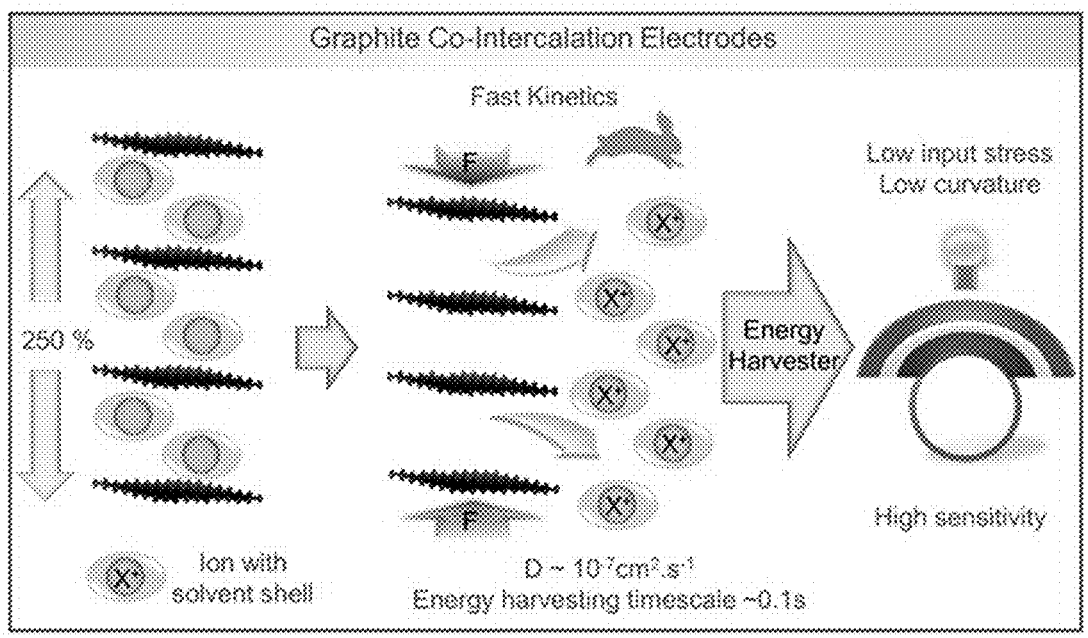
FIG. 32 shows the mechano-electrochemical characteristics of graphite co-intercalation electrodes.

FIG. 32 shows the mechano-electrochemical characteristics of graphite co-intercalation electrodes.

Figure 33:
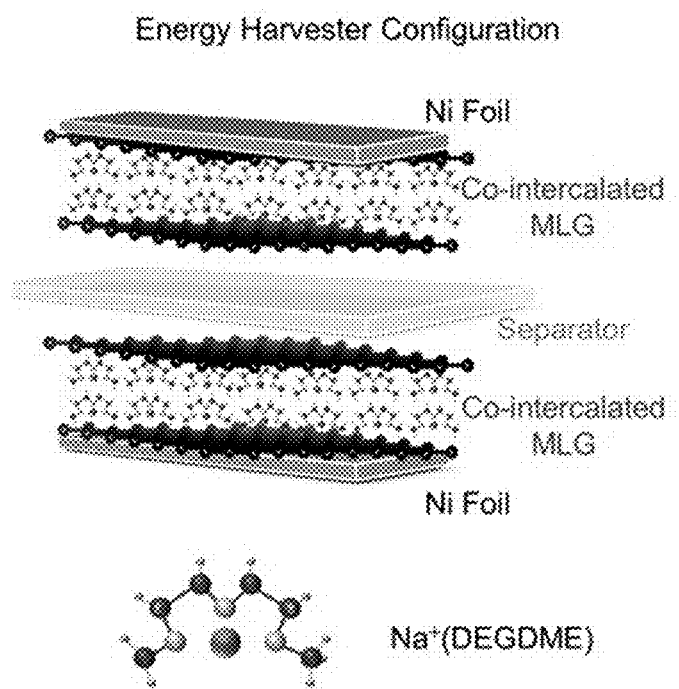
FIG. 33 shows configuration of the graphite co-intercalation energy harvester.

FIG. 33 shows configuration of the graphite co-intercalation energy harvester.

Figure 34:
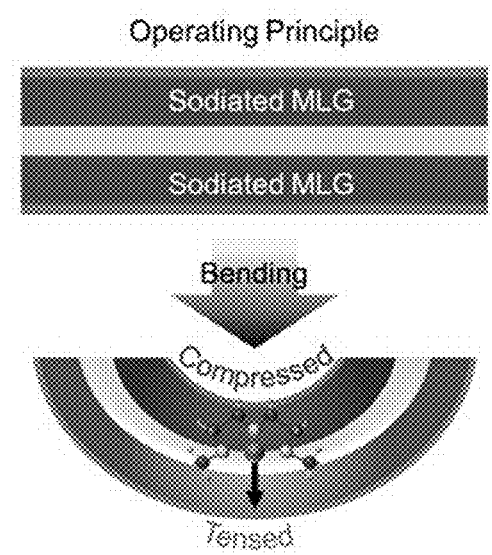
FIG. 34 shows operational mechanics of the graphite co-intercalation energy harvester.

FIG. 34 shows operational mechanics of the graphite co-intercalation energy harvester.

Figure 35:
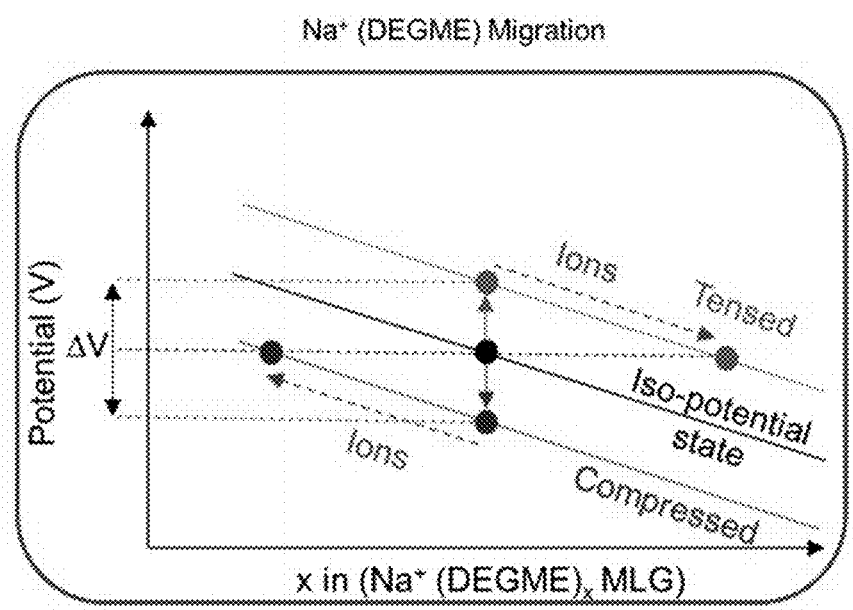
FIG. 35 shows operating principle of the graphite co-intercalation energy harvester.

FIG. 35 shows operating principle of the graphite co-intercalation energy harvester.

Figure 36:
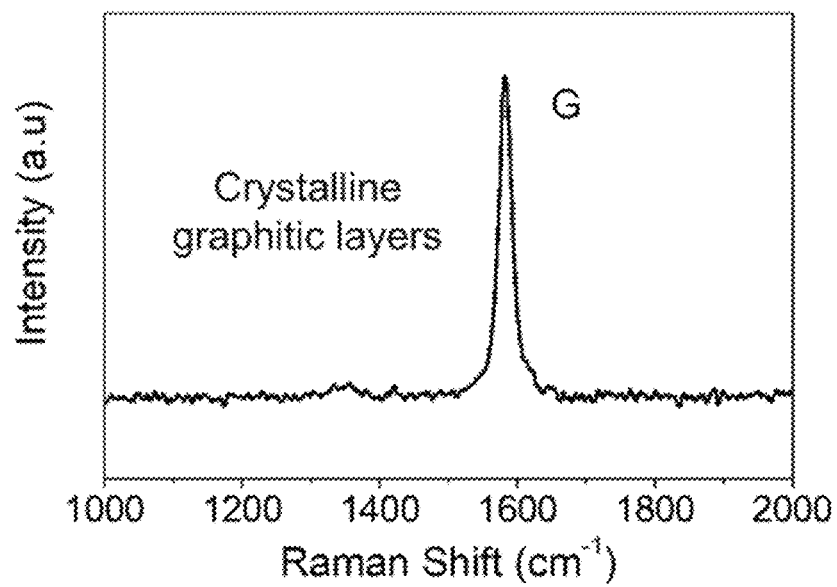
FIG. 36 shows crystalline nature of the MLG as observed in Raman spectra.

FIG. 36 shows crystalline nature of the MLG as observed in Raman spectra.

Figure 37:
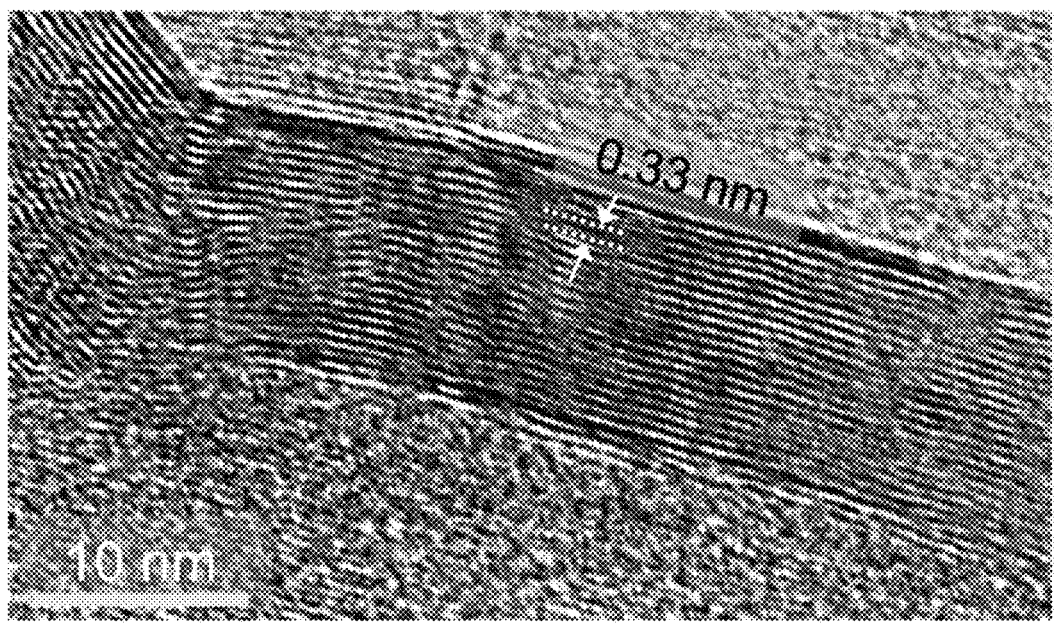
FIG. 37 shows TEM micrograph showing crystalline graphitic planes of a few layers of MLG exfoliated from the as grown material on Ni-foil.

FIG. 37 shows TEM micrograph showing crystalline graphitic planes of a few layers of MLG exfoliated from the as grown material on Ni-foil.

Figure 38:
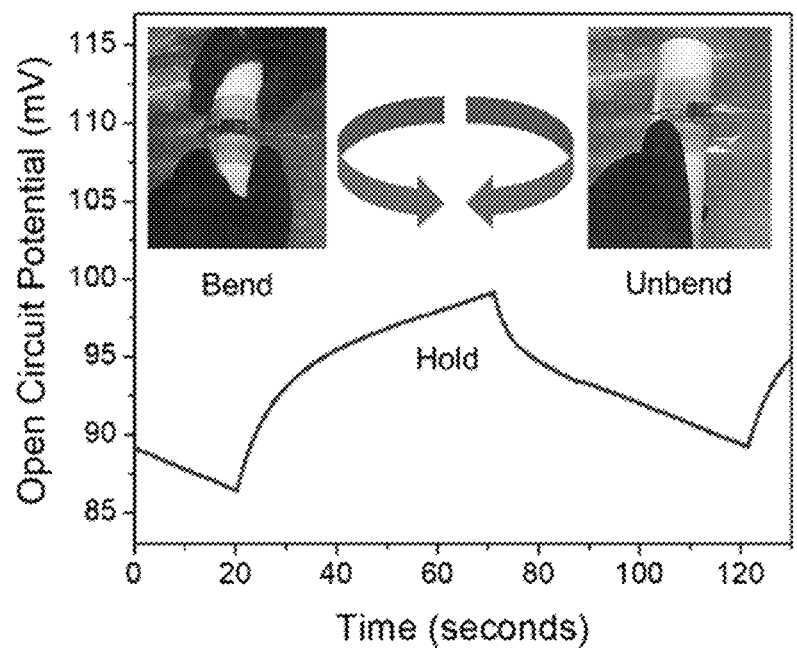
FIG. 38 shows open circuit voltage ($V_{OC}$) measurements during bending and unbending for the graphite co-intercalation energy harvester.

FIG. 38 shows open circuit voltage ($V_{OC}$) measurements during bending and unbending for the graphite co-intercalation energy harvester.

Figure 39:
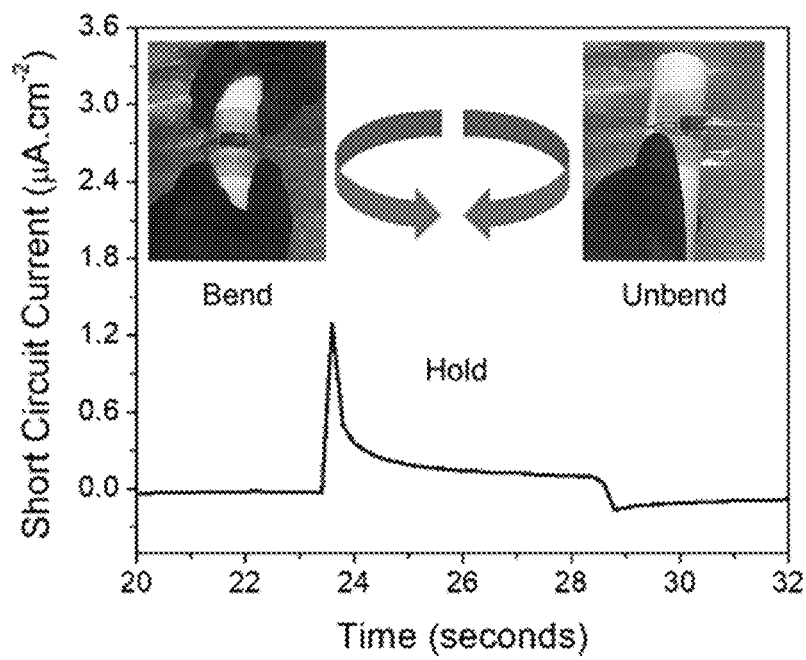
FIG. 39 shows short circuit current (SSC) measurements during bending and unbending for the graphite co-intercalation energy harvester.

FIG. 39 shows short circuit current (SSC) measurements during bending and unbending for the graphite co-intercalation energy harvester.

Figure 40:
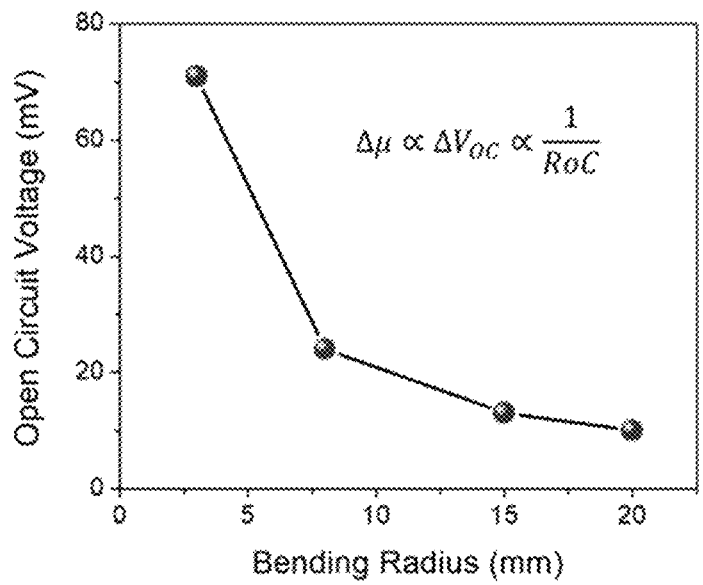
FIG. 40 shows $\Delta V_{OC}$ response from the graphite co-intercalation energy harvester at different bending radii.

FIG. 40 shows $\Delta VOC$ response from the graphite co-intercalation energy harvester at different bending radii.

Figure 41:
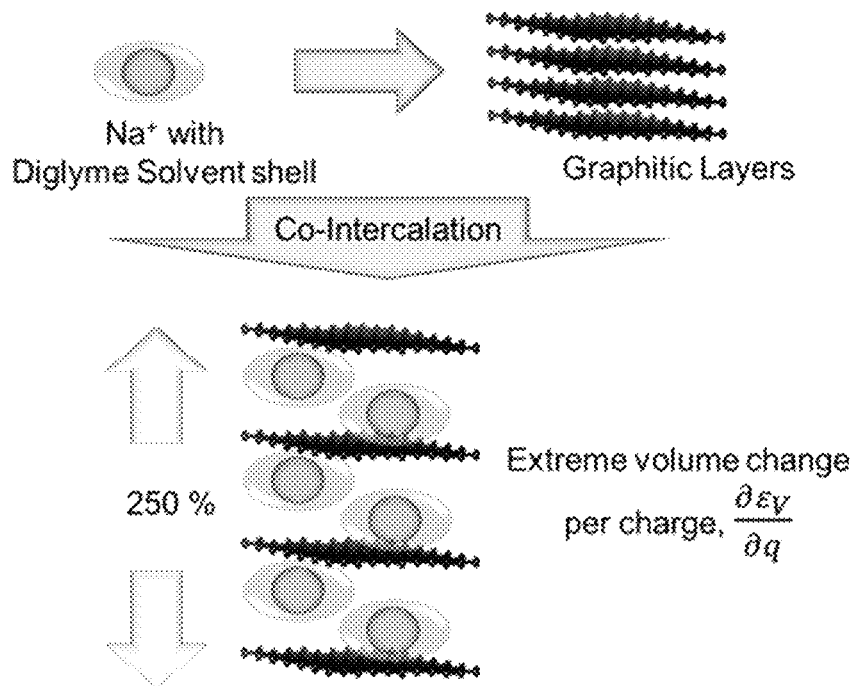
FIG. 41 shows schematic representation of the volumetric strain per charge for the $Na^+$ co-intercalation process.

FIG. 41 shows schematic representation of the volumetric strain per charge for the Na+ co-intercalation process.

Figure 42:
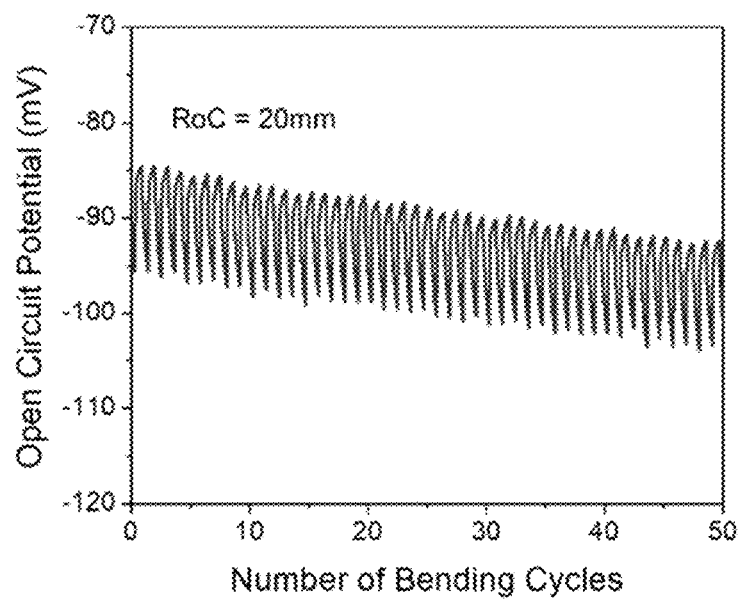
FIG. 42 shows $V_{OC}$ response during repeated bending and unbending for the graphite co-intercalation energy harvester.

FIG. 42 shows $V_{OC}$ response during repeated bending and unbending for the graphite co-intercalation energy harvester.

Figure 43:
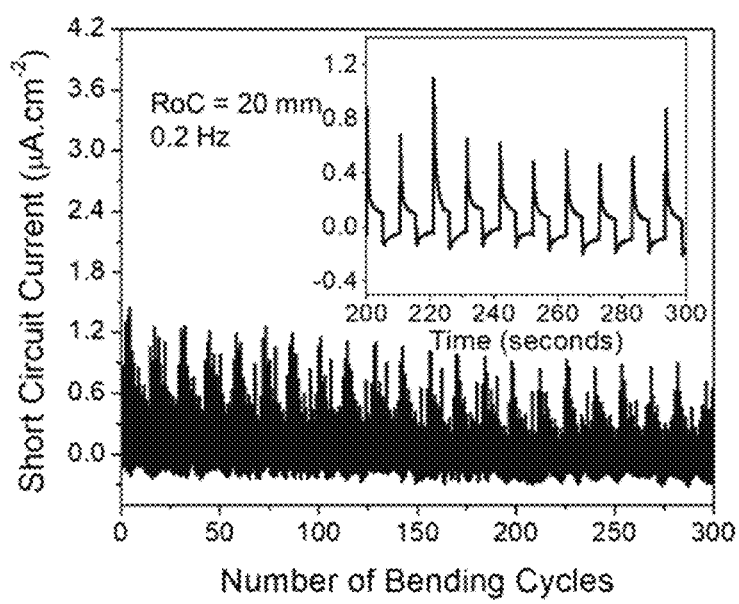
FIG. 43 shows SSC response during repeated bending and unbending tests for the graphite co-intercalation energy harvester.

FIG. 43 shows SSC response during repeated bending and unbending tests for the graphite co-intercalation energy harvester.

Figure 44:
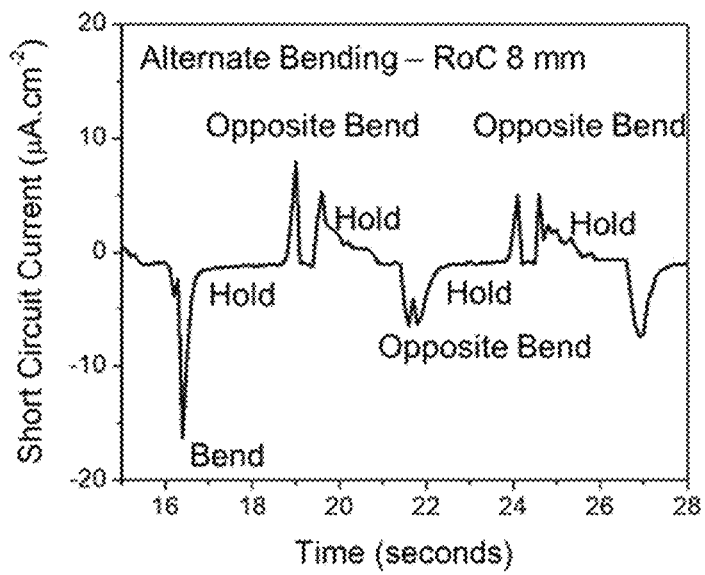
FIG. 44 shows SSC response during repeated alternate bending and unbending tests for the graphite co-intercalation energy harvester.

FIG. 44 shows SSC response during repeated alternate bending and unbending tests for the graphite co-intercalation energy harvester.

Figure 45:
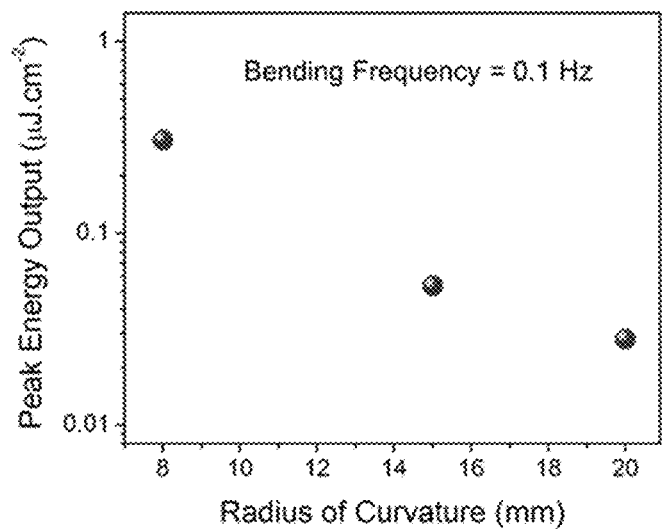
FIG. 45 shows total energy harvested during a 10 second bend and hold time for bending radii of 8 mm and 15 mm for the graphite co-intercalation energy harvester.

FIG. 45 shows total energy harvested during a 10 second bend and hold time for bending radii of 8 mm and 15 mm for the graphite co-intercalation energy harvester.

Figure 46:
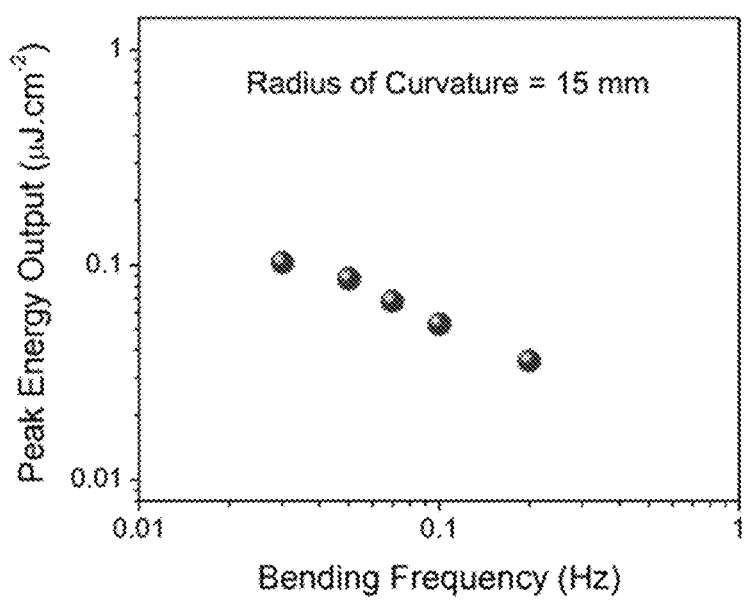
FIG. 46 shows total energy harvested during a fixed bending motion with radii of 15 mm and varying hold times for the graphite co-intercalation energy harvester.

FIG. 46 shows total energy harvested during a fixed bending motion with radii of 15 mm and varying hold times for the graphite co-intercalation energy harvester.

Figure 47:
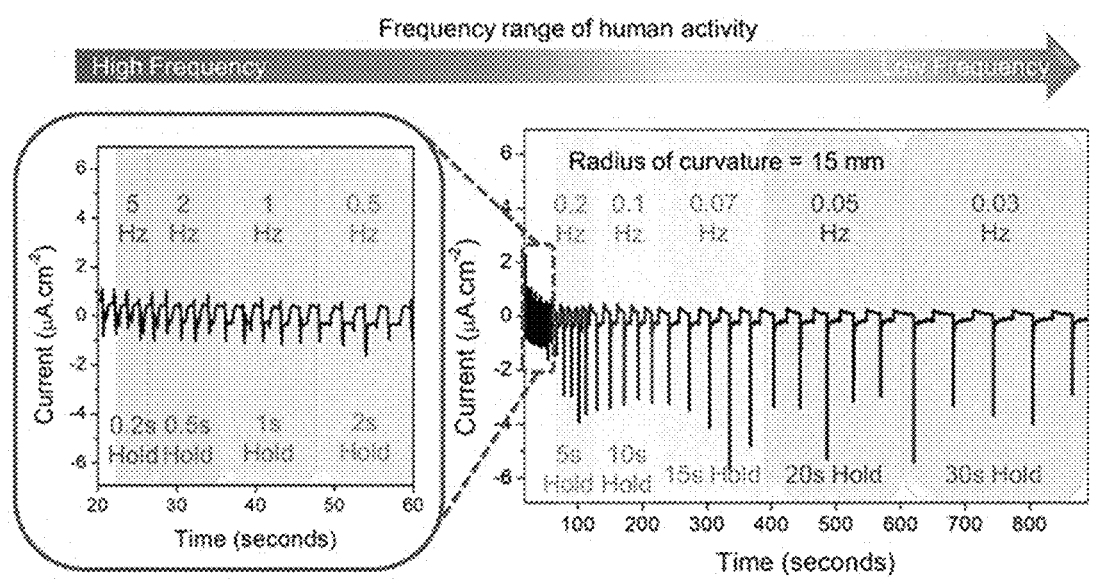
FIG. 47 shows frequency response of the graphite co-intercalation energy harvester at various bend-cycle frequencies at RoC of 15 mm on the same device. The currents were normalized to the active bending area of the harvester.

FIG. 47 shows frequency response of the graphite co-intercalation energy harvester at various bend-cycle frequencies at RoC of 15 mm on the same device. The currents were normalized to the active bending area of the harvester.

Figure 48:
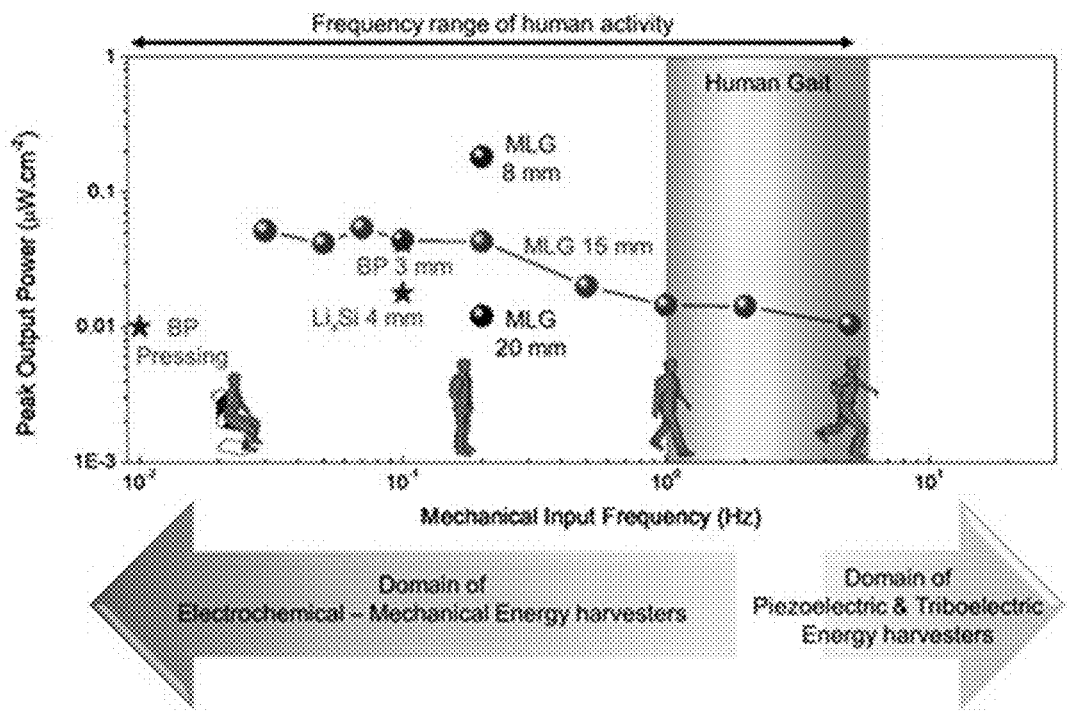
FIG. 48 shows peak output power of the graphite co-intercalation harvester when compared to various electrochemical-mechanical energy harvesters from literature at different frequencies of human activity comparing specific bending radii and pressing modes.

FIG. 48 shows peak output power of the graphite co-intercalation harvester when compared to various electrochemical-mechanical energy harvesters from literature at different frequencies of human activity comparing specific bending radii and pressing modes.

Figure 49:
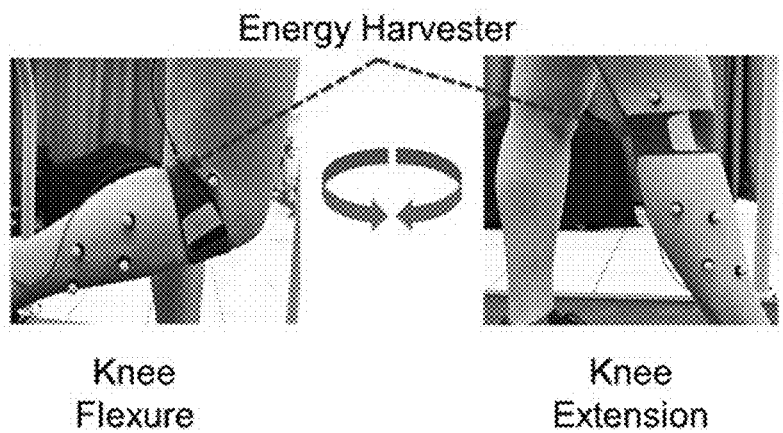
FIG. 49 shows major knee events during human gait.

FIG. 49 shows major knee events during human gait.

Figure 50:
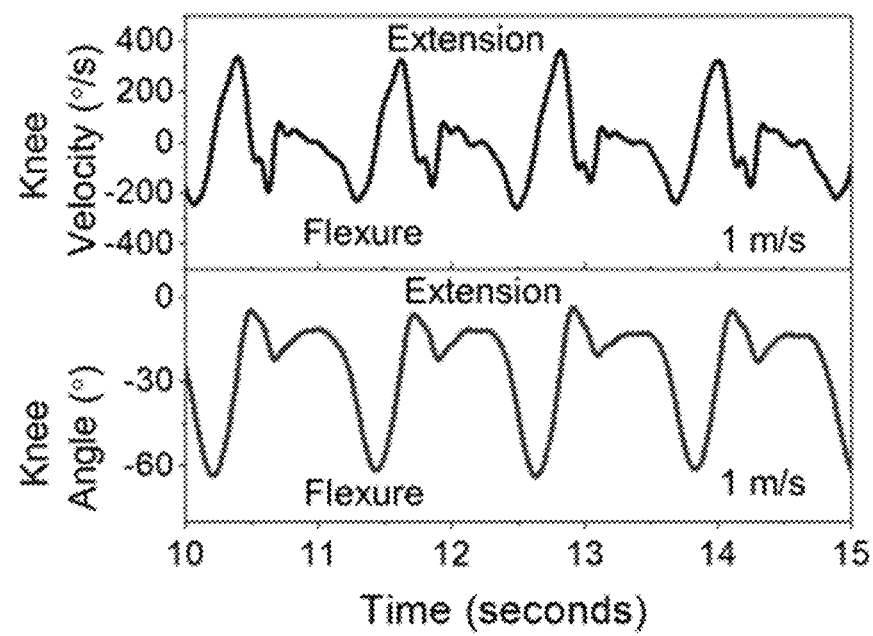
FIG. 50 shows knee velocity and knee angle measurements obtained during different walking speeds.

FIG. 50 shows knee velocity and knee angle measurements obtained during different walking speeds.

Figure 51:
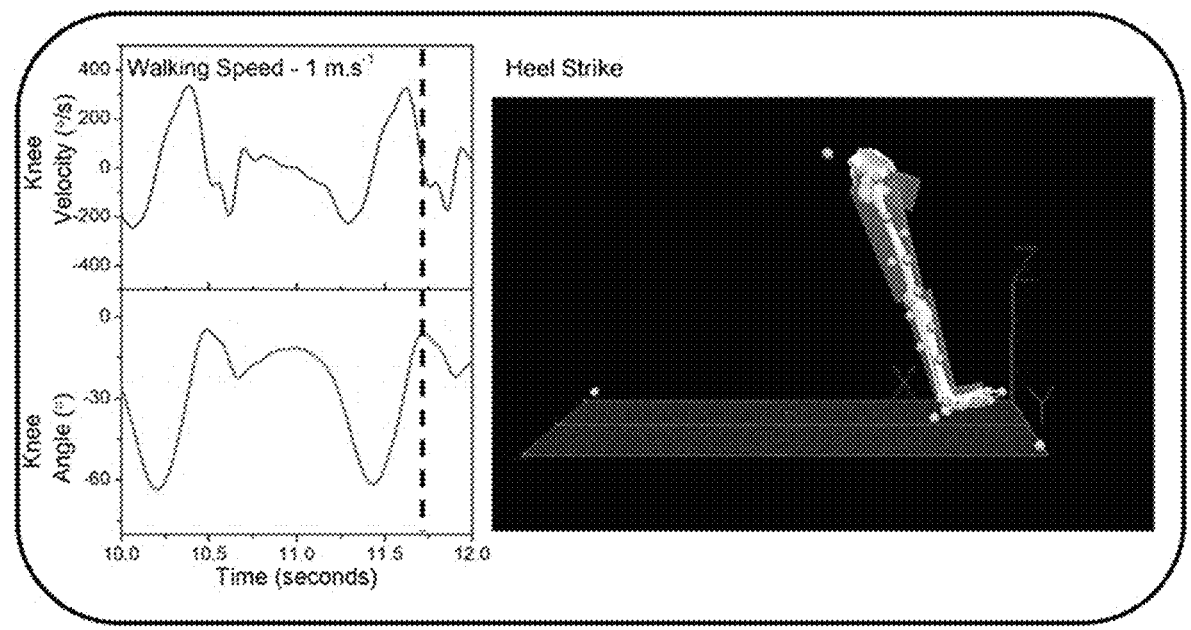
FIG. 51 shows major knee events during human walking at a fixed speed—knee angle and knee velocity observations during heel strike.

FIG. 51 shows major knee events during human walking at a fixed speed—knee angle and knee velocity observations during heel strike.

Figure 52:
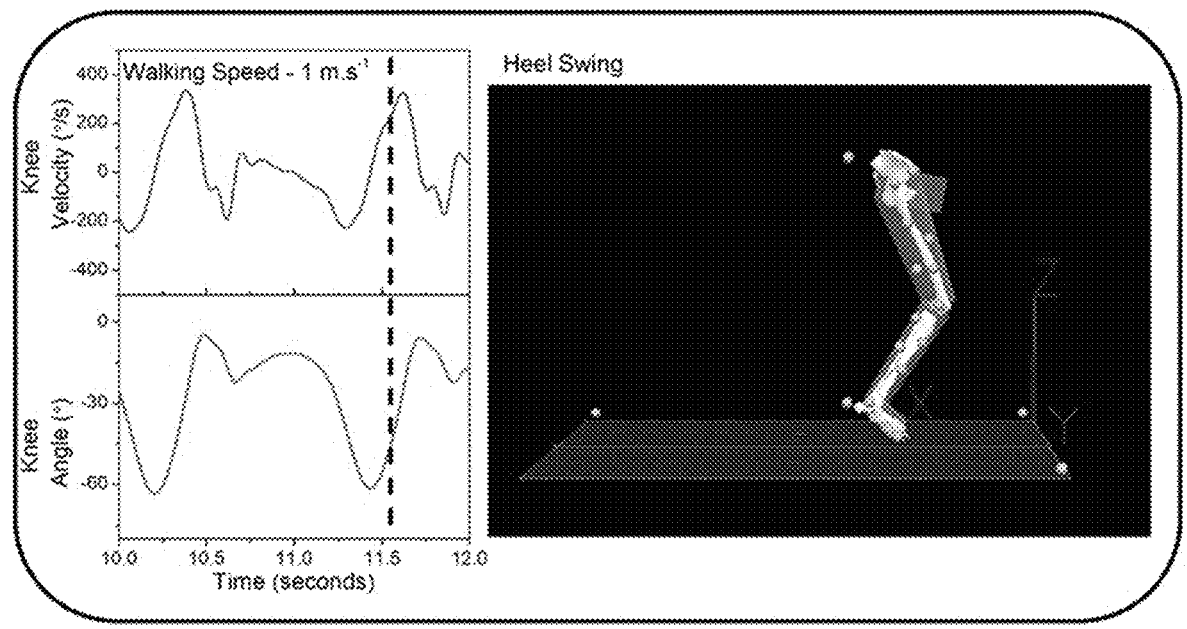
FIG. 52 shows major knee events during human walking at a fixed speed—knee angle and knee velocity observations during heel swing.

FIG. 52 shows major knee events during human walking at a fixed speed—knee angle and knee velocity observations during heel swing.

Figure 53:
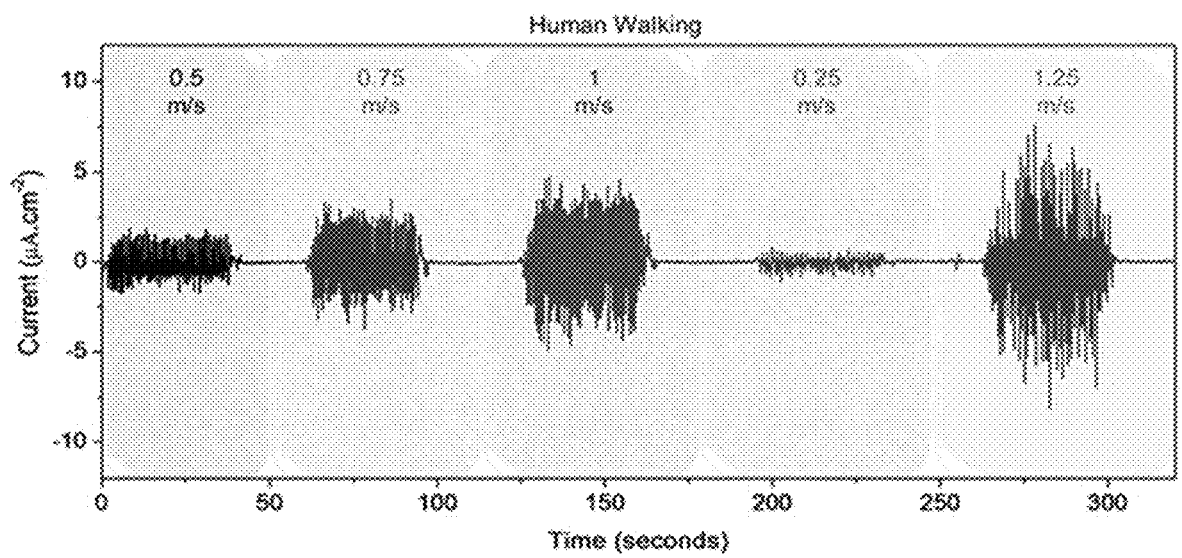
FIG. 53 shows current response of the graphite co-intercalation energy harvester integrated into a fabric worn around the knee during human walking trials at different speeds.
Figure 54:
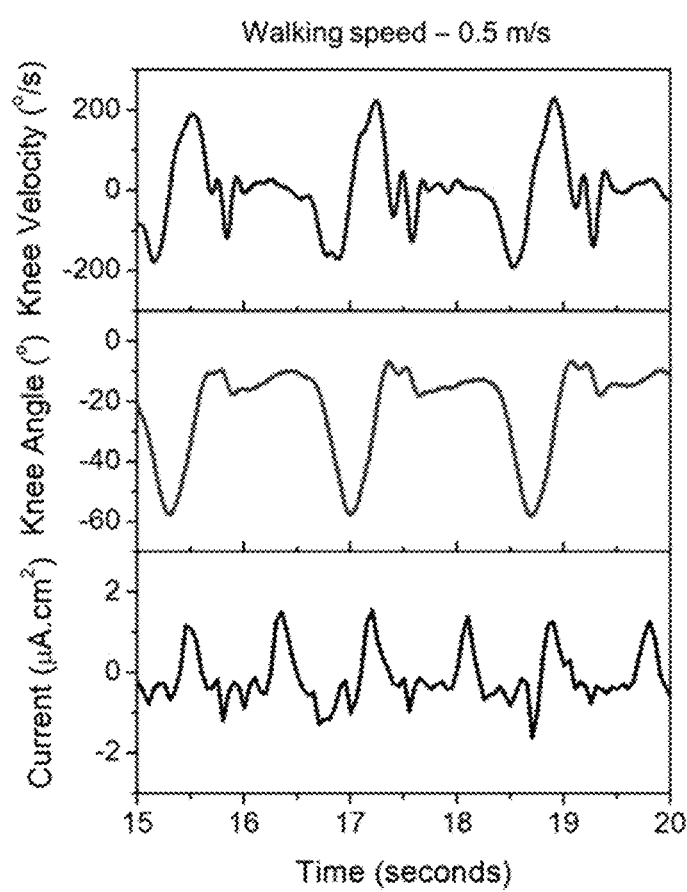
FIG. 54 shows simultaneous measurements of knee velocity, knee angle and current response of the harvester at walking speeds of 0.5 m·s$^{-1}$.

FIG. 53 shows current response of the graphite co-intercalation energy harvester integrated into a fabric worn around the knee during human walking trials at different speeds FIG. 54 shows simultaneous measurements of knee velocity, knee angle and current response of the harvester at walking speeds of 0.5 m·s$^{-1}$.

Figure 55:
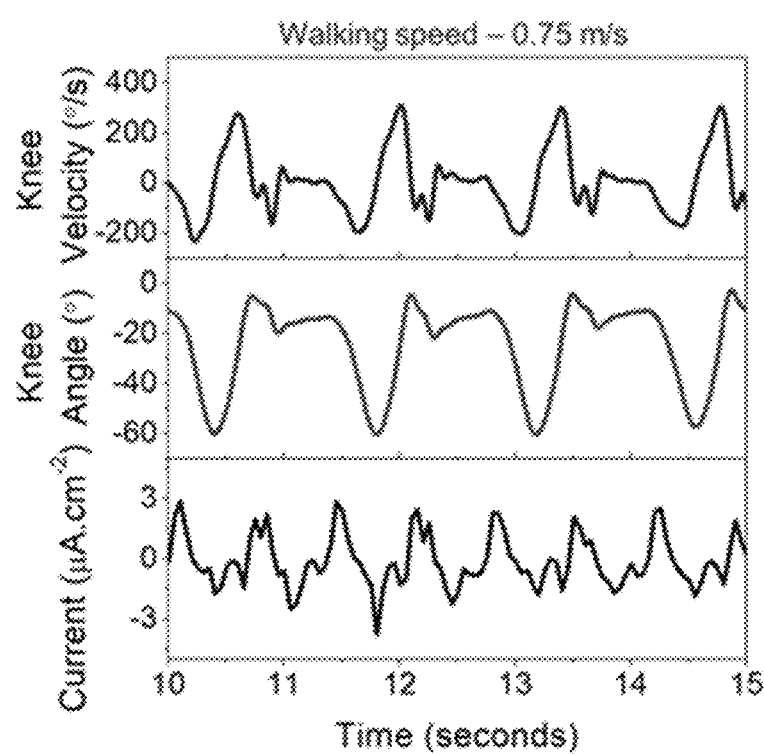
FIG. 55 shows simultaneous measurements of knee velocity, knee angle and current response of the harvester at walking speeds of 0.75 m·s$^{-1}$.

FIG. 55 shows simultaneous measurements of knee velocity, knee angle and current response of the harvester at walking speeds of 0.75 m·s$^{-1}$.

Figure 56:
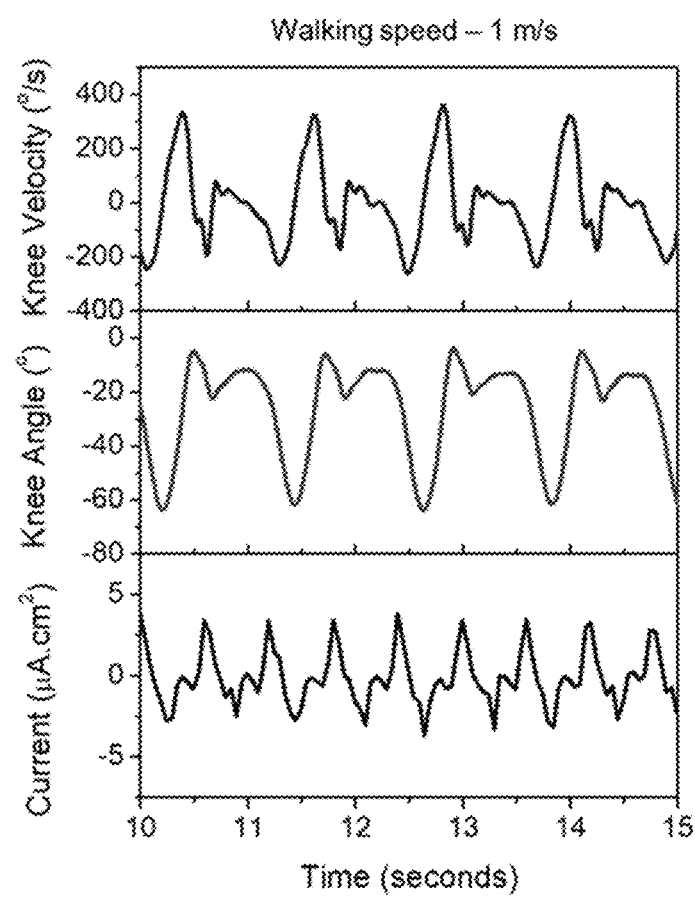
FIG. 56 shows simultaneous measurements of knee velocity, knee angle and current response of the harvester at walking speeds of 1 m·s$^{-1}$.

FIG. 56 shows simultaneous measurements of knee velocity, knee angle and current response of the harvester at walking speeds of 1 m·s$^{-1}$.

Figure 57:
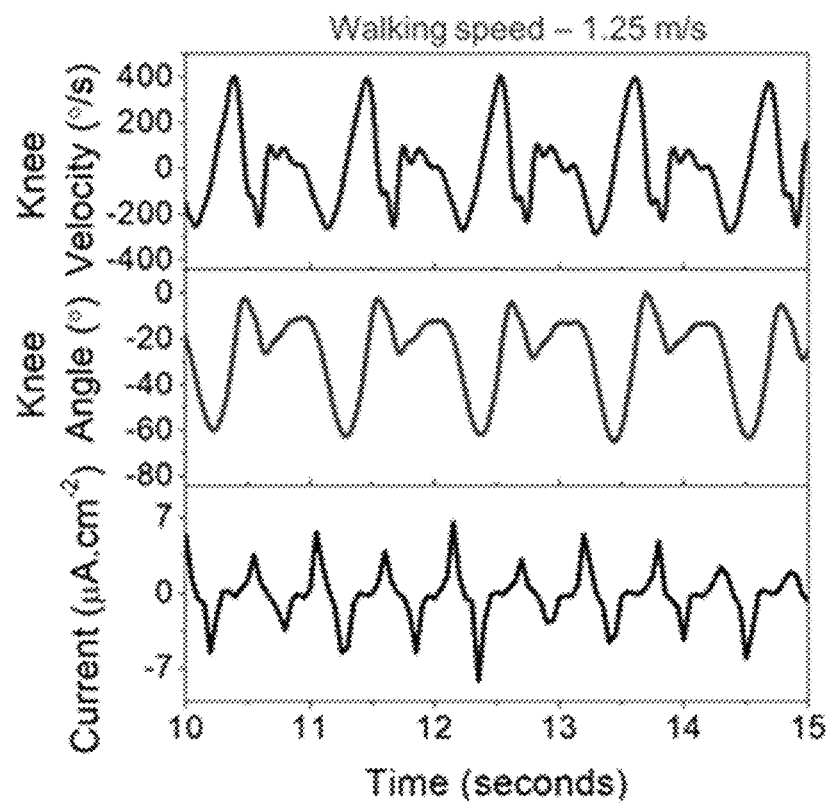
FIG. 57 shows simultaneous measurements of knee velocity, knee angle and current response of the harvester at walking speeds of 1.25 m·s$^{-1}$.

FIG. 57 shows simultaneous measurements of knee velocity, knee angle and current response of the harvester at walking speeds of 1.25 m·s$^{-1}$.

Figure 58:
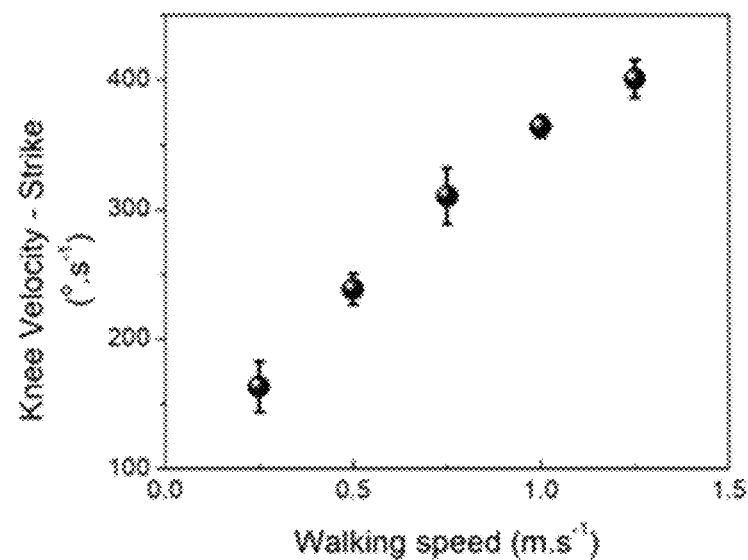
FIG. 58 shows changes to average knee velocity with varying walking speeds during heel strike phase.

FIG. 58 shows changes to average knee velocity with varying walking speeds during heel strike phase.

Figure 59:
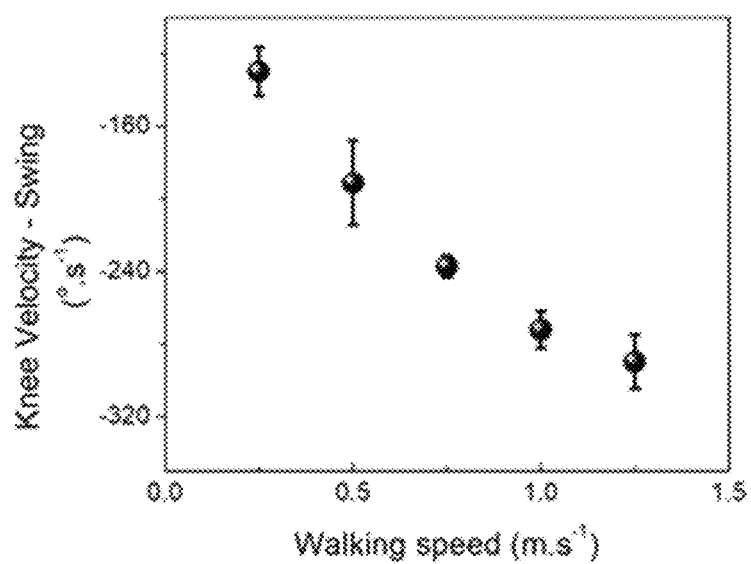
FIG. 59 shows changes to average knee velocity with varying walking speeds during swing phase.

FIG. 59 shows changes to average knee velocity with varying walking speeds during swing phase.

Figure 60:
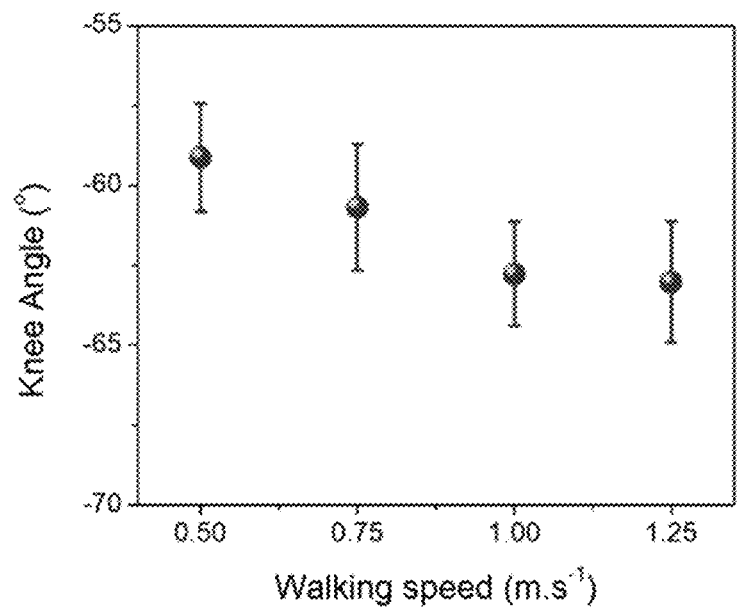
FIG. 60 shows changes to knee angle with varying walking speeds during knee flexure.

FIG. 60 shows changes to knee angle with varying walking speeds during knee flexure.

Figure 61:
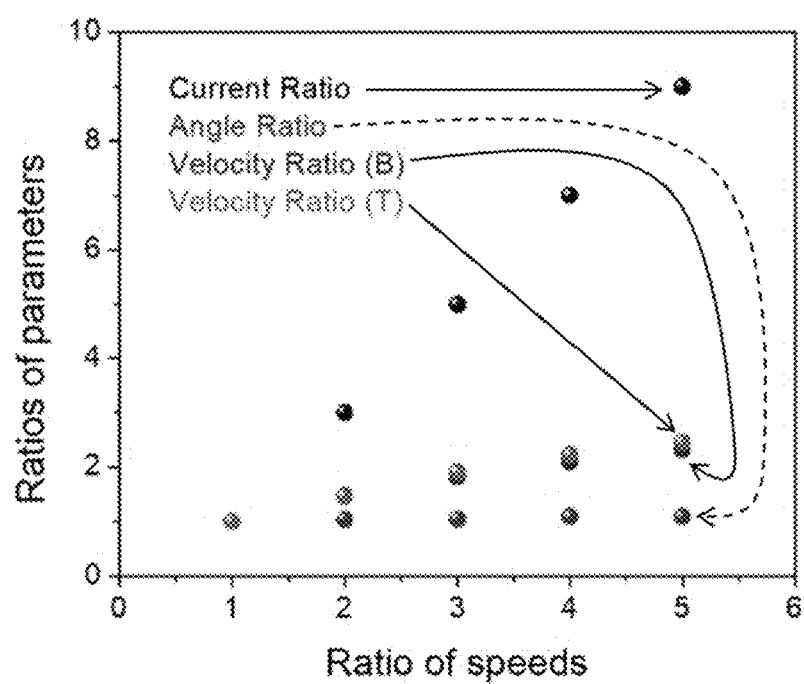
FIG. 61 shows the relationship between knee angle, knee velocity and measured current output from the harvester at different walking speeds.

FIG. 61 shows the relationship between knee angle, knee velocity and measured current output from the harvester at different walking speeds.

One application of these devices is fabric infiltrated with the 2D materials and combined with solid-state electrolytes to enable energy harvesting fabrics.

An example use of this device to produce electrical signal upon movement that can be used for purposes of biomechanical sensing, e.g., an article of clothing that can give spatial information regarding movement of a joint or a part of the body.

Example 3

Described herein is a device that converts mechanical forces at low frequencies (generally <5 Hz) into an electrical signal for energy harvesting and/or sensing purposes. The device can achieve this by using ion-inserted electrodes comprising two identical partially charged metal alloys, which can comprise a high ion species content. This device has transient capability wherein it is comprised of materials which can be triggered to dissolve completely using a suitable trigger solution after its intended use.

The devices described herein can comprise lithiated aluminum alloy on Al foils (e.g., lithiated with Li' species) and combined in a similar configuration as in Example 1 and Example 2. The device showed good stability during repeated mechanical inputs and was triggered to undergo complete dissolution of all the components in in 30 min using a 2 M KOH trigger solution.

Figure 62:
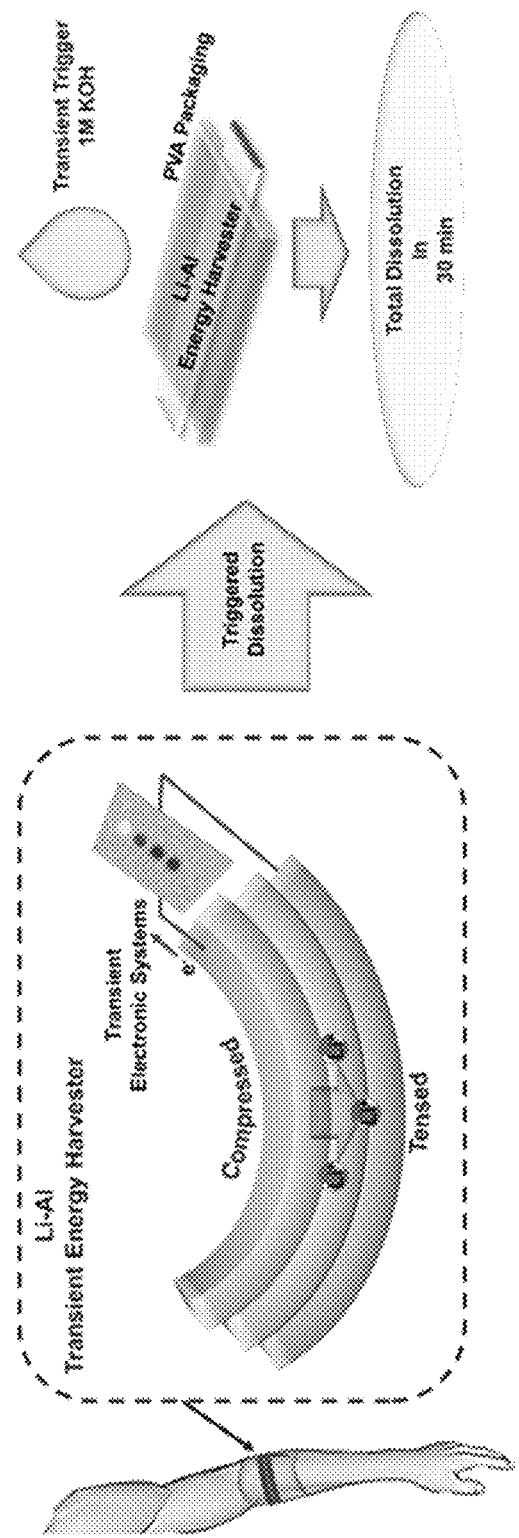
FIG. 62 shows schematic representation of the operation mode and transient behavior of the Li—Al transient energy harvester.

FIG. 62 shows schematic representation of the operation mode and transient behavior of the Li—Al transient energy harvester.

Figure 63:
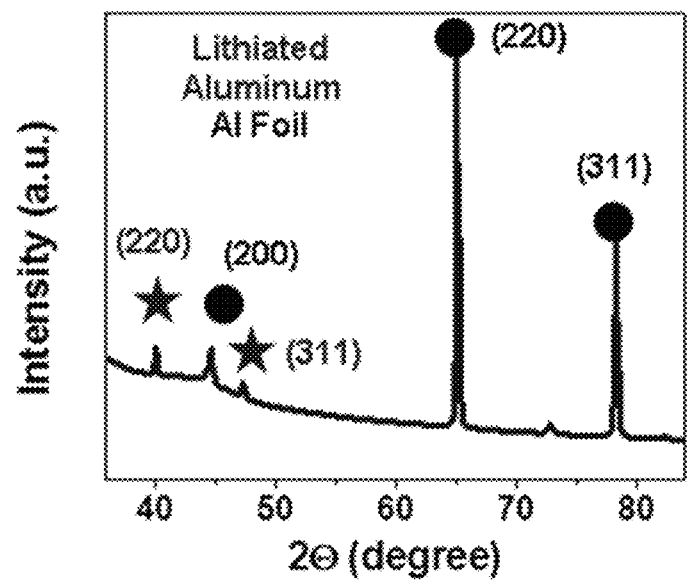
FIG. 63 shows X-Ray diffractogram of the Li—Al alloy on Al foil.

FIG. 63 shows X-Ray diffractogram of the Li—Al alloy on Al foil.

Figure 64:
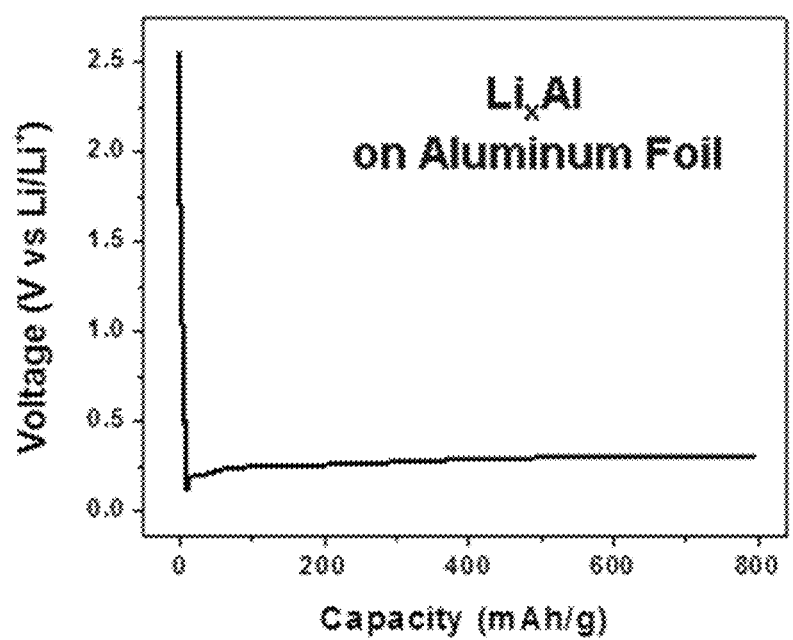
FIG. 64 shows the lithiation profile of the aluminum foil (500 nm lithiated of ~14 microns).

FIG. 64 shows the lithiation profile of the aluminum foil (500 nm lithiated of ~14 microns).

Figure 65:
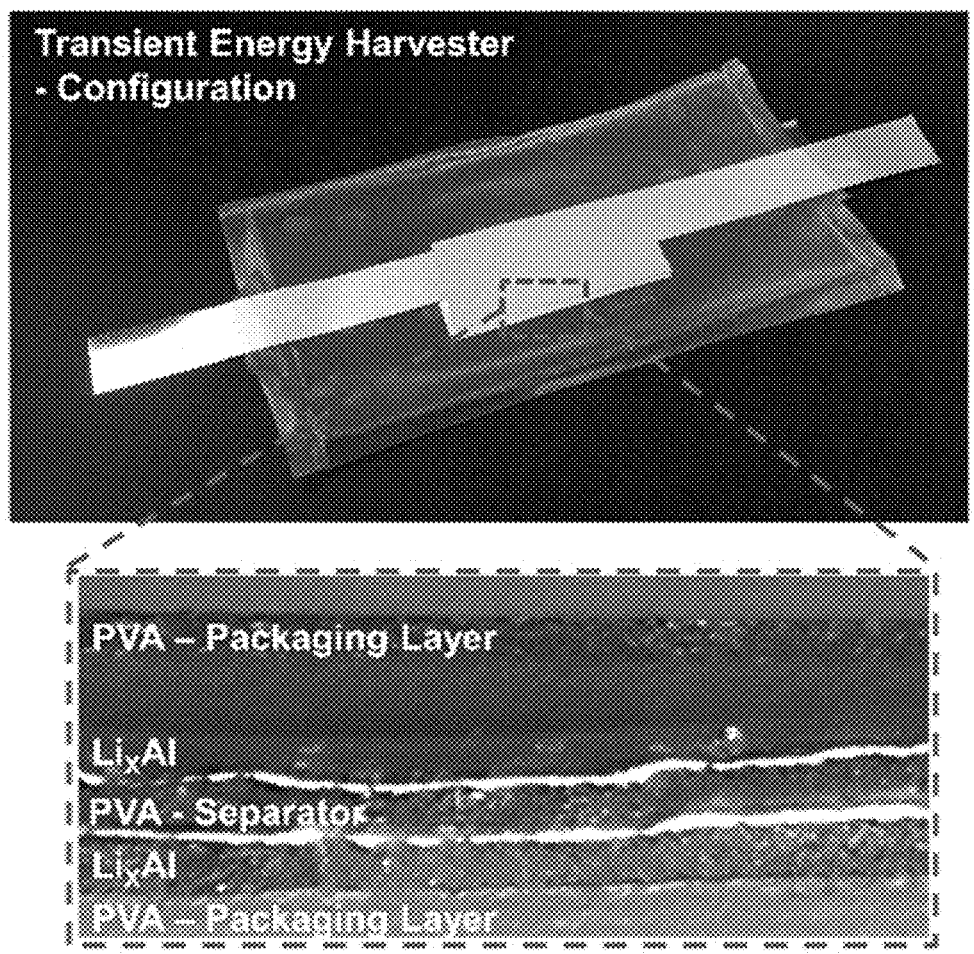
FIG. 65 shows the configuration of the Li—Al transient energy harvester and the cross-sectional optical image.

FIG. 65 shows the configuration of the Li—Al transient energy harvester and the cross-sectional optical image.

Figure 66:
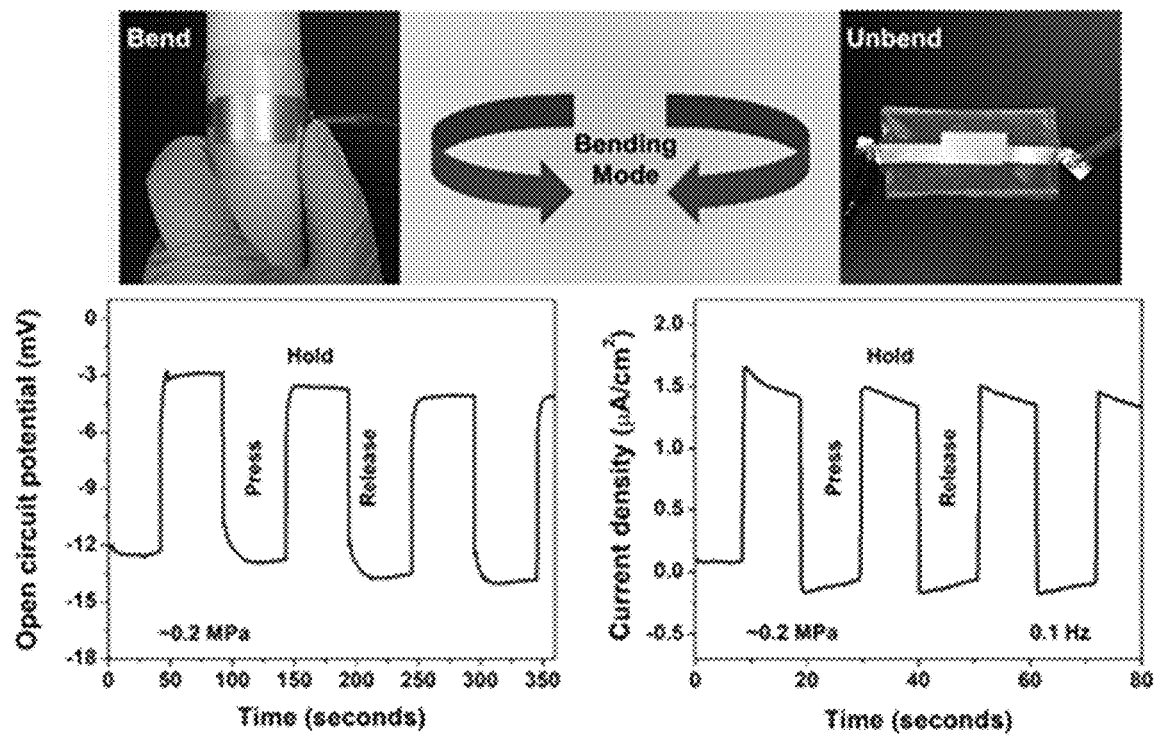
FIG. 66 shows the $V_{OC}$ and SSC response of the Li—Al transient energy harvester during bending mode.

FIG. 66 shows the $V_{OC}$ and SSC response of the Li—Al transient energy harvester during bending mode.

Figure 67:
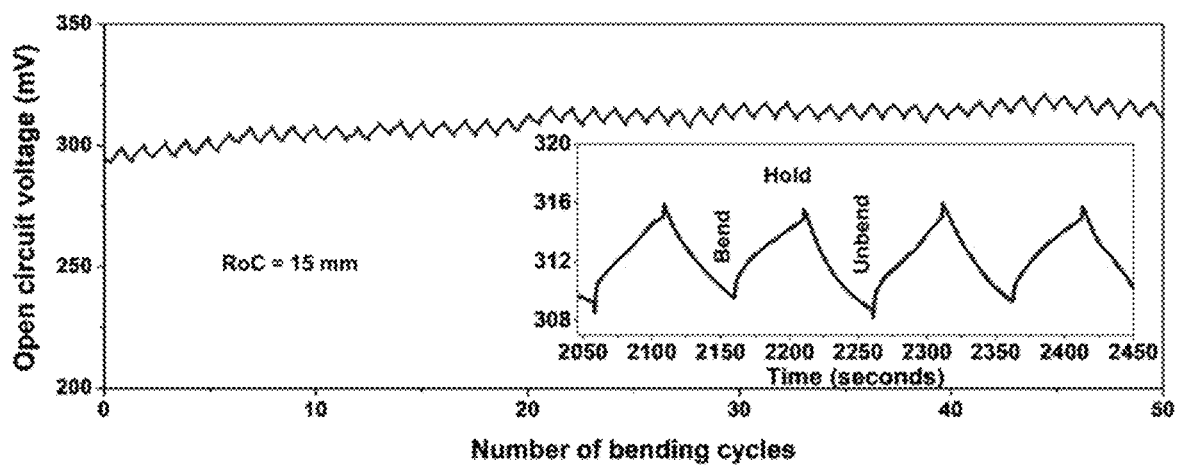
FIG. 67 shows the $V_{OC}$ response of the Li—Al transient energy harvester during repeated bending and unbending.

FIG. 67 shows the $V_{OC}$ response of the Li—Al transient energy harvester during repeated bending and unbending.

Figure 68:
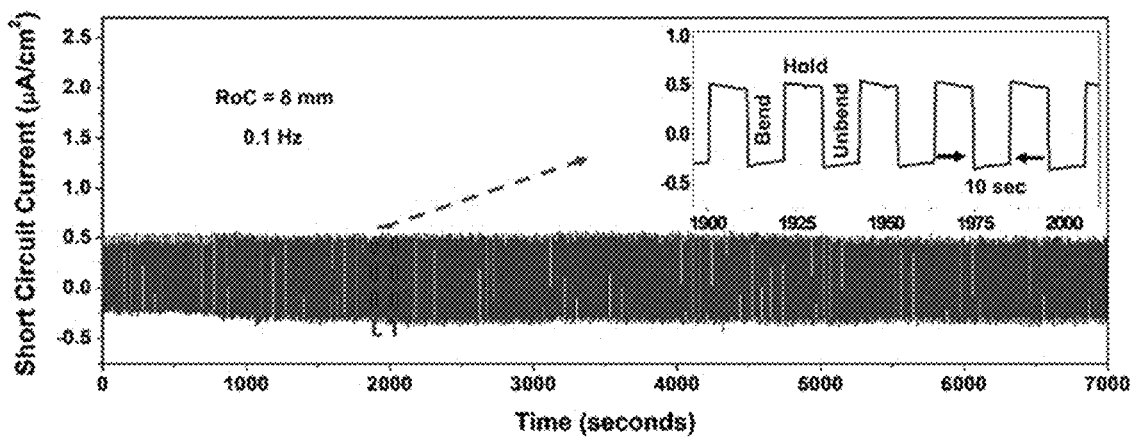
FIG. 68 shows the SSC response of the Li—Al transient energy harvester during repeated bending and unbending.

FIG. 68 shows the SSC response of the Li—Al transient energy harvester during repeated bending and unbending.

Figure 69:
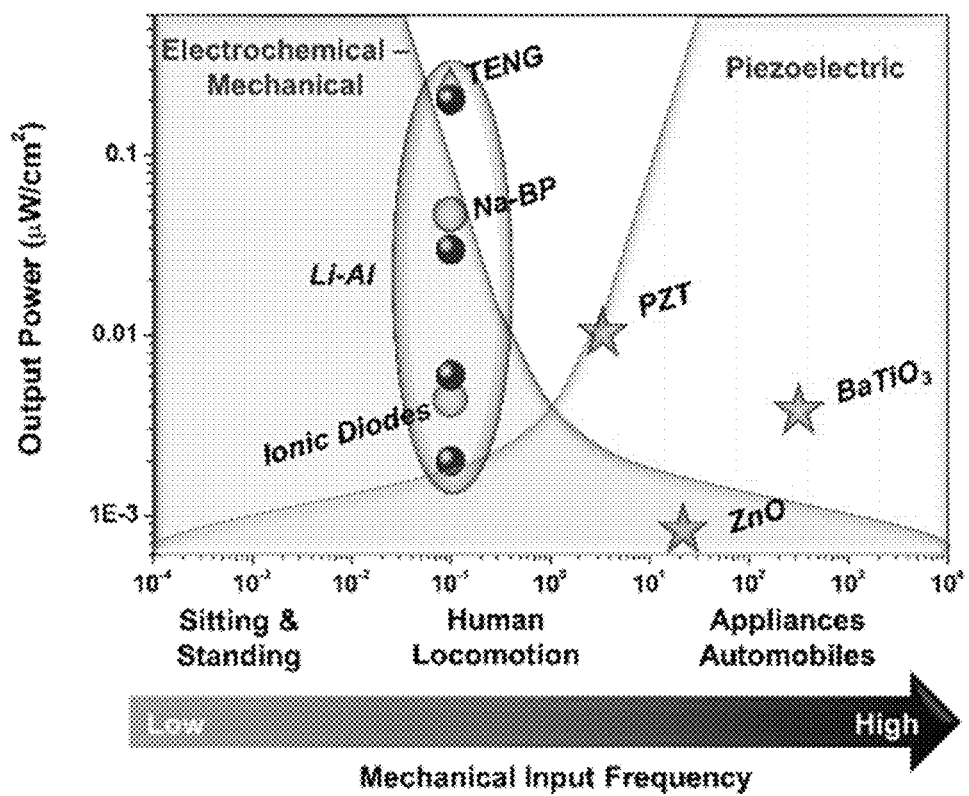
FIG. 69 shows the shows peak output power of the Li—Al transient energy harvester when compared to various electrochemical-mechanical energy harvesters from literature at different frequencies comparing specific bending radii and pressing modes.

FIG. 69 shows the shows peak output power of the Li—Al transient energy harvester when compared to various electrochemical-mechanical energy harvesters from literature at different frequencies comparing specific bending radii and pressing modes.

Figure 70:
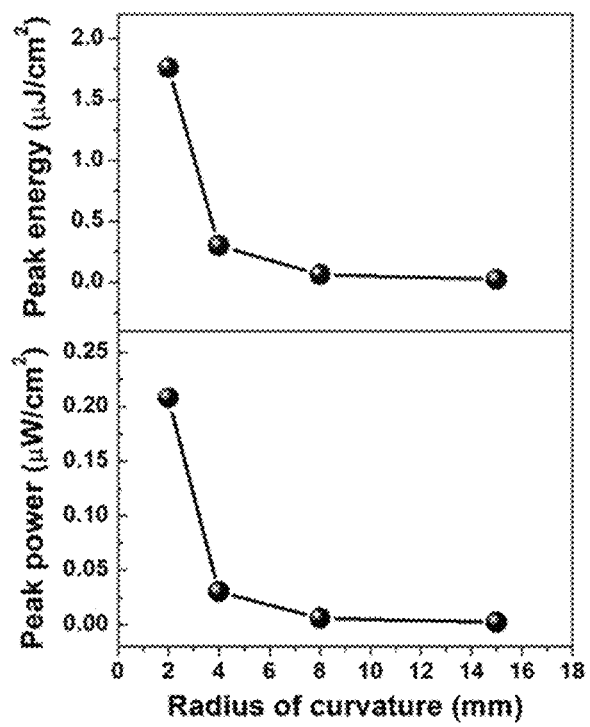
FIG. 70 shows the shows peak output power and the peak output energy of the Li—Al transient energy harvester at specific bending radii.

FIG. 70 shows the shows peak output power and the peak output energy of the Li—Al transient energy harvester at specific bending radii.

Figure 71:
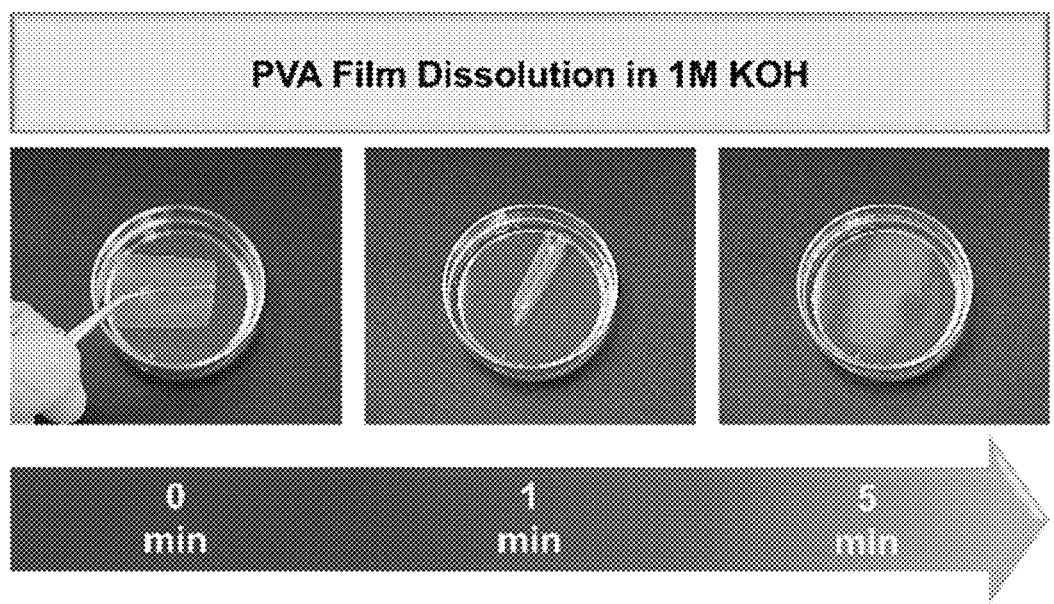
FIG. 71 shows the dissolution behavior of PVA films in the 2M KOH trigger solution.

FIG. 71 shows the dissolution behavior of PVA films in the 2M KOH trigger solution.

Figure 72:
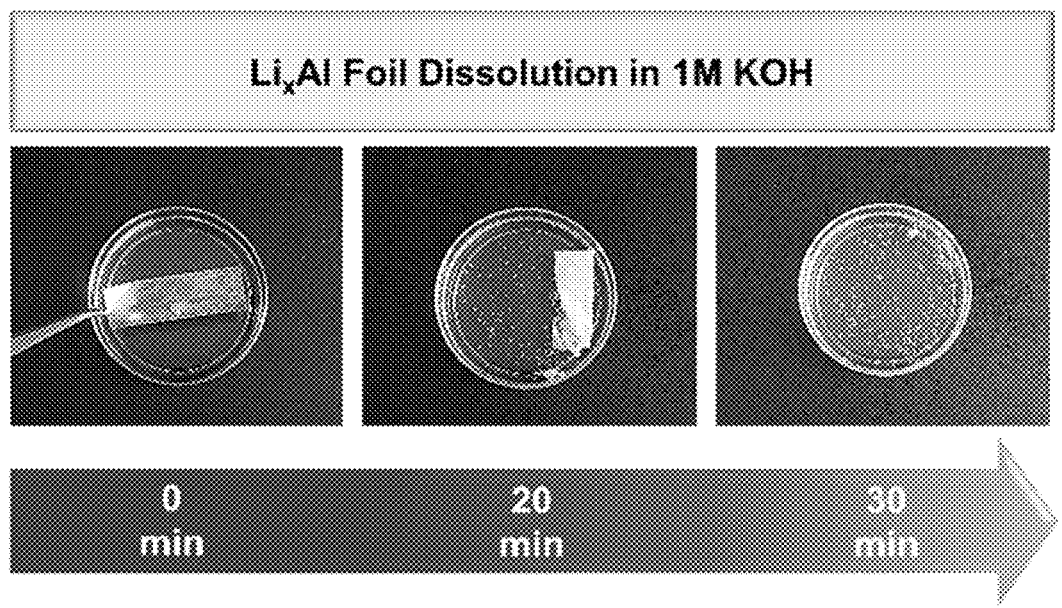
FIG. 72 shows the dissolution behavior of lithiated aluminum foil in the 2M KOH trigger solution.

FIG. 72 shows the dissolution behavior of lithiated aluminum foil in the 2M KOH trigger solution.

Figure 73:
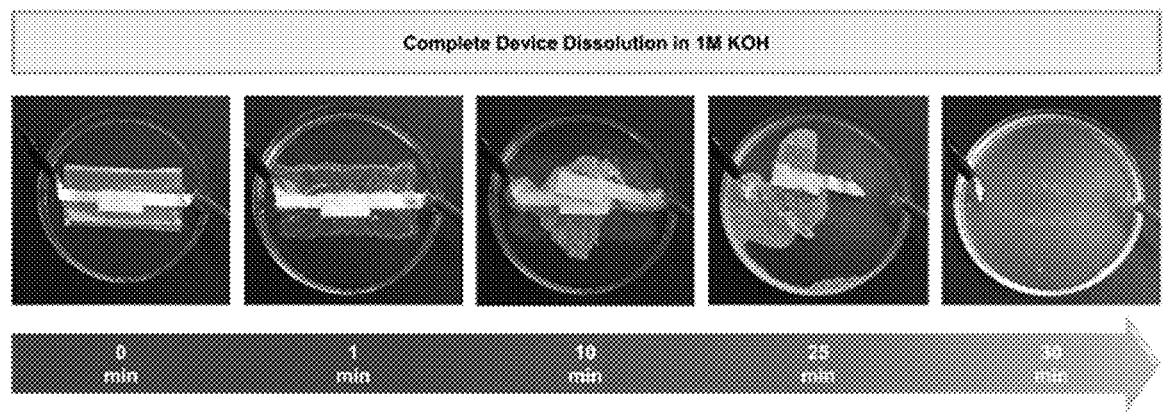
FIG. 73 shows the dissolution behavior of the Li—Al transient energy harvester in the 2M KOH trigger solution showing complete dissolution around 30 min.

FIG. 73 shows the dissolution behavior of the Li—Al transient energy harvester in the 2 M KOH trigger solution showing complete dissolution around 30 min.

Figure 74:
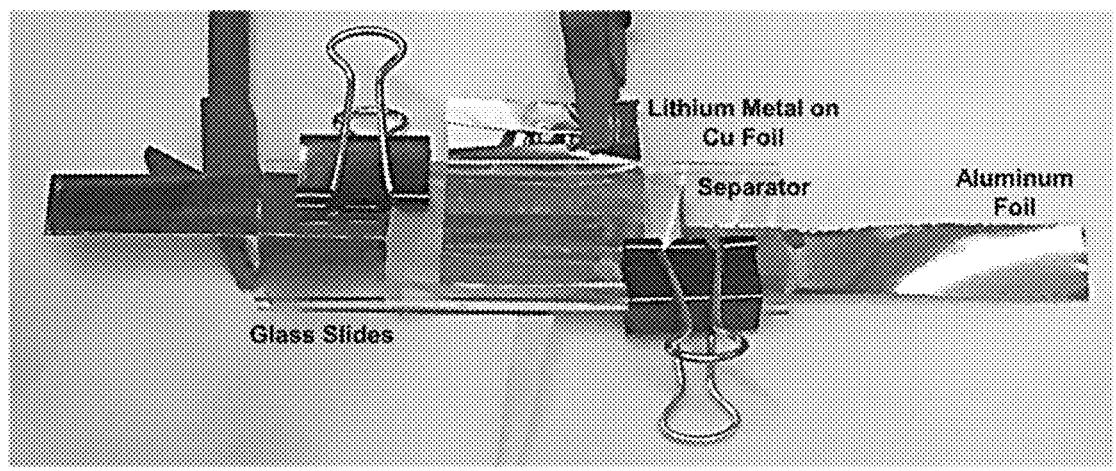
FIG. 74 shows the custom-made apparatus for the lithiation procedure of the aluminum foil.

FIG. 74 shows the custom-made apparatus for the lithiation procedure of the aluminum foil.

Figure 75:
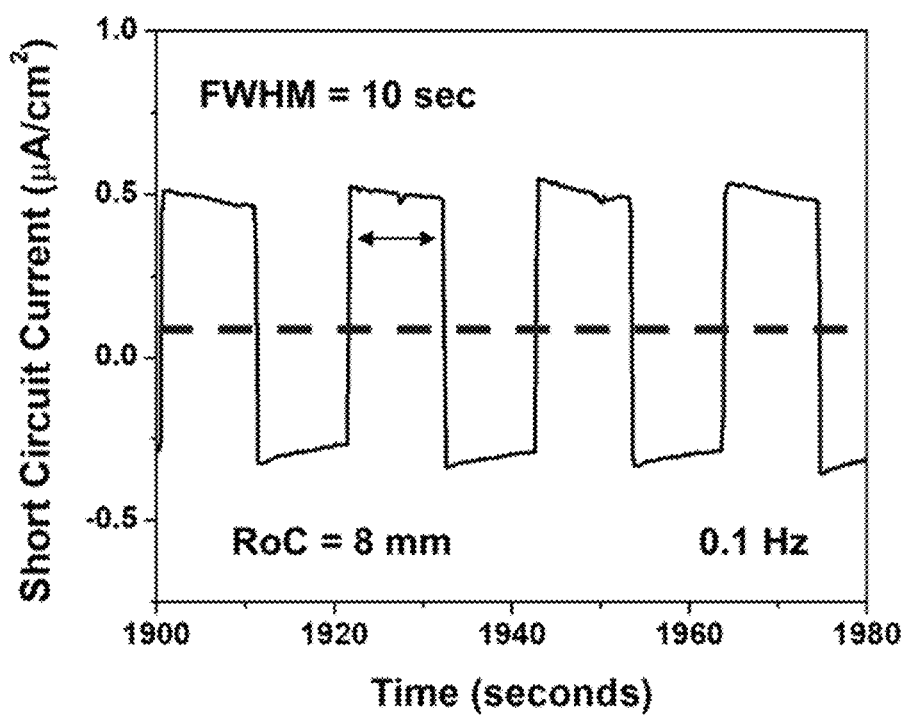
FIG. 75 shows the SSC response of the Li—Al transient energy harvester at RoC of 8 mm at 0.1 Hz showing full width at half maximum of the current response as 10 seconds.

FIG. 75 shows the SSC response of the Li—Al transient energy harvester at RoC of 8 mm at 0.1 Hz showing full width at half maximum of the current response as 10 seconds.

Figure 76:
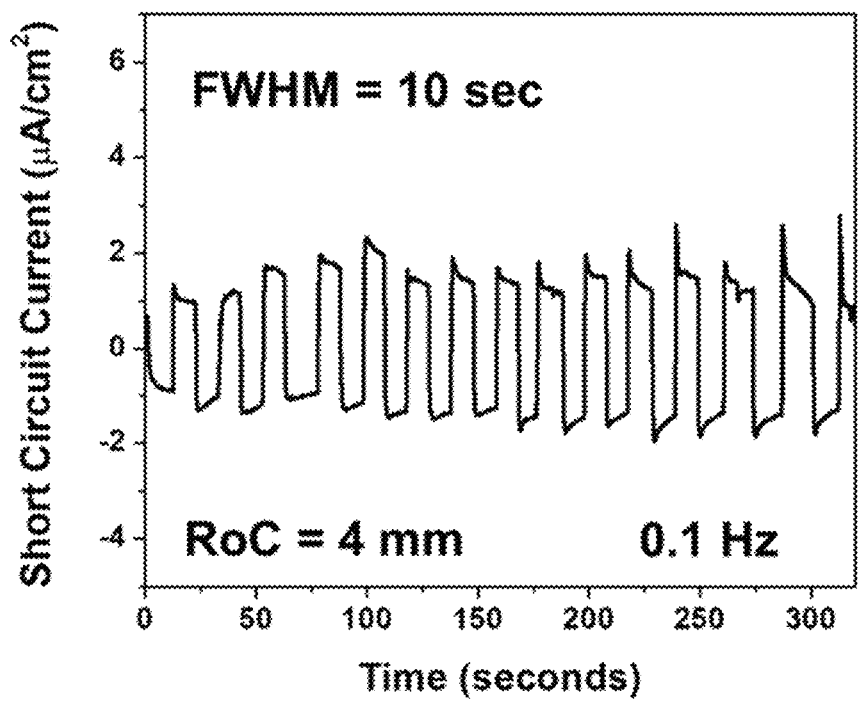
FIG. 76 shows the SSC response of the Li—Al transient energy harvester at RoC of 4 mm at 0.1 Hz showing full width at half maximum of the current response as 10 seconds.

FIG. 76 shows the SSC response of the Li—Al transient energy harvester at RoC of 4 mm at 0.1 Hz showing full width at half maximum of the current response as 10 seconds.

Figure 77:
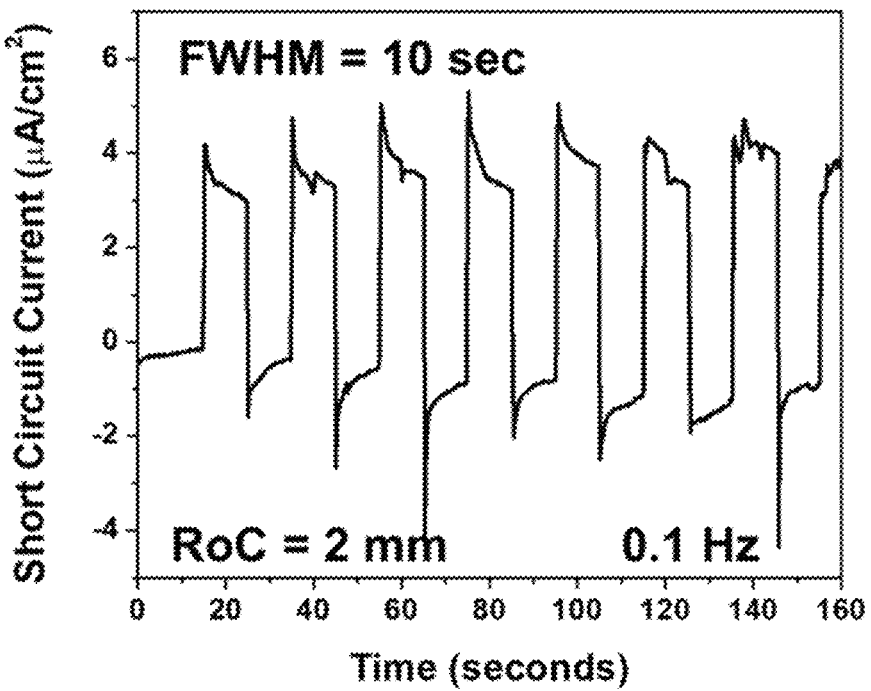
FIG. 77 shows the SSC response of the Li—Al transient energy harvester at RoC of 2 mm at 0.1 Hz showing full width at half maximum of the current response as 10 seconds.

FIG. 77 shows the SSC response of the Li—Al transient energy harvester at RoC of 2 mm at 0.1 Hz showing full width at half maximum of the current response as 10 seconds.

Figure 78:
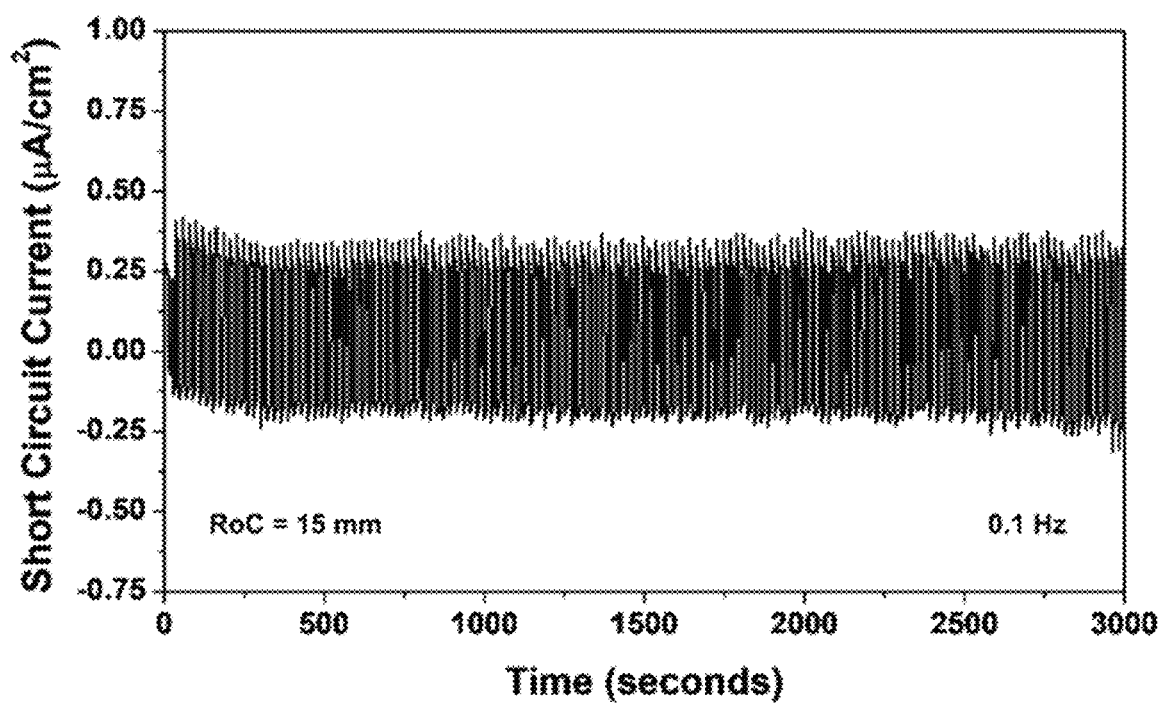
FIG. 78 shows the SSC cycling response of the Li—Al transient energy harvester at RoC of 15 mm at 0.1 Hz showing full width at half maximum of the current response as 10 seconds.

FIG. 78 shows the SSC cycling response of the Li—Al transient energy harvester at RoC of 15 mm at 0.1 Hz showing full width at half maximum of the current response as 10 seconds.

One application of these devices is fabric infiltrated with the 2D materials and combined with solid-state electrolytes to enable energy harvesting fabrics.

An example use of this device to produce electrical signal upon movement that can be used for purposes of biomechanical sensing, e.g., an article of clothing that can give spatial information regarding movement of a joint or a part of the body.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The methods of the appended claims are not limited in scope by the specific methods described herein, which are intended as illustrations of a few aspects of the claims and any methods that are functionally equivalent are intended to fall within the scope of the claims. Various modifications of the methods in addition to those shown and described herein are intended to fall within the scope of the appended claims. Further, while only certain representative method steps disclosed herein are specifically described, other combinations of the method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

What is claimed is:

1. An energy harvesting device comprising:
   a first electrode comprising a first material;
   a second electrode comprising the first material;
   wherein the first material comprises a plurality of particles and a plurality of ions;
   wherein the plurality of ions are intercalated within the plurality of particles; and
   wherein the plurality of ions comprise a plurality of alkali metal ions;
   a porous separator disposed between the first electrode and the second electrode such that the porous separator is in contact with the first electrode and the second electrode, wherein the porous separator further comprises an electrolyte; and
   wherein the energy harvesting device is configured to convert a mechanical strain to an electrical current, thereby harvesting energy.

2. The energy harvesting device of claim 1, wherein the plurality of particles have an average lateral dimension of from 10 nanometers (nm) to 10 micrometers (microns, μm).

3. The energy harvesting device of claim 1, wherein the plurality of particles have an average thickness of from 1 atomic layer to 50 atomic layers.

4. The energy harvesting device of claim 1, wherein the plurality of particles comprise graphite, graphene, aluminum, a metal dichalcogenide, a metal oxide, an allotrope of phosphorous, or a combination thereof.

5. The energy harvesting device of claim 1, wherein the loading of the first material on the first electrode and/or the second electrode is from 0.1 mg/cm$^2$ to 10 mg/cm$^2$.

6. The energy harvesting device of claim 1, wherein the mechanical strain comprises pressing and/or bending the energy harvesting device.

7. The energy harvesting device of claim 1, wherein the mechanical strain is generated at a frequency of 5 Hz or less.

8. The energy harvesting device of claim 1, wherein the mechanical strain is generated by motion of a subject.

9. The energy harvesting device of claim 1, wherein the mechanical strain is generated by human gait.

10. The energy harvesting device of claim 1, wherein the energy harvesting device has a peak power of 1 nW/cm$^2$ or more.

11. The energy harvesting device of claim 1, wherein the energy harvesting device harvests an energy of 0.1 μJ/cm$^2$ or more.

12. The energy harvesting device of claim 1, wherein the energy harvesting device harvests energy with an efficiency of 20% or more.

13. The energy harvesting device of claim 1, wherein the energy harvesting device further comprises a packaging material substantially encapsulating the device.

14. The energy harvesting device of claim 1, wherein the energy harvesting device is dissolvable.

15. A method of harvesting energy using the energy harvesting device of claim 1, the method comprising applying a mechanical strain to the energy harvesting device, thereby converting the mechanical strain to an electrical current and harvesting the energy.

16. A method of making the energy harvesting device of claim 1, the method comprising:
   dispersing the first material in a solution, thereby forming a mixture;
   depositing the mixture on a conducting layer, thereby forming the first electrode;
   repeating the dispersing and depositing steps to form the second electrode or cutting the first electrode into two pieces thereby forming the first electrode and the second electrode; and
   sandwiching the porous separator between the first electrode and the second electrode, thereby forming the energy harvesting device.

17. A fabric or textile comprising the energy harvesting device of claim 1.

18. A wearable energy harvesting device comprising a fabric or textile impregnated with the energy harvesting device of claim 1.

* * * * *